United States Patent
Beckwith et al.

(10) Patent No.: US 10,844,002 B2
(45) Date of Patent: Nov. 24, 2020

(54) LIPIDS AND LIPID COMPOSITIONS FOR THE DELIVERY OF ACTIVE AGENTS

(71) Applicant: Novartis AG, Basel (CH)

(72) Inventors: Rohan Eric John Beckwith, Cambridge, MA (US); Luis Brito, Cambridge, MA (US); Brian Addison DeChristopher, Cambridge, MA (US); Gabriel Grant Gamber, Cambridge, MA (US); Andrew Geall, Cambridge, MA (US); Thomas Zabawa, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/135,116

(22) Filed: Sep. 19, 2018

(65) Prior Publication Data
US 2019/0002393 A1    Jan. 3, 2019

Related U.S. Application Data

(63) Continuation of application No. 15/505,282, filed as application No. PCT/US2015/048535 on Sep. 4, 2015, now Pat. No. 10,125,092.

(60) Provisional application No. 62/046,487, filed on Sep. 5, 2014.

(51) Int. Cl.

| | |
|---|---|
| C07C 219/06 | (2006.01) |
| C07D 211/34 | (2006.01) |
| C07D 295/15 | (2006.01) |
| A61K 47/18 | (2017.01) |
| A61K 47/22 | (2006.01) |
| A61K 9/127 | (2006.01) |
| A61K 9/51 | (2006.01) |
| A61K 31/7105 | (2006.01) |
| A61K 31/711 | (2006.01) |
| A61K 31/713 | (2006.01) |
| C07C 229/12 | (2006.01) |
| C07D 211/62 | (2006.01) |
| C07C 219/16 | (2006.01) |
| C07C 217/58 | (2006.01) |
| C07D 207/08 | (2006.01) |
| A61P 31/12 | (2006.01) |
| A61P 31/16 | (2006.01) |

(52) U.S. Cl.
CPC .......... *C07C 219/06* (2013.01); *A61K 9/1272* (2013.01); *A61K 9/5123* (2013.01); *A61K 31/711* (2013.01); *A61K 31/713* (2013.01); *A61K 31/7105* (2013.01); *A61K 47/18* (2013.01); *A61K 47/22* (2013.01); *A61P 31/12* (2018.01); *A61P 31/16* (2018.01); *C07C 217/58* (2013.01); *C07C 219/16* (2013.01); *C07C 229/12* (2013.01); *C07D 207/08* (2013.01); *C07D 211/34* (2013.01); *C07D 211/62* (2013.01); *C07D 295/15* (2013.01)

(58) Field of Classification Search
CPC .............. A61K 31/7105; A61K 31/711; A61K 31/713; A61K 47/18; A61K 47/22; A61K 9/1272; A61K 9/5123; C07C 217/58; C07C 219/06; C07C 219/16; C07C 229/12; C07D 207/08; C07D 211/34; C07D 211/62; C07D 295/15
USPC ........................................................ 424/450
See application file for complete search history.

(56) References Cited

U.S. PATENT DOCUMENTS

| | | | |
|---|---|---|---|
| 9,504,747 B2 * | 11/2016 | Baryza | .................. C07C 217/58 |
| 10,125,092 B2 * | 11/2018 | Beckwith | ............... A61K 47/18 |
| 2010/0029904 A1 | 2/2010 | Chiba et al. | |
| 2013/0345393 A1 | 12/2013 | Kono et al. | |
| 2014/0296483 A1 | 10/2014 | Takahashi | |

FOREIGN PATENT DOCUMENTS

| | | |
|---|---|---|
| EP | 1927584 | 6/2008 |
| WO | 07034812 A1 | 3/2007 |
| WO | 12121057 A1 | 9/2012 |
| WO | 12121058 A1 | 9/2012 |
| WO | 13089241 A1 | 6/2013 |
| WO | 2013086354 | 6/2013 |

OTHER PUBLICATIONS

Aoki et al., "A Disulfide Bond Replacement Strategy Enables the Efficient Design of Artificial Therapeutic Peptides," Tetrahedron, vol. 70, No. 42, (2014), pp. 7774-7779.

(Continued)

*Primary Examiner* — Janet L Epps-Smith
(74) *Attorney, Agent, or Firm* — Brinks Gilson & Lione

(57) ABSTRACT

This invention provides for a compound of formula (I):

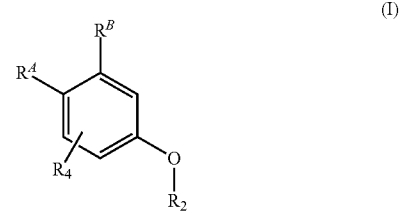

(I)

or a pharmaceutically acceptable salt thereof, wherein $R^A$, $R^B$, $R_2$ and $R_4$ are defined herein. The compounds of formula (I) and pharmaceutically acceptable salts thereof are cationic lipids useful in the delivery of biologically active agents to cells and tissues.

24 Claims, No Drawings
Specification includes a Sequence Listing.

(56) References Cited

OTHER PUBLICATIONS

International Search Report, issued in PCT/US2015/048535, dated Nov. 16, 2015.
International Preliminary Report on Patentability, issued in PCT/US2015/048535, dated Mar. 7, 2017.
Mochizuki et al., "Relationship between DNA-Transfection Efficiency and Chemical Structures of Aromatic Cationic Lipids," Bull. Chem. Soc. Jpn., vol. 85, No. 3, (2012), pp. 354-359.
Egbe et al., "Supramolecular Ordering, Thermal Behavior, and Photophysical, Electrochemical, and Electroluminescent Properties of Alkoxy-Substituted Yne-Containing Poly(phenylene-vinylene)s," Macromolecules, vol. 37, No. 20, (2004), pp. 7451-7463.
Kitada et al., "Soluble-Support-Assisted Electrochemical Reactions: Application to Anodic Disulfide Bond Formation," Organic Letters, vol. 14, No. 23, (2012), pp. 5960-5963.
Kitada et al., "Hydrophobic Tag-Assisted Liquid-Phase Synthesis of a Growth Hormone-Inhibiting Peptide Somatostatin," Bioorganic & Medicinal Chemistry Letters, vol. 21, No. 15, (2011), pp. 4476-4479.
Kitada et al., "Supporting Information Hydrophobic Tag-Assisted Solution-Phase Synthesis of a Growth Hormone-Inhibiting Peptide Somatostatin 4 5," Bioorganic & Medicinal Chemistry Letters, vol. 21, No. 15, (2011), pp. 4476-4479.
Zhang et al., "Interaction of Cholesterol-Conjugated Ionizable Amino Lipids with Biomembranes: Lipid Polymorphism, Structure-Activity Relationship, and Implications for siRNA Delivery," Langmuir, vol. 27, (2011), pp. 9473-9483.
Xu and Szoka, Jr., "Mechanism of DNA Release from Cationic Liposome/DNA complexes Used in Cell Transfection," Biochemistry, vol. 35, (1996), pp. 5616-5623.
Maier et al., "Biodegradable Lipids Enabling Rapidly Eliminated Lipid Nanoparticles for Systemic Delivery of RNAi Therapeutics," American Society of Gene & Cell Therapy, vol. 21, No. 8, (2013), pp. 1570-1578.
Semple et al., "Rational Design of Cationic Lipids for siRNA Delivery," Nature Biotechnology, vol. 28, No. 1, 2010), pp. 172-178.
Leung et al., "Lipid Nanoparticles Containing siRNA Synthesized by Microfluidic Mixing Exhibit an Electron-Dense Nanostructured Core," J. Phys. Chem., vol. 116, (2012), pp. 18440-18450.
Morrissey et al, "Potent and Persistent in vivo Anti-HBV Activity of Chemically Modified siRNAs," Nature Biotechnology, vol. 23, No. 8, (2005), pp. 1002-1007.
Zimmerman et al., "RNAi-Mediated Gene Silencing in Non-Human Primates," Nature, vol. 441, (2006), pp. 111-114.
Jayaraman et al., "Maximizing the Potency of siRNA Lipid Nanoparticles for Hepatic Gene Silencing In Vivo," Agnew. Chem. Int. Ed., vol. 51, (2012), pp. 8529-8533.
Falsini et al., "Advances in Lipid-Based Platforms for RNAi Therapeutics," J. Med. Chem., (2013), pp. A-I.
Felgner et al., "Lipofection: A highly Efficient, Lipid-Mediated DNA-Transfection Procedure," Pro. Natl. Acad. Sci. USA, vol. 84, (1987), pp. 7413-7417.
Felgner, "Particulate Systems and Polymers for in vitro and in vivo Delivery of Polynucleotides," Advanced Drug Delivery Reviews, vol. 5, No. 3, (1990), pp. 163-187.
Felgner, "Cationic Lipid/Polynucleotide Condensates for in vitro and in vivo Polynucleotide Delivery—The Cytofectins," Journal of Liposome Research, vol. 3, No. 1, (1993), pp. 3-16.
Gallas et al., "Chemistry and Formulations of siRNA Therapeutics," Chem. Soc. Rev., vol. 42, (2013), pp. 7983-7997.
Allen and Cullis, "Liposomal Drug Delivery Systems: From Concept to Clinical Applications," Advanced Drug Delivery Reviews, vol. 65, (2013), pp. 36-48.
Akhtar and Juliano, "Cellular Uptake and Intracellular Fate of Antisense Oligonucleotides," Trends in Cell Biology, vol. 2, (1992), pp. 139-144.
Bangham et al., "Diffusion of Univalent Ions Across the Lamellae of Swollen Phospholipids," Journal of Molecular Biology, vol. 13, No. 1, (1965), pp. 238-252.
Brigham et al., "Rapid Communication: In vivo Transfection of Murine Lungs with a Functioning Prokaryotic Gene Using a Liposome Vehicle," The American Journal of the Medical Sciences, vol. 298, No. 4, (1989), pp. 278-281.

* cited by examiner

LIPIDS AND LIPID COMPOSITIONS FOR THE DELIVERY OF ACTIVE AGENTS

RELATED APPLICATIONS

This application is a continuation of U.S. patent application Ser. No. 15/505,282, filed Feb. 21, 2017, which is the U.S. National Phase under 35 U.S.C. § 371 of International Patent Application No. PCT/US2015/048535, filed Sep. 4, 2015, which claims priority to and the benefit of U.S. Provisional Application No. 62/046,487, filed Sep. 5, 2014. The entire disclosures of these applications are hereby incorporated by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "Sequence_Listing" created on Sep. 17, 2018, and is 4,096 bytes in size. The sequence listing contained in this .txt file is part of the specification and is hereby incorporated by reference herein in its entirety.

FIELD OF THE INVENTION

This invention relates to cationic lipid compounds and to compositions comprising such compounds. This invention also relates to processes for making such compounds and compositions, and to methods and uses of such compounds and compositions, e.g., to deliver biologically active agents, such as RNA agents, to cells and tissues.

BACKGROUND OF THE INVENTION

The delivery of biologically active agents (including therapeutically relevant compounds) to subjects is often hindered by difficulties in the compounds reaching the target cell or tissue. In particular, the trafficking of many biologically active agents into living cells is highly restricted by the complex membrane systems of the cells. These restrictions can result in the need to use much higher concentrations of biologically active agents than is desirable to achieve a result, which increases the risk of toxic effects and side effects. One solution to this problem is to utilize specific carrier molecules and carrier compositions which are allowed selective entry into the cell. Lipid carriers, biodegradable polymers and various conjugate systems can be used to improve delivery of biologically active agents to cells.

One class of biologically active agents that is particularly difficult to deliver to cells is a bio therapeutic (including nucleosides, nucleotides, polynucleotides, nucleic acids and derivatives, such as RNA agents). In general, nucleic acids are stable for only a limited duration in cells or plasma. The development of RNA interference, RNAi therapy, mRNA therapy, RNA drugs, antisense therapy, gene therapy and nucleic acid-based vaccines (e.g., RNA vaccines) among others, has increased the need for an effective means of introducing active nucleic acid agents into cells. For these reasons, compositions that can stabilize and deliver nucleic acid-based agents into cells are of particular interest.

The most well-studied approaches for improving the transport of foreign nucleic acids into cells involve the use of viral vectors or formulations with cationic lipids. Viral vectors can be used to transfer genes efficiently into some cell types, but they generally cannot be used to introduce chemically synthesized molecules into cells.

An alternative approach is to use delivery compositions incorporating cationic lipids which interact with a biologically active agent at one part and interact with a membrane system at another part. Such compositions are reported to provide liposomes, miscelles, lipoplexes, or lipid nanoparticles, depending on the composition and method of preparation (for reviews, see Felgner, 1990, Advanced Drug Delivery Reviews, 5, 162-187; Felgner, 1993, J. Liposome Res., 3, 3-16; Gallas, 2013, Chem. Soc. Rev., 42, 7983-7997; Falsini, 2013, J. Med. Chem. dx.doi.org/10.1021/jm400791q; and references therein).

Since the first description of liposomes in 1965 by Bangham (J. Mol. Biol. 13, 238-252), there has been a sustained interest and effort in developing lipid-based carrier systems for the delivery of biologically active agents (Allen, 2013, Advanced Drug Delivery Reviews, 65, 36-48). The process of introducing functional nucleic acids into cultured cells by using positively charged liposomes was first described by Philip Felgner et al. *Proc. Natl. Acad. Sci., USA,* 84, 7413-7417 (1987). The process was later demonstrated in vivo by K. L. Brigham et al., *Am. J. Med. Sci.,* 298, 278-281 (1989). More recently, lipid nanoparticle formulations have been developed with demonstrated efficacy in vitro and in vivo. (Falsini, 2013, J. Med. Chem. dx.doi.org/10.1021/jm400791q; Morrissey, 2005, Nat. Biotech., 23, 1002-1007; Zimmerman, 2006, Nature, 441, 111-114.; Jayaraman, 2012, Angew. Chem. int. Ed., 51, 8529-8533.)

Lipid formulations are attractive carriers since they can protect biological molecules from degradation while improving their cellular uptake. Out of the various classes of lipid formulations, formulations which contain cationic lipids are commonly used for delivering polyanions (e.g. nucleic acids). Such formulations can be formed using cationic lipids alone and optionally including other lipids and amphiphiles such as phosphatidylethanolamine. It is well known in the art that both the composition of the lipid formulation as well as its method of preparation affect the structure and size of the resultant aggregate (Leung, 2012, J. Phys Chem. C, 116, 18440-18450).

The encapsulation of anionic compounds using cationic lipids is essentially quantitative due to electrostatic interaction. In addition, it is believed that the cationic lipids interact with the negatively charged cell membranes initiating cellular membrane transport (Akhtar et al., 1992, Trends Cell Bio., 2, 139; Xu et al., 1996, Biochemistry 35, 5616). Further, it is believed that the molecular shape, conformation, and properties of the cationic lipids provide enhanced delivery efficiency from endosomal compartments to the cytosol (Semple, 2010, Nat. Biotech, 28, 172-176; Zhang, 2011, 27, 9473-9483)

Although the use of cationic lipids for cellular delivery of biologically active agents has been shown to have several advantages, there still remains a need for further cationic lipids that facilitate the systemic and local delivery of biologically active agents such as mRNA and RNAi agents to cells. There is also a need for cationic lipids that, relative to those cationic lipids that are known in the art, improve the systemic and local delivery of biologically active agents to cells. There is a further need for lipid formulations that have optimized physical characteristics for improved systemic and local delivery of biologically active agents to specific organs and to tumors, especially tumors outside the liver.

In addition, there is a need for further cationic lipids that provide decreased toxicity (or improved therapeutic index), relative to those cationic lipids that are known in the art.

Traditional cationic lipids have been employed for RNA and DNA delivery to the liver or tumors but suffer from non-optimal delivery efficiency along with tissue and organ toxicity at higher doses. One method of reducing exposure and increasing biocompatability of cationic lipids is to incorporate chemically or biochemically degradable functionalities, (such as ester, amide, acetal, imine, etc.), which can lead to enhanced in vivo clearance (Maier, 2013, 21, 1570-1578).

SUMMARY OF THE INVENTION

The present invention provides a cationic lipid scaffold that demonstrates enhanced efficacy along with lower toxicity (improved therapeutic index) as a result of lower sustained lipid levels in the relavent tissues, and for local delivery applications (eye, ear, skin, lung); delivery to muscle (i.m.), fat, or sub cutaneous cells (s.c. dosing).

In one aspect, this invention provides for a compound of formula (I):

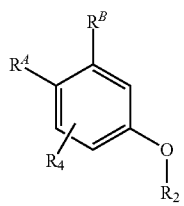

(I)

or a pharmaceutically acceptable salt thereof, wherein $R^A$, $R^B$, $R_2$ and $R_4$ are defined herein. The compounds of formula (I) and pharmaceutically acceptable salts thereof are cationic lipids useful in the delivery of biologically active agents to cells and tissues.

In a second aspect, this invention provides for a lipid composition comprising a compound according to formula (I) (i.e. a lipid composition of the invention), or a pharmaceutically acceptable salt thereof. In one embodiment, the lipid composition further comprises at least one other lipid component. In another embodiment, the lipid composition further comprises a biologically active agent, optionally in combination with on one more other lipid components. In another embodiment the lipid composition is in the form of a liposome. In another embodiment the lipid composition is in the form of a lipid nanoparticle (LNP). In another embodiment the lipid composition is suitable for delivery to the liver. In another embodiment the lipid composition is suitable for delivery to a tumor. In another embodiment the lipid composition is suitable for immunization purposes. In another embodiment the lipid composition is suitable for local delivery applications (eye, ear, skin, lung); delivery to muscle (i.m.), fat, or sub cutaneous cells (s.c. dosing).

In a third aspect, this invention provides for a pharmaceutical composition (i.e. formulation) comprising a lipid composition of the invention and a pharmaceutically acceptable carrier or excipient. In one embodiment, the pharmaceutical composition comprises at least one other lipid component in the lipid composition. In another embodiment the lipid composition is in the form of a liposome. In another embodiment the lipid composition is in the form of a lipid nanoparticle. In another embodiment the lipid composition is suitable for delivery to the liver. In another embodiment the lipid composition is suitable for delivery to a tumor. In another embodiment the lipid composition is suitable for local delivery applications (eye, ear, skin, lung); delivery to muscle (i.m.), fat, or sub cutaneous cells (s.c. dosing). In another embodiment the biologically active agent is an RNA or DNA. In another embodiment the lipid composition is suitable for immunization purposes, and the biologically active agent is a RNA or DNA which encodes an immunogen.

In a fourth aspect, this invention provides a method for the treatment of a disease or condition comprising the step of administering a therapeutically effective amount of a lipid composition of the invention to a patient in need of treatment thereof. In one embodiment, the disease or condition is treatable by administering an RNA or DNA agent. In another embodiment the lipid composition is suitable for immunization purposes, and the biologically active agent is an RNA or DNA which encodes an immunogen.

In a fifth aspect, this invention provides for the use of a lipid composition of the invention in treating a disease or condition in a patient. In one embodiment, the disease or condition is treatable by administering an RNA or DNA agent.

In a sixth aspect, this invention provides a method for inducing an immune response in a subject against an immunogen of interest, comprising administering an immunologically effective amount of a lipid composition of the invention to the subject, in combination with an RNA or DNA which encodes an immunogen.

In a seventh aspect, this invention provides for the use of a lipid composition of the invention in inducing an immune response in a subject against an immunogen of interest. The lipid is used in combination with an RNA or DNA which encodes an immunogen. The invention also provides for the use of a lipid composition of the invention in the manufacture of a medicament for inducing an immune response in a subject against an immunogen of interest.

DETAILED DESCRIPTION OF THE INVENTION

In a first embodiment, the invention is a compound, or salt thereof, of formula (I):

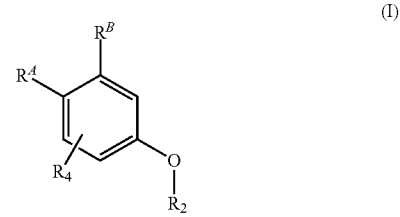

(I)

wherein either one of $R^A$ and $R^B$ is —O—$R_3$ and the other is —$CH_2$—O—C(O)—$R_1$; $R_1$ is $C_{1-6}$-alkylene-NR'R'', $C_{1-6}$-alkoxy-NR'R'', heterocyclyl, heterocyclyl-$C_{1-8}$-alkyl or heterocyclyl-$C_{1-8}$-alkoxyl, each of which may be optionally substituted with 1, 2 or 3 groups, independently selected from halo, $C_{1-8}$-alkyl and $C_{3-7}$-cycloalkyl; R' and R'', are each, independently, hydrogen or —$C_{1-8}$-alkyl; $R_2$ and $R_3$ are each, independently, $C_{12-22}$ alkyl, $C_{12-22}$ alkenyl,

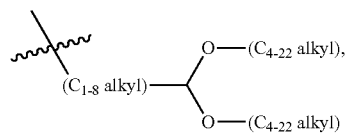

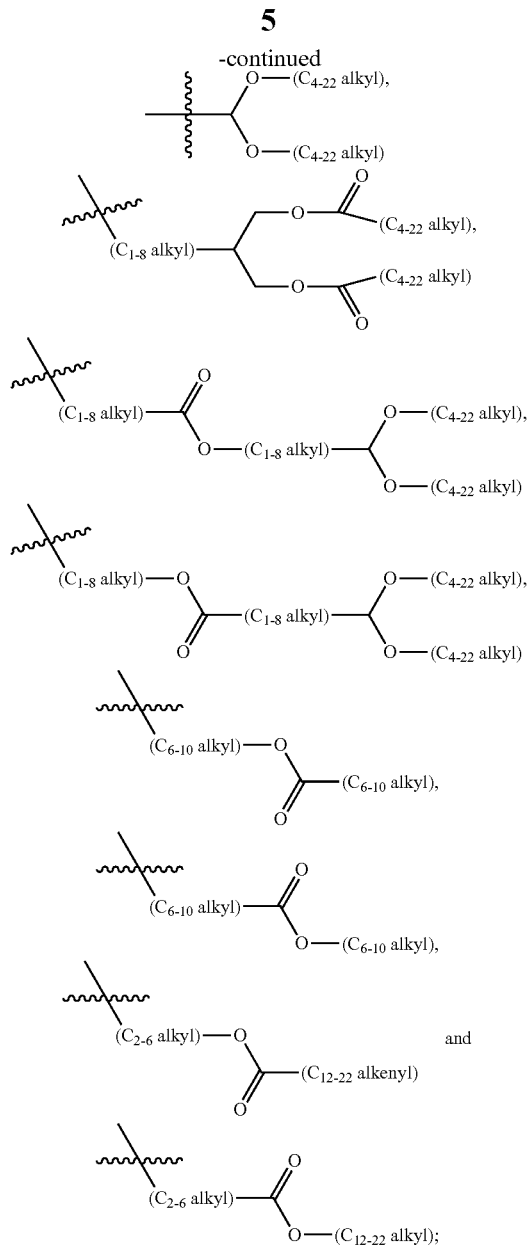

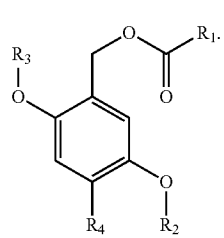

$R_4$ is selected from hydrogen, halo and $C_{1-4}$ alkyl.

In a second embodiment, the invention is the compound, or salt thereof, according to the first embodiment, wherein the compound is of formula (II):

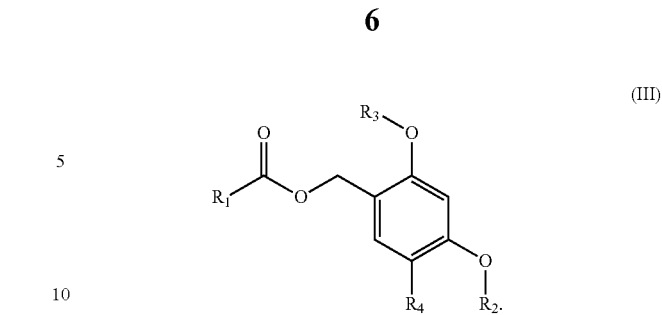

In a third embodiment, the invention is the compound, or salt thereof, according to the first embodiment, wherein the compound is of formula (III):

In a fourth embodiment, the invention is the compound, or salt thereof, according to any one of the first through third embodiments, wherein $R_4$ is hydrogen.

In a fifth embodiment, the invention id the compound, or salt thereof, according to any one of the first through fourth embodiments, wherein $R_1$ is selected from:

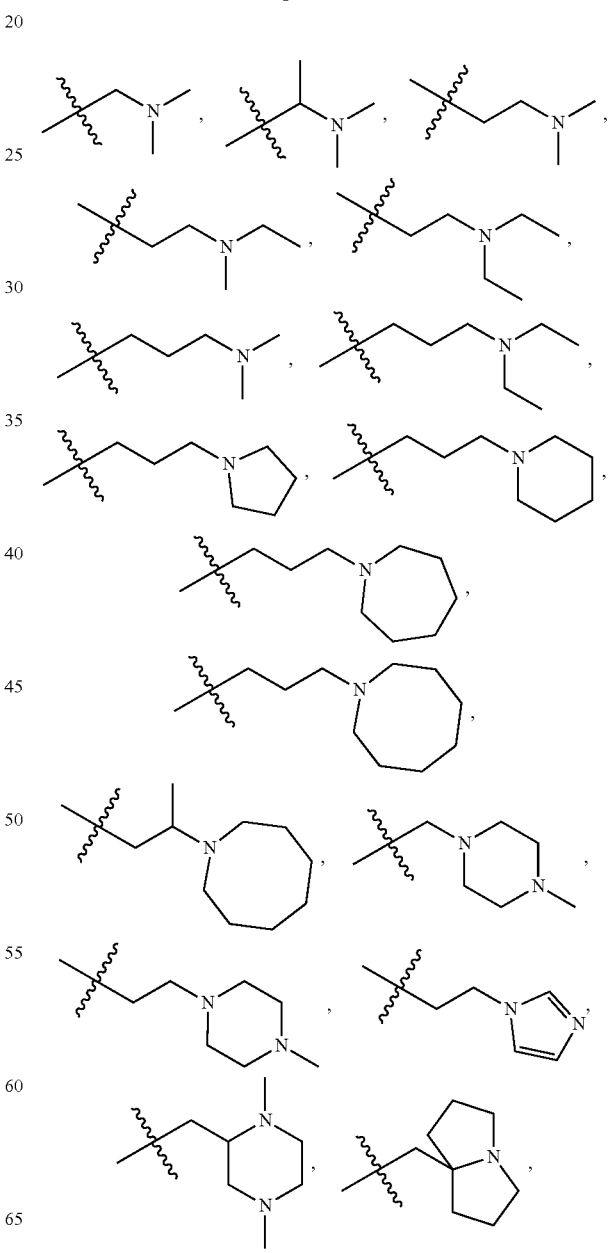

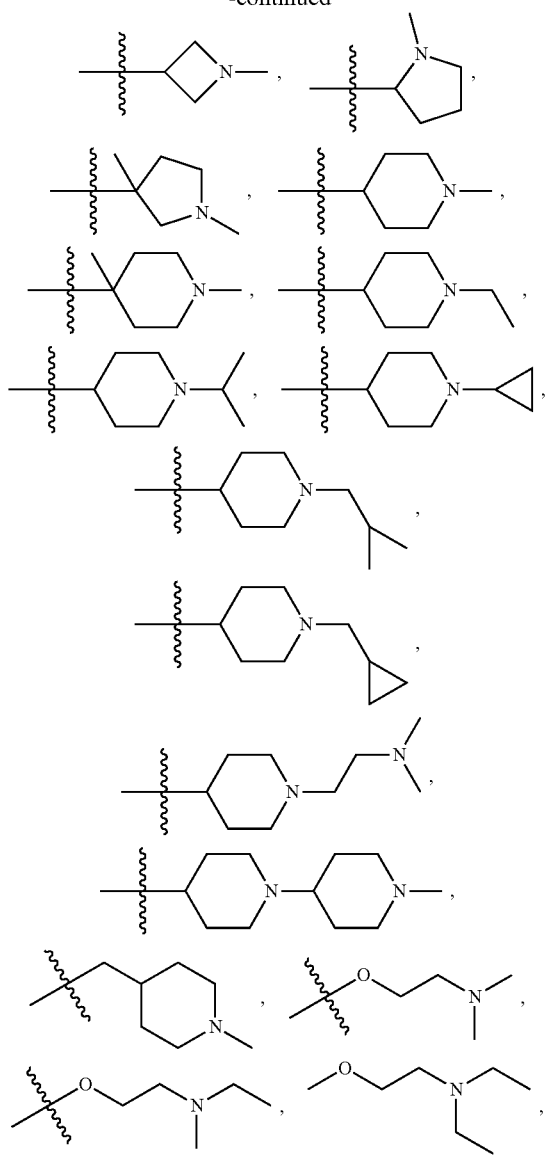
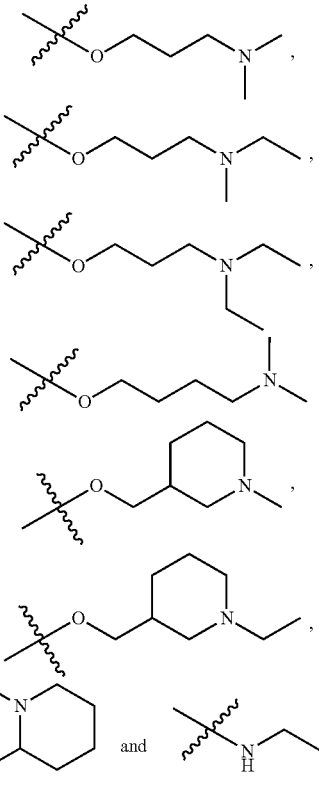
In a sixth embodiment, the invention is the compound, or salt thereof, according to any one of the first through fifth embodiments wherein $R_1$ is
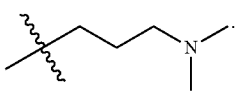 [SMILES: *CCCN(C)C]
In a seventh embodiment, the invention is the compound, or salt thereof, according to any one of the first through sixth embodiments, wherein $R_2$ is selected from:
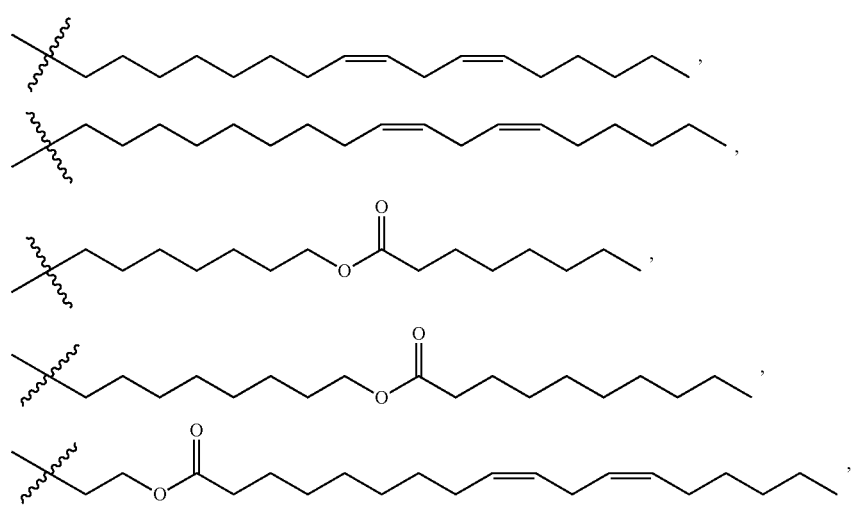

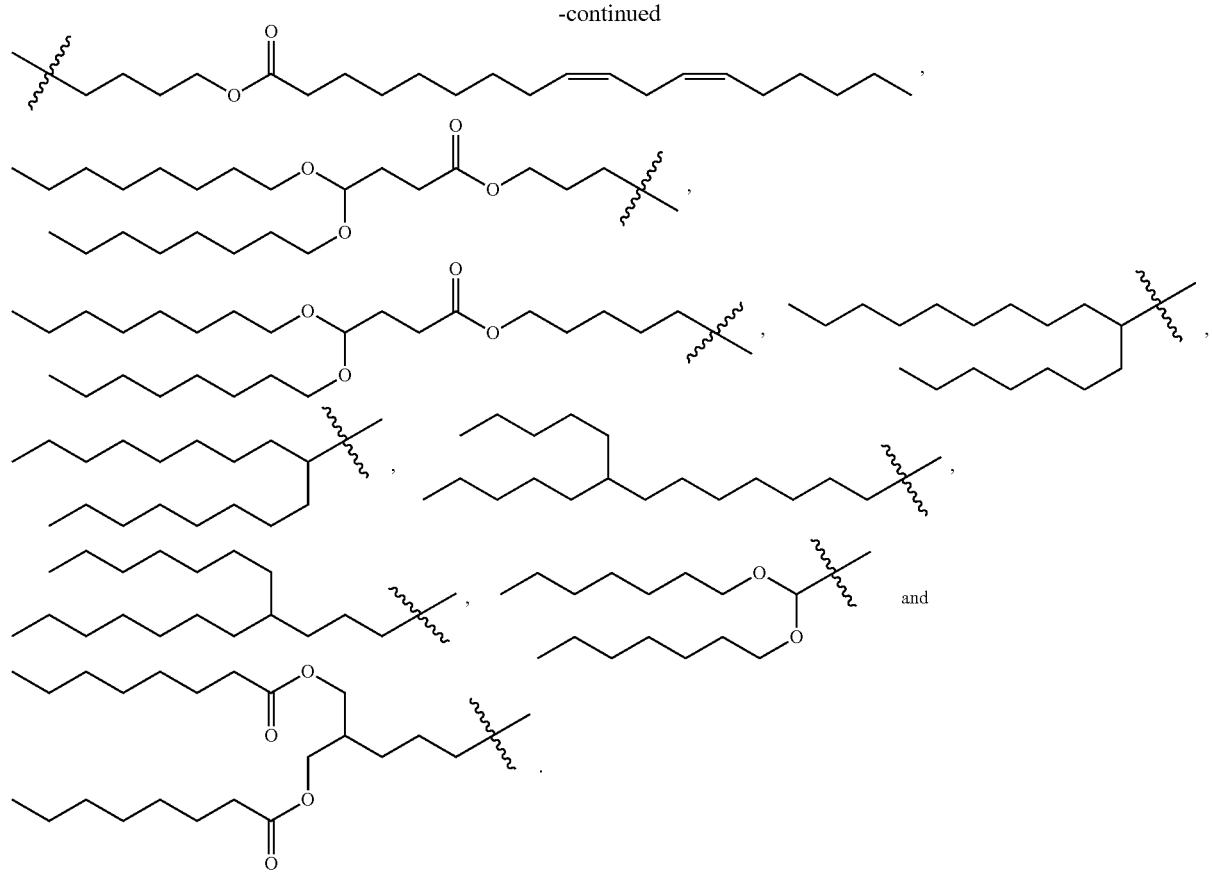
In an eighth embodiment, the invention is the compound, or salt thereof, according to any one of the first through seventh embodiments, wherein $R_2$ is selected from:
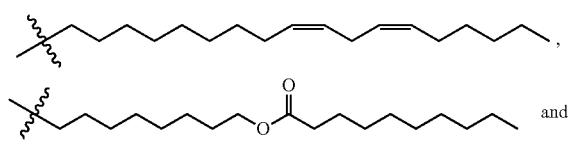
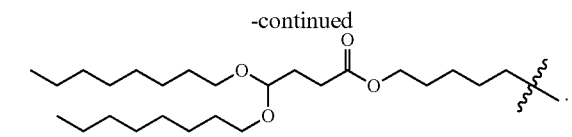
In a ninth embodiment, the invention is the compound, or salt thereof, according to any one of first through eighth embodiments, wherein $R_3$ is selected from
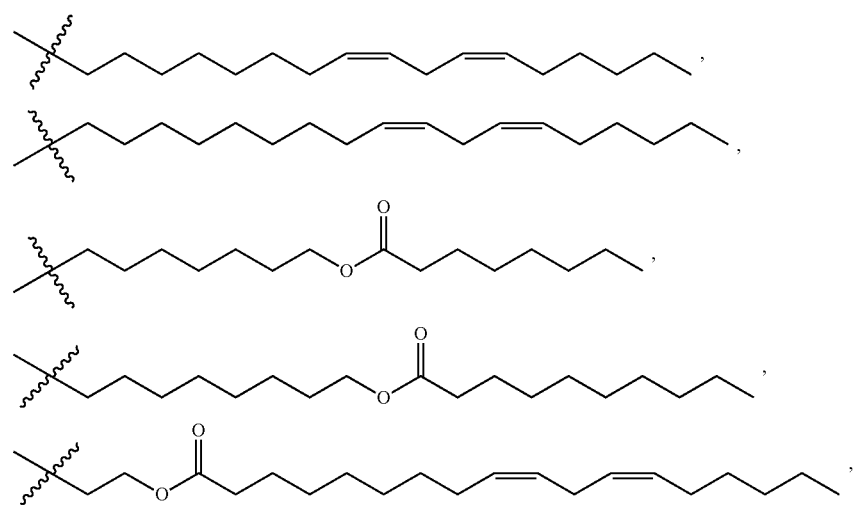

-continued

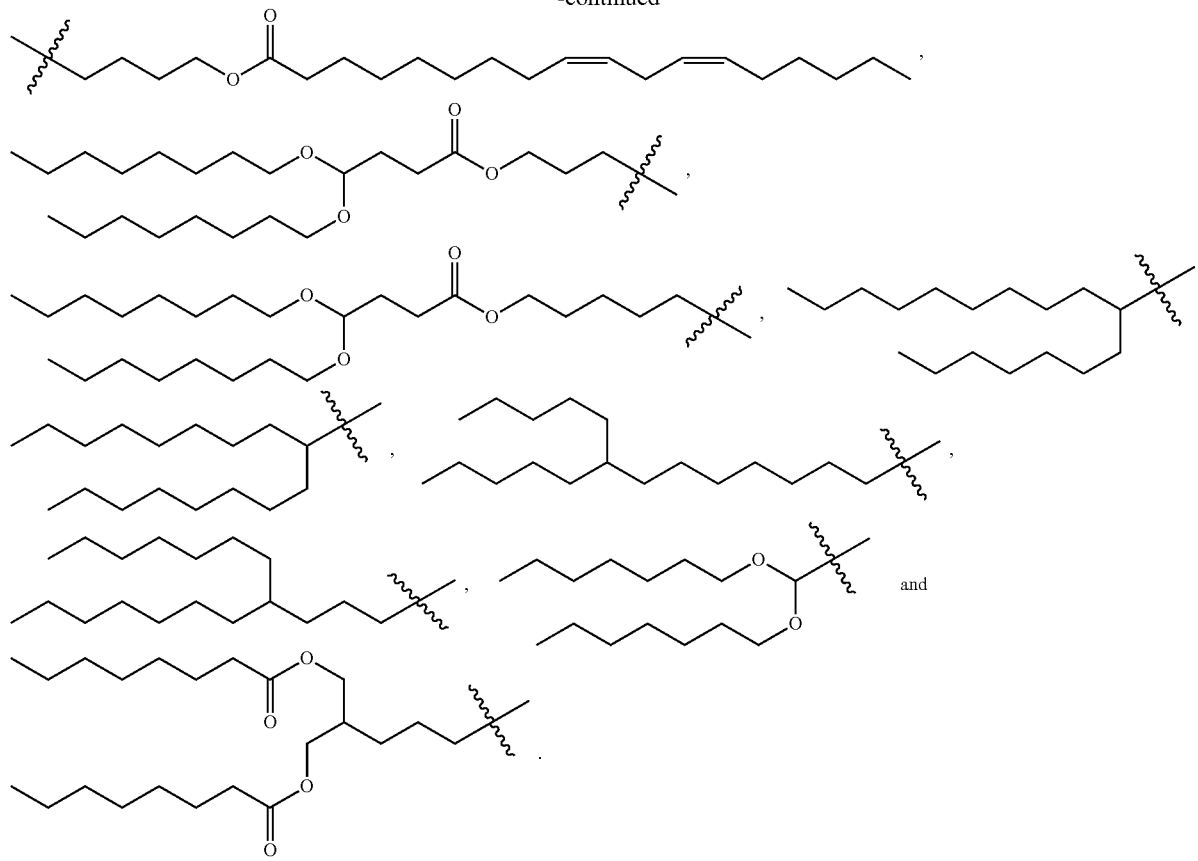

In a tenth embodiment, the invention is the compound, or salt thereof, according to any one of the first through ninth embodiments, wherein $R_3$ is selected from:

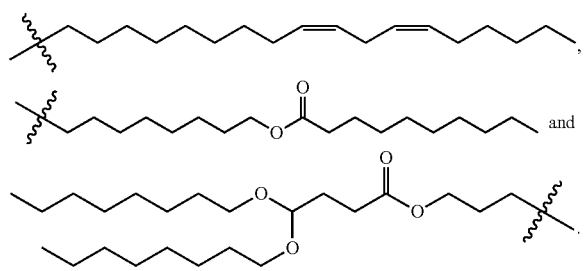

In another embodiment, the invention is the compound, or salt thereof, according to any one of the first through tenth embodiments, wherein $R_2$ and $R_3$ are identical.

In an eleventh embodiment, the invention is the compound, or salt thereof, according to any one of the first through tenth embodiments, wherein the compound is selected from the group consisting of:
2,5-bis((9Z,12Z)-octadeca-9,12-dien-1-yloxy)benzyl 4-(dimethylamino)butanoate;
((2-(((4-(dimethylamino)butanoyl)oxy)methyl)-1,4-phenylene)bis(oxy))bis(octane-8,1-diyl) bis(decanoate);
((2-(((3-(dimethylamino)propanoyl)oxy)methyl)-1,4-phenylene)bis(oxy))bis(octane-8,1-diyl) bis(decanoate);
((2-(((1-methylpiperidine-4-carbonyl)oxy)methyl)-1,4-phenylene)bis(oxy))bis(octane-8,1-diyl) bis(decanoate);
((2-((((3-(dimethylamino)propoxy)carbonyl)oxy)methyl)-1,4-phenylene)bis(oxy))bis(octane-8,1-diyl) bis(decanoate);
((2-((((3-(diethylamino)propoxy)carbonyl)oxy)methyl)-1,4-phenylene)bis(oxy))bis(octane-8,1-diyl) bis(decanoate);
3-(dimethylamino) propyl 4-methyl-2,5-bis((9Z,12Z)-octadeca-9,12-dien-1-yloxy)benzyl carbonate;
4-methyl-2,5-bis((9Z,12Z)-octadeca-9,12-dien-1-yloxy) benzyl 4-(dimethylamino)butanoate; (9Z,9'Z,12Z,12'Z)-((2-(((4-(dimethylamino)butanoyl)oxy)methyl)-1,4-phenylene)bis(oxy))bis(butane-4,1-diyl) bis(octadeca-9,12-dienoate);
4-(dimethylamino) butyl 4-methyl-2,5-bis((9Z,12Z)-octadeca-9,12-dien-1-yloxy)benzyl carbonate;
((2-(((1-ethylpiperidine-4-carbonyl)oxy)methyl)-1,4-phenylene)bis(oxy))bis(octane-8,1-diyl) bis(decanoate);
((2-(((1-isopropylpiperidine-4-carbonyl)oxy)methyl)-1,4-phenylene)bis(oxy))bis(octane-8,1-diyl) bis(decanoate);
((2-((2-(1-methylpiperidin-4-yl)acetoxy)methyl)-1,4-phenylene)bis(oxy))bis(octane-8,1-diyl) bis(decanoate);
((2-(((4-(pyrrolidin-1-yl)butanoyl)oxy)methyl)-1,4-phenylene)bis(oxy))bis(octane-8,1-diyl) bis(decanoate);
2,5-bis((9Z,12Z)-octadeca-9,12-dien-1-yloxy)benzyl (3-(dimethylamino)propyl) carbonate;
(9Z,9'Z,12Z,12'Z)-((2-(((4-(dimethylamino)butanoyl)oxy)methyl)-1,4-phenylene)bis(oxy))bis(ethane-2,1-diyl) bis(octadeca-9,12-dienoate);
2,5-bis((9Z,12Z)-octadeca-9,12-dien-1-yloxy)benzyl 3-(dimethylamino)propanoate;
2,5-bis((9Z,12Z)-octadeca-9,12-dien-1-yloxy)benzyl (3-(diethylamino)propyl) carbonate;

((4-(((4-(dimethylamino)butanoyl)oxy)methyl)-1,3-phenylene)bis(oxy))bis(octane-8,1-diyl) bis(decanoate);
((4-(((4-(diethylamino)butanoyl)oxy)methyl)-1,3-phenylene)bis(oxy))bis(octane-8,1-diyl) bis(decanoate);
((2-(((4-(diethylamino)butanoyl)oxy)methyl)-1,4-phenylene)bis(oxy))bis(pentane-5,1-diyl) bis(4,4-bis(octyloxy)butanoate);
8-(4-((5-((4,4-bis(octyloxy)butanoyl)oxy)pentyl)oxy)-3-(((4-(dimethylamino)butanoyl)oxy)methyl)phenoxy)octyl decanoate;
8-(4-((5-((4,4-bis(octyloxy)butanoyl)oxy)pentyl)oxy)-2-(((4-(dimethylamino)butanoyl)oxy)methyl)phenoxy)octyl decanoate;
((2-(((4-(dimethylamino)butanoyl)oxy)methyl)-1,4-phenylene)bis(oxy))bis(propane-3,1-diyl) bis(4,4-bis(octyloxy)butanoate);
((4-(((1,4-dimethylpiperidine-4-carbonyl)oxy)methyl)-1,3-phenylene)bis(oxy))bis(octane-8,1-diyl) bis(decanoate);
((2-(((4-(dimethylamino)butanoyl)oxy)methyl)-1,4-phenylene)bis(oxy))bis(pentane-5,1-diyl) bis(4,4-bis(octyloxy)butanoate);
((2-(((1,4-dimethylpiperidine-4-carbonyl)oxy)methyl)-1,4-phenylene)bis(oxy))bis(pentane-5,1-diyl) bis(4,4-bis(octyloxy)butanoate); and
2,4-bis((9Z,12Z)-octadeca-9,12-dien-1-yloxy)benzyl 4-(dimethylamino)butanoate.

In a twelfth embodiment, the invention is a lipid composition comprising a compound according to any one of the first through eleventh embodiments, or a pharmaceutically acceptable salt thereof.

In a thirteenth embodiment, the invention is the lipid composition according to the twelfth embodiment, further comprising a biologically active agent.

In a fourteenth embodiment, the invention is the lipid composition according to the thirteenth embodiment wherein, the biologically active agent is a nucleic acid.

In a fifteenth embodiment, the invention is the lipid composition according to any one of the thirteenth through fourteenth embodiments, wherein the biologically active agent is a DNA, siRNA or mRNA.

In a sixteenth embodiment, the invention is the lipid composition according to any one of the thirteenth through fifteenth embodiments, wherein the biologically active agent is an mRNA.

In a seventeenth embodiment, the invention is the lipid composition according to any one of the thirteenth through fifteenth embodiments, wherein the biologically active agent is a siRNA.

In an eighteenth embodiment, the invention is the lipid composition according to any one of the twelfth through seventeenth embodiments, further comprising a helper lipid.

In a nineteenth embodiment, the invention is the lipid composition according to any one of the twelfth through eighteenth embodiments, further comprising a neutral lipid.

In a twentieth embodiment, the invention is the lipid composition according to any one of Twelfth through nineteenth embodiments, further comprising a stealth lipid.

In a twenty-first embodiment, the invention is the lipid composition according to any one of the twelfth through twentieth embodiments, wherein the helper lipid is cholesterol, the neutral lipid is DSPC, and the stealth lipid is S010, S024, S027, S031, or S033.

In a twenty-second embodiment, the invention is the lipid composition according to any one of the twelfth through twenty-first embodiments, wherein the lipid composition is in the form of a lipid nanoparticle.

In a twenty-third embodiment, the invention is the lipid composition according to any one of the twelfth through twenty-second embodiments, having 30-60% of a compound of formula (I), 5-10% cholesterol/30-60% DSPC, and 0.1-5% S010, S024, S027, S031, or S033.

In a twenty-fourth embodiment, the invention is the lipid composition according to any one of the twelfth through twenty-third embodiments, wherein the pH of said lipid composition is 4-8 at the time of encapsulation and/or formulation.

In a twenty-fifth embodiment, the invention is the lipid composition according to any one of the twelfth through twenty-fourth embodiments, wherein the pH of said lipid composition is 5-7 at the time of encapsulation and/or formulation.

In a twenty-sixth embodiment, the invention is the lipid composition according to any one of the twelfth through twenty-fifth embodiments, wherein the pH of said lipid composition is 5.9-6.5 at the time of encapsulation and/or formulation.

In one embodiment, the invention is the lipid composition according to any one of the twelfth through twenty-fifth embodiments, wherein the pH of said lipid composition is 5.9 at the time of encapsulation and/or formulation.

In another embodiment, the invention is the lipid composition according to any one of the twelfth through twenty-fifth embodiments, wherein the pH of said lipid composition is 6.0 at the time of encapsulation and/or formulation.

In yet another embodiment, the invention is the lipid composition according to any one of the twelfth through twenty-fifth embodiments, wherein the pH of said lipid composition is 6.1 at the time of encapsulation and/or formulation.

In another embodiment, the invention is the lipid composition according to any one of the twelfth through twenty-fifth embodiments, wherein the pH of said lipid composition is 6.2 at the time of encapsulation and/or formulation.

In yet another embodiment, the invention is the lipid composition according to any one of the twelfth through twenty-fifth embodiments, wherein the pH of said lipid composition is 6.3 at the time of encapsulation and/or formulation.

In another embodiment, the invention is the lipid composition according to any one of the twelfth through twenty-fifth embodiments, wherein the pH of said lipid composition is 6.4 at the time of encapsulation and/or formulation.

In yet another embodiment, the invention is the lipid composition according to any one of the twelfth through twenty-fifth embodiments, wherein the pH of said lipid composition is 6.5 at the time of encapsulation and/or formulation.

In a twenty-seventh embodiment, the invention is a pharmaceutical composition comprising a lipid composition according to any one of the twelfth through twenty-sixth embodiments, and a pharmaceutically acceptable carrier or excipient.

In a twenty-eighth embodiment, the invention is a method for the treatment of a disease or condition comprising the step of administering a therapeutically effective amount of lipid composition according to any one of the twelfth through twenty-seventh embodiments, to a patient in need of treatment thereof.

In a twenty-ninth embodiment, the invention provides a liposome comprising the compound of any one of embodiments 1-11, wherein said liposome encapsulates an RNA molecule that encodes an immunogen.

In a thirtieth embodiment, the invention provides a lipid nanoparticle (LNP) comprising the compound of any one of embodiments 1-11, wherein said LNP (i) encapsulates an RNA molecule that encodes an immunogen, or (ii) is complexed with an RNA molecule that encodes an immunogen.

In a thirty-first embodiment, the invention provides a liposome of embodiment 29, or the LNP of embodiment 30, wherein the liposome has a diameter in the range of 80-160 nm.

In a thirty-second embodiment, the invention provides a liposome or LNP of any one of embodiments 29-31, wherein said liposome further comprises a lipid comprising a zwitterionic head group.

In a thirty-third embodiment, the invention provides a liposome or LNP of any one of embodiments 29-32, wherein said liposome further comprises DlinDMA (1,2-dilinoleyloxy-N,N-dimethyl-3-aminopropane), DSPC (1,2-Diastearoyl-sn-glycero-3-phosphocholine), a cholesterol, a PEGylated lipid, or a combination thereof.

In a thirty-fourth embodiment, the invention provides a pharmaceutical composition comprising the liposome or LNP of any one of embodiments 29-33.

In a thirty-fifth embodiment, the invention provides a pharmaceutical composition comprising a population of liposomes and a population of immunogen-encoding RNA molecules, wherein the liposomes comprise the compound of any one of embodiments 1-11, and wherein at least half of the population of the RNA molecules are encapsulated in liposomes.

In a thirty-sixth embodiment, the invention provides a pharmaceutical composition comprising a population of nanoparticles (LNPs) and a population of immunogen-encoding RNA molecules, wherein the LNPs comprise the compound of any one of claims 1-11, and wherein at least half of the population of the RNA molecules are (i) encapsulated in LNPs; or (ii) complexed with LNPs.

In a thirty-seventh embodiment, the invention provides a pharmaceutical composition of embodiment 35 or 36, wherein (i) at least 80% by number of the liposomes or LNPs have diameters in the range of 60-180 nm, (ii) the average diameter of the population is in the range of 60-180 nm, or (iii) the diameters of the liposomes or LNPs have a polydispersity index <0.2.

In a thirty-eighth embodiment, the invention provides a pharmaceutical composition comprising (i) a compound according to any one of claims 1-11, or a pharmaceutically acceptable salt thereof; (ii) an RNA molecule that encodes an immunogen.

In yet another embodiment, the invention provides a pharmaceutical composition of embodiment 38, further comprising a lipid comprising a zwitterionic head group.

In yet another embodiment, the invention provides a pharmaceutical composition of embodiment 38, further comprising DlinDMA (1,2-dilinoleyloxy-N,N-dimethyl-3-aminopropane), DSPC (1,2-Diastearoyl-sn-glycero-3-phosphocholine), a cholesterol, a PEGylated lipid, or a combination thereof.

In a thirty-ninth embodiment, the invention provides a liposome or LNP of any one of embodiments 29-33, or the pharmaceutical composition of any one of embodiments 34-38, wherein the RNA is a self-replicating RNA.

In a fortieth embodiment, the invention provides a liposome, LNP, or pharmaceutical composition of embodiment 39, wherein the self-replicating RNA encodes a RNA-dependent RNA polymerase.

In a forty-first embodiment, the invention provides a liposome, LNP, or pharmaceutical composition of embodiment 39 or 40, wherein the self-replicating RNA comprises two open reading frames, the first of which encodes an alphavirus replicase and the second of which encodes the immunogen.

In a forty-second embodiment, the invention provides a liposome, LNP, or pharmaceutical composition of any one of embodiments 39-41, wherein the self-replicating RNA is 9000-12000 nucleotides long.

In a forty-third embodiment, the invention provides a liposome, LNP, or pharmaceutical composition of any one of embodiments 29-42, wherein the immunogen can elicit an immune response in vivo against a bacterium, a virus, a fungus or a parasite.

In a forty-fourth embodiment, the invention provides a method for inducing an immune response in a vertebrate, comprising administering to said vertebrate an effective amount of the liposome, LNP, or pharmaceutical composition of any one of embodiments 29-43.

As used herein, the term "alkyl" refers to a fully saturated branched or unbranched hydrocarbon chain having the specified number of carbon atoms. For example, $C_{1-6}$ alkyl refers to an alkyl group having from 1 to 6 carbon atoms. For example, $C_{2-6}$ alkyl refers to an alkyl group having from 2 to 6 carbon atoms. For example, $C_{1-8}$ alkyl refers to an alkyl group having from 1 to 8 carbon atoms. For example, $C_{4-22}$ alkyl refers to an alkyl group having from 4 to 22 carbon atoms. For example, $C_{6-10}$ alkyl refers to an alkyl group having from 6 to 10 carbon atoms. For example, $C_{12-22}$ alkyl refers to an alkyl group having from 12 to 22 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecanyl, n-dodecanyl, n-tridecanyl, 9-methylheptadecanyl, 1-heptyldecyl, 2-octyldecyl, 6-hexyldodecyl, 4-heptylundecyl, and the like.

As used herein, the term "alkylene" refers to divalent alkyl group as defined herein above. Representative examples of alkylene include, but are not limited to, methylene, ethylene, n-propylene, iso-propylene, n-butylene, sec-butylene, iso-butylene, tert-butylene, n-pentylene, iso-pentylene, neopentylene, n-hexylene, 3-methylhexylene, 2,2-dimethylpentylene, 2,3-dimethylpentylene, n-heptylene, n-octylene, n-nonylene, n-decylene, and the like. For example, $C_{1-6}$ alkylene refers to an alkylene group having from 1 to 6 carbon atoms.

As used herein, the term "alkenyl" refers to an unsaturated branched or unbranched hydrocarbon chain having the specified number of carbon atoms and one or more carbon-carbon double bonds within the chain. For example, $C_{12-22}$ alkenyl refers to an alkenyl group having 12 to 22 carbon atoms with one or more carbon-carbon double bonds within the chain. In certain embodiments alkenyl groups have one carbon-carbon double bond within the chain. In other embodiments, alkenyl groups have more than one carbon-carbon double bond within the chain. Alkyenyl groups may be optionally substituted with one or more substituents as defined in formula (I). Representative examples of alkenyl include, but are not limited to, ethylenyl, propenyl, butenyl, pentenyl, hexenyl and the like. Other examples of alkenyl include, but are not limited to: Z-octadec-9-enyl, Z-undec-7-enyl, Z-heptadeca-8-enyl, (9Z,12Z)-octadeca-9,12-dienyl, (8Z,11Z)-heptadeca-8,11-dienyl, (8Z, 11Z, 14Z)-heptadeca-8,11,14-trienyl, linolenyl, 2-octyldeca-1-enyl, linoleyl and olelyl.

As used herein, the term "alkoxy" refers to refers to any alkyl moiety attached through an oxygen bridge (i.e. a —O—C$_{1-3}$ alkyl group wherein C$_{1-3}$ alkyl is as defined herein). Examples of such groups include, but are not limited to, methoxy, ethoxy, and propoxy. For example, C$_{1-6}$ alkoxy refers to an alkoxy group having from 1 to 6 carbon atoms. As used herein, the term "cycloalkyl" refers to a saturated monocyclic, bicyclic or tricyclic hydrocarbon ring having the specified number of carbon atoms. For example, C$_{3-7}$ cycloalkyl refers to a cycloalkyl ring having from 3 to 7 carbon atoms. Cycloalkyl groups may be optionally substituted with one or more substituents as defined in formula (I). Representative examples of cycloalkyl include, but are not limited to, cyclopropyl, cyclobutyl, cyclopentyl, cyclohexyl, bicyclo[2.1.1]hexyl, bicyclo[2.2.1]heptyl, adamantyl and the like.

As used herein, the term "halo" refers to fluoro, chloro, bromo, and iodo.

As used herein, the term "heterocyclic" refers to a 4 to 12 membered saturated or unsaturated monocyclic or bicyclic ring containing from 1 to 4 heteroatoms. Heterocyclic ring systems are not aromatic. Heterocyclic groups containing more than one heteroatom may contain different heteroatoms. Heterocyclic groups are monocyclic, spiro, or fused or bridged bicyclic ring systems. Examples of monocyclic heterocyclic groups include tetrahydrofuranyl, dihydrofuranyl, 1,4-dioxanyl, morpholinyl, 1,4-dithianyl, azetidinyl, piperazinyl, piperidinyl, 1,3-dioxolanyl, imidazolidinyl, imidazolinyl, pyrrolinyl, pyrrolidinyl, tetrahydropyranyl, dihydropyranyl, 1,2,3,6-tetrahydropyridinyl, oxathiolanyl, dithiolanyl, 1,3-dioxanyl, 1,3-dithianyl, oxathianyl, thiomorpholinyl, 1,4,7-trioxa-10-azacyclododecanyl, azapanyl and the like. Examples of spiro heterocyclic rings include, but are not limited to, 1,5-dioxa-9-azaspiro[5.5]undecanyl, 1,4-dioxa-8-azaspiro[4.5]decanyl, 2-oxa-7-azaspiro[3.5] nonanyl, and the like. Fused heterocyclic ring systems have from 8 to 11 ring atoms and include groups wherein a heterocyclic ring is fused to a phenyl ring. Examples of fused heterocyclic rings include, but are not limited to decahydroqunilinyl, (4aS, 8aR)-decahydroisoquinolinyl, (4aS,8aS)-decahydroisoquinolinyl, octahydrocyclopenta[c] pyrrolyl, isoinolinyl, (3aR,7aS)-hexahydro-[1,3]dioxolo [4.5-c]pyridinyl, octahydro-1H-pyrrolo[3,4-b]pyridinyl, tetrahydroisoquinolinyl and the like.

As used herein, the term "heterocyclylC$_{1-8}$alkyl" refers to a heterocyclic ring as defined above which is attached to the rest of the molecule by a single bond or by a C$_{1-8}$alkyl radical as defined above.

As used herein, the term "heterocyclylC$_{1-8}$alkoxy" refers to a heterocyclic ring as defined above which is attached to the rest of the molecule by a single bond or by a C$_{1-8}$alkoxy radical as defined above.

As used herein, the term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)— or (S)—.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)— and (S)— isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)—, (S)— or (R,S)— configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)— or (S)— configuration. Substituents at atoms with unsaturated double bonds may, if possible, be present in cis-(Z)— or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the terms "salt" or "salts" refers to an acid addition of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Lipid Compositions

The present invention provides for a lipid composition comprising at least one compound of formula (I), i.e. a lipid composition of the invention. In one embodiment, at least one other lipid component is present. Such compositions can also contain a biologically active agent, optionally in combination with one or more other lipid components.

One embodiment of the present invention provides for a lipid composition comprising a compound of formula (I) and another lipid component. Such other lipid components include, but are not limited to, cationic lipids, neutral lipids, anionic lipids, helper lipids, and stealth lipids.

Cationic lipids suitable for use in a lipid composition of the invention include, but are not limited to, N,N-dioleyl-N,N-dimethylammonium chloride (DODAC), N,N-distearyl-N,N-dimethylammonium bromide (DDAB), N-(1-(2,3-dioleoyloxy) propyl)-N,N,N-trimethylammonium chloride (DOTAP), 1,2-Dioleoyl-3-Dimethylammonium-propane (DODAP), N-(1-(2,3-dioleyloxy)propyl)-N,N,N-trimethylammonium chloride (DOTMA), 1,2-Dioleoylcarbamyl-3-Dimethylammonium-propane (DOCDAP), 1,2-Dilineoyl-3-Dimethylammonium-propane (DLINDAP), dilauryl($C_{12:0}$) trimethyl ammonium propane (DLTAP), Dioctadecylamidoglycyl spermine (DOGS), DC-Chol, Dioleoyloxy-N-[2-sperminecarboxamido)ethyl}-N,N-dimethyl-1-propanaminiumtrifluoroacetate (DOSPA), 1,2-Dimyristyloxypropyl-3-dimethyl-hydroxyethyl ammonium bromide (DMRIE), 3-Dimethylamino-2-(Cholest-5-en-3-beta-oxybutan-4-oxy)-1-(cis,cis-9,12-octadecadienoxy)propane (CLinDMA), N,N-dimethyl-2,3-dioleyloxy)propylamine (DODMA), 2-[5'-(cholest-5-en-3[beta]-oxy)-3'-oxapentoxy)-3-dimethyl-1-(cis,cis-9',12'-octadecadienoxy) propane (CpLinDMA) and N,N-Dimethyl-3,4-dioleyloxybenzylamine (DMOBA), and 1,2-N,N'-Dioleylcarbamyl-3-dimethylaminopropane (DOcarbDAP). In one embodiment the cationic lipid is DOTAP or DLTAP.

Neutral lipids suitable for use in a lipid composition of the invention include, for example, a variety of neutral, uncharged or zwitterionic lipids. Examples of neutral phospholipids suitable for use in the present invention include, but are not limited to: 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphophatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In one embodiment, the neutral phospholipid is selected from the group consisting of distearoylphosphatidylcholine (DSPC) and dimyristoyl phosphatidyl ethanolamine (DMPE).

Anionic lipids suitable for use in the present invention include, but are not limited to, phosphatidylglycerol, cardiolipin, diacylphosphatidylserine, diacylphosphatidic acid, N-dodecanoyl phosphatidyl ethanoloamine, N-succinyl phosphatidylethanolamine, N-glutaryl phosphatidylethanolamine cholesterol hemisuccinate (CHEMS), and lysylphosphatidylglycerol.

Suitable neutral and anionic lipids also include those described in US 2009/0048197.

Helper lipids are lipids that enhance transfection (e.g. transfection of the nanoparticle including the biologically active agent) to some extent. The mechanism by which the helper lipid enhances transfection may include, e.g., enhancing particle stability and/or enhancing membrane fusogenicity. Helper lipids include steroids and alkyl resorcinols. Helper lipids suitable for use in the present invention include, but are not limited to, cholesterol, 5-heptadecylresorcinol, and cholesterol hemisuccinate.

Stealth lipids are lipids that increase the length of time for which the nanoparticles can exist in vivo (e.g. in the blood). Stealth lipids suitable for use in a lipid composition of the invention include, but are not limited to, stealth lipids having a hydrophilic head group linked to a lipid moiety. Examples of such stealth lipids include compounds of formula (XI), as described in WO2011/076807,

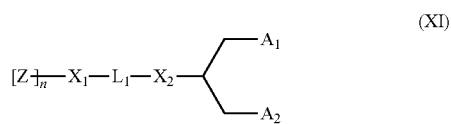

or a salt or pharmaceutically acceptable derivative thereof, wherein:

[Z]n is a hydrophilic polymer moiety selected from PEG (poly(ethylene oxide)), or polymers based on poly(oxazoline), poly(vinyl alcohol), poly(glycerol), poly(N-vinylpyrro-lidone), poly[N-(2-hydroxypropyl)methacrylamide], polysaccharides and poly(amino acid)s, or a combination of any one of the foregoing, wherein the polymer may be linear or branched, and wherein each Z is independently optionally substituted;

wherein Z is polymerized by n subunits;

n is a number-averaged degree of polymerization between 10 and 200 units of Z, wherein n is optimized for different polymer types;

$L_1$ is an optionally substituted $C_{1-10}$ alkylene or $C_{1-10}$ heteroalkylene linker including zero, one, two or more of an ether (e.g., —O—), ester (e.g., —C(O))—), succinate (e.g., —O(O)C—$CH_2$—$CH_2$—C(O)O—)), carbamate (e.g., —OC(O)—NR'—), carbonate (e.g., —OC(O)O—), ketone (e.g., —C—C(O)—C—), carbonyl (e.g., —C(O)—), urea (e.g., —NRC(O)NR'—), amine (e.g., —NR'—), amide (e.g., —C(O)NR'—), imine (e.g., —C(NR')—), thioether (e.g., —S—), xanthate (e.g., —OC(S)S—), and phosphodiester (e.g., —OP(O)$_2$IO—); any of which may be substituted by zero, one or more Z groups;

wherein R' is independently selected from —H, —NH—, —$NH_2$, —O—, —S—, a phosphate or an optionally substituted $C_{1-10}$ alkylene;

$X_1$ and $X_2$ are independently selected from a carbon or a heteroatom selected from —NH—, —O—, —S— or a phosphate;

$A_1$ and $A_2$ are independently selected from a $C_{6-30}$ alkyl, $C_{6-30}$ alkenyl, and $C_{6-30}$ alkynyl, wherein $A_1$ and $A_2$ may be the same or different, or wherein $A_1$ and $A_2$ together with the carbon atom to which they are attached form an optionally substituted steroid.

Specific stealth lipids include, but are not limited to, those listed in Table 1.

TABLE 1

| Stealth Lipids |
|---|
| Stealth Lipid    Lipid |

S001

S002

TABLE 1-continued

Stealth Lipids

| Stealth Lipid | Lipid |
|---|---|
| S003 | |
| S004 | |
| S005 | |
| S006 | |
| S007 | |
| S008 | |
| S009 | |
| S010 | |
| S011 | |

TABLE 1-continued

Stealth Lipids

| Stealth Lipid | Lipid |
|---|---|
| S012 | |
| S013 | |
| S014 | |
| S015 | |
| S016 | |
| S017 | |
| S018 | |
| S019 | |
| S020 | |
| S021 | |

TABLE 1-continued

Stealth Lipids

| Stealth Lipid | Lipid |
|---|---|
| S022 | (chemical structure) |
| S023 | (chemical structure) |
| S024 | (chemical structure) |
| S025 | (chemical structure) |
| S026 | (chemical structure) |
| S027 | (chemical structure) |
| S028 | (chemical structure) |
| S029 | (chemical structure) |
| S030 | (chemical structure) |

TABLE 1-continued

Stealth Lipids

| Stealth Lipid | Lipid |
|---|---|
| S031 | |
| S032 | |
| S033 | |

Other stealth lipids suitable for use in a lipid composition of the present invention and information about the biochemistry of such lipids can be found in Romberg et al., Pharmaceutical Research, Vol. 25, No. 1, 2008, p.55-71 and Hoekstra et al., Biochimica et Biophysica Acta 1660 (2004) 41-52.

In one embodiment, the suitable stealth lipid comprises a group selected from PEG (sometimes referred to as poly (ethylene oxide) and polymers based on poly(oxazoline), poly(vinyl alcohol), poly(glycerol), poly(N-vinylpyrrolidone), polyaminoacids and poly[N-(2-hydroxypropyl) methacrylamide]. Additional suitable PEG lipids are disclosed, e.g., in WO 2006/007712.

Specific suitable stealth lipids include polyethyleneglycol-diacylglycerol or polyethyleneglycol-diacylglycamide (PEG-DAG) conjugates including those comprising a dialkylglycerol or dialkylglycamide group having alkyl chain length independently comprising from about $C_4$ to about $C_{40}$ saturated or unsaturated carbon atoms. The dialkylglycerol or dialkylglycamide group can further comprise one or more substituted alkyl groups. In any of the embodiments described herein, the PEG conjugate can be selected from PEG-dilaurylglycerol, PEG-dimyristylglycerol (PEG-DMG) (catalog # GM-020 from NOF, Tokyo, Japan), PEG-dipalmitoylglycerol, PEG-disterylglycerol, PEG-dilaurylglycamide, PEG-dimyristylglycamide, PEG-dipalmitoylglycamide, and PEG-disterylglycamide, PEG-cholesterol (1-[8'-(Cholest-5-en-3[beta]-oxy)carboxamido-3',6'-dioxaoctanyl] carbamoyl-[omega]-methyl-poly (ethylene glycol), PEG-DMB (3,4-Ditetradecoxylbenzyl-[omega]-methyl-poly(ethylene glycol) ether), 1,2-dimyristoyl-sn-glycero-3-phosphoethanolamine-N-[methoxy(polyethylene glycol)-2000] (catalog #880150P from Avanti Polar Lipids, Alabaster, Ala., USA).

In one embodiment the stealth lipid is S010, S024, S027, S031, or S033.

In another embodiment the stealth lipid is S024.

Unless otherwise indicated, the term "PEG" as used herein means any polyethylene glycol or other polyalkylene ether polymer. In one embodiment, PEG is an optionally substituted linear or branched polymer of ethylene glycol or ethylene oxide. In one embodiment PEG is unsubstituted. In one embodiment the PEG is substituted, e.g., by one or more alkyl, alkoxy, acyl, hydroxy or aryl groups. In one embodiment, the term includes PEG copolymers such as PEG-polyurethane or PEG-polypropylene (see, e.g., J. Milton Harris, Poly(ethylene glycol) chemistry: biotechnical and biomedical applications (1992)); in another embodiment, the term does not include PEG copolymers. In one embodiment, the PEG has a molecular weight of from about 130 to about 50,000, in a sub-embodiment about 150 to about 30,000, in a sub-embodiment about 150 to about 20,000, in a sub-embodiment about 150 to about 15,000, in a sub-embodiment about 150 to about 10,000, in a sub-embodiment about 150 to about 6000, in a sub-embodiment about 150 to about 5000, in a sub-embodiment about 150 to about 4000, in a sub-embodiment about 150 to about 3000, in a sub-embodiment about 300 to about 3000, in a sub-embodiment about 1000 to about 3000, and in a sub-embodiment about 1500 to about 2500.

In certain embodiments the PEG is a "PEG-2K", also termed "PEG 2000", which has an average molecular weight of about 2000 daltons. PEG-2K is represented herein by the following formula (XIIa), wherein n is 45, meaning that the number-averaged degree of polymerization comprises about 45 subunits. However, other PEG embodiments known in the art may be used, including, e.g., those where the number-averaged degree of polymerization comprises about 23 subunits (n=23) and/or 68 subunits (n=68).

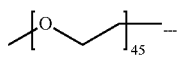
(XIIa)

The lipid compositions of the invention can also include one or more biologically active agents including, but not limited to, antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, enzymatic nucleic acids, antisense nucleic acids, triplex forming oligonucleotides, antisense DNA or RNA compositions, chimeric DNA:RNA compositions, allozymes, aptamers, ribozyme, decoys and analogs thereof, plasmids and other types of expression vectors, and small nucleic acid molecules, RNAi agents, short interfering nucleic acid (siNA), messenger ribonucleic acid" (messenger RNA, mRNA), short interfering RNA (siRNA), double-stranded RNA (dsRNA), micro-RNA (miRNA), and short hairpin RNA (shRNA) molecules, peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), aiRNA (assymetrical interfering RNA), and siRNA with 1, 2 or more mismatches between the sense and anti-sense strand to relevant cells and/or tissues, such as in a cell culture, subject or organism. Such compounds may be purified or partially purified, and may be naturally occuring or synthetic, and may be chemically modified. In one embodiment the biologically active agent is an RNAi agent, short interfering nucleic acid (siNA), short interfering RNA (siRNA), double-stranded RNA (dsRNA), micro-RNA (miRNA), or a short hairpin RNA (shRNA) molecule.

In one embodiment the biologically active agent is a RNAi agent useful for mediating RNA interference (RNAi).

In another embodiment the biologically active agent is a mRNA. The mRNA molecule is generally of a size that it can be encapsulated in a lipid nanoparticle of the invention. While the size of a mRNA molecule varies in nature depending upon the identity of the mRNA species that encodes for a particular protein, an average size for a mRNA molecule is average mRNA size is 500-10,000 bases.

In certain embodiments, the biologically active agent is an RNA encoding an immunogen. The immunogen-coding RNA may be a self-replicating RNA.

In certain embodiments, the biologically active agent is DNA. The DNA molecule should be of a size that it can be encapsulated in a lipid nanoparticle of the invention. Some of these shorter forms of DNA can be of a size to usefully encode for proteins. Examples of these second, shorter, useful forms of DNA include plasmids and other vectors. For a fuller description, see, Alberts B et al. (2007) *Molecular Biology of the Cell, Fifth Edition*, Garland Science.

Various methods for loading biologically active agents into lipid compositions, such as liposomes and lipid nanoparticles are available in the art, including both passive and active loading methods. The exact method used may be chosen based on multiple factors that include, but are not limited to, e.g., the biologically active agent to be loaded, the storage method to be used once loaded, the size of the resulting particle, and the dosage regimen contemplated. Methods include, e.g., mechanical mixing of the drug and lipids at the time the liposomes are formed or reconstituted, dissolving all components in an organic solvent and concentrating them into a dry film, forming a pH or ion gradient to draw the active agent into the interior of the liposome, creating a transmembrane potential, and ionophore mediated loading. See, e.g., PCT Publication No. WO 95/08986, U.S. Pat. Nos. 5,837,282, 5,837,282, and 7,811,602.

By "lipid nanoparticle" is meant a particle that comprises a plurality of (i.e. more than one) lipid molecules physically associated with each other by intermolecular forces. The lipid nanoparticles may be, e.g., microspheres (including unilamellar and multilamellar vesicles, e.g. liposomes), a dispersed phase in an emulsion, micelles or an internal phase in a suspension.

The lipid nanoparticles have a size of about 1 to about 2,500 nm, about 1 to about 1,500 nm, about 1 to about 1,000 nm, in a sub-embodiment about 50 to about 600 nm, in a sub-embodiment about 50 to about 400 nm, in a sub-embodiment about 50 to about 250 nm, and in a sub-embodiment about 50 to about 150 nm. Unless indicated otherwise, all sizes referred to herein are the average sizes (diameters) of the fully formed nanoparticle, as measured by dynamic light scattering on a Malvern Zetasizer. The nanoparticle sample is diluted in phosphate buffered saline (PBS) so that the count rate is approximately 200-400 kcts. The data is presented as a weighted average of the intensity measure.

One embodiment of the present invention provides for a lipid composition comprising a compound of formula (I) and another lipid component. Another embodiment provides for a lipid composition comprising a compound of formula (I) and a helper lipid, for example cholesterol. Another embodiment provides for a lipid composition comprising a compound of formula (I), a helper lipid, for example cholesterol, and a neutral lipid, for example DSPC. Another embodiment of the present invention provides for a lipid composition comprising a compound of formula (I), a helper lipid, for example cholesterol, a neutral lipid, for example DSPC, and a stealth lipid, for example S010, S024, S027, S031, or S033. Another embodiment of the present invention provides for a lipid composition comprising a compound of formula (I), a helper lipid, for example cholesterol, a neutral lipid, for example DSPC, a stealth lipid, for example S010, S024, S027, S031, or S033, and a biologically active agent, for example a RNA or DNA. Another embodiment of the present invention provides for a lipid nanoparticle comprising a compound of formula (I) a helper lipid, for example cholesterol, a neutral lipid, for example DSPC, and a stealth lipid, for example S010, S024, S027, S031, or S033, and a biologically active agent, for example a mRNA, siRNA or DNA.

Embodiments of the present invention also provide lipid compositions described according to the respective molar ratios of the component lipids in the formulation, wherein a slash ("/") indicates the respective components, as provided herein.

Another embodiment of the present invention is a lipid composition comprising a compound of formula (I) and a helper lipid, for example cholesterol, in a lipid molar ratio of 55-40 compound of formula (I)/55-40 helper lipid. Another embodiment provides for a lipid composition comprising a compound of formula (I), a helper lipid, for example cholesterol, and a neutral lipid, for example DPSC in a lipid molar ratio of 55-40 compound of formula (I)/55-40 helper lipid/15-5 neutral lipid. Another embodiment provides for a lipid composition comprising a compound of formula (I), a helper lipid, for example cholesterol, a neutral lipid, for example DSPC, and a stealth lipid, for example S010, S024, S027, S031, or S033 in a lipid molar ratio of 55-40 compound of formula (I)/55-40 helper lipid/15-5 neutral lipid/10-1 stealth lipid.

Another embodiment of the present invention is a lipid composition comprising a compound of formula (I) and a helper lipid, for example cholesterol, in a lipid molar ratio of 50-40 compound of formula (I)/50-40 helper lipid. Another embodiment provides for a lipid composition comprising a compound of formula (I), a helper lipid, for example cholesterol, and a neutral lipid, for example DPSC in a lipid molar ratio of 50-40 compound of formula (I)/50-40 helper lipid/15-5 neutral lipid. Another embodiment provides for a lipid composition comprising a compound of formula (I), a helper lipid, for example cholesterol, a neutral lipid, for example DSPC, a stealth lipid, for example S010, S024, S027, S031, or S033 in a lipid molar ratio of 50-40 compound of formula (I)/50-40 helper lipid/15-5 neutral lipid/5-1 stealth lipid.

Another embodiment of the present invention is a lipid composition comprising a compound of formula (I) and a helper lipid, for example cholesterol, in a lipid molar ratio of 47-43 compound of formula (I)/47-43 helper lipid. Another embodiment provides for a lipid composition comprising a compound of formula (I), a helper lipid, for example cholesterol, and a neutral lipid, for example DPSC in a lipid molar ratio of 47-43 compound of formula (I)/47-43 helper lipid/12-7 neutral lipid. Another embodiment provides for a lipid composition comprising a compound of formula (I), a helper lipid, for example cholesterol, a neutral lipid, for example DSPC, a stealth lipid, for example S010, S024, S027, S031, or S033 in a lipid molar ratio of 47-43 compound of formula (I)/47-43 helper lipid/12-7 neutral lipid/4-1 stealth lipid.

Another embodiment of the present invention is a lipid composition comprising a compound of formula (I) and a helper lipid, for example cholesterol, in a lipid molar ratio of about 45 compound of formula (I)/about 44 helper lipid. Another embodiment provides for a lipid composition comprising a compound of formula (I), a helper lipid, for example cholesterol, and a neutral lipid, for example DPSC in a lipid molar ratio of about 45 compound of formula (I)/about 44 helper lipid/about 9 neutral lipid. Another embodiment provides for a lipid composition comprising a compound of formula (I), a helper lipid, for example cholesterol, a neutral lipid, for example DSPC, a stealth lipid, for example S010, S024, S027, S031, or S033 in a lipid molar ratio of about 45 compound of formula (I)/about 44 helper lipid/about 9 neutral lipid/about 2 stealth lipid, for example S010, S024, S027, S031, or S033.

Preferred compounds of formula (I) for use in the above lipid compositions are given in Examples 1-36. Particularly preferred compounds are given in Examples 1 and 80. Preferred biologically active agents are RNA's and DNA's.

Lipid compositions of the present invention can be further optimized by one skilled in the art by combining cationic lipids with the desired pKa range, stealth lipids, helper lipids, and neutral lipids into formulations, including, e.g., liposome formulations, lipid nanoparticles (LNP) formulations, and the like for delivery to specific cells and tissues in vivo. In one embodiment, further optimization is obtained by adjusting the lipid molar ratio between these various types of lipids. In one embodiment, further optimization is obtained by adjusting one or more of: the desired particle size, N/P ratio, formulation methods and/or dosing regimen (e.g., number of doses administered over time, actual dose in mg/kg, timing of the doses, combinations with other therapeutics, etc.). The various optimization techniques known to those of skill in the art pertaining to the above listed embodiments are considered as part of this invention.

General Methods for Making Lipid Nanoparticles

The following methods can be used to make lipid nanoparticles of the invention. To achieve size reduction and/or to increase the homogeneity of size in the particles, the skilled person may use the method steps set out below, experimenting with different combinations. Additionally, the skilled person could employ sonication, filtration or other sizing techniques which are used in liposomal formulations.

The process for making a composition of the invention typically comprises providing an aqueous solution, such as citrate buffer, comprising a biologically active agent in a first reservoir, providing a second reservoir comprising an organic solution, such as an organic alcohol, for example ethanol, of the lipid(s) and then mixing the aqueous solution with the organic lipid solution. The first reservoir is optionally in fluid communication with the second reservoir. The mixing step is optionally followed by an incubation step, a filtration or dialysis step, and a dilution and/or concentration step. The incubation step comprises allowing the solution from the mixing step to stand in a vessel for about 0 to about 100 hours (preferably about 0 to about 24 hours) at about room temperature and optionally protected from light. In one embodiment, a dilution step follows the incubation step. The dilution step may involve dilution with aqueous buffer (e.g. citrate buffer or pure water) e.g., using a pumping apparatus (e.g. a peristaltic pump). The filtration step is ultrafiltration or dialysis. Ultrafiltration comprises concentration of the diluted solution followed by diafiltration, e.g., using a suitable pumping system (e.g. pumping apparatus such as a peristaltic pump or equivalent thereof) in conjunction with a suitable ultrafiltration membrane (e.g. GE Hollow fiber cartridges or equivalent). Dialysis comprises solvent (buffer) exchange through a suitable membrane (e.g. 10,000 mwc snakeskin membrane).

In one embodiment, the mixing step provides a clear single phase.

In one embodiment, after the mixing step, the organic solvent is removed to provide a suspension of particles, wherein the biologically active agent is encapsulated by the lipid(s).

The selection of an organic solvent will typically involve consideration of solvent polarity and the ease with which the solvent can be removed at the later stages of particle formation. The organic solvent, which is also used as a solubilizing agent, is preferably in an amount sufficient to provide a clear single phase mixture of biologically active agents and lipids. The organic solvent may be selected from one or more (e.g. two) of chloroform, dichloromethane, diethylether, cyclohexane, cyclopentane, benzene, toluene, methanol, and other aliphatic alcohols (e.g. $C_1$ to $C_8$) such as ethanol, propanol, isopropanol, butanol, tert-butanol, isobutanol, pentanol and hexanol.

The mixing step can take place by any number of methods, e.g., by mechanical means such as a vortex mixer.

The methods used to remove the organic solvent will typically involve diafiltration or dialysis or evaporation at reduced pressures or blowing a stream of inert gas (e.g. nitrogen or argon) across the mixture.

In other embodiments, the method further comprises adding nonlipid polycations which are useful to effect the transformation of cells using the present compositions. Examples of suitable nonlipid polycations include, but are limited to, hexadimethrine bromide (sold under the brand-name POLYBRENE®, from Aldrich Chemical Co., Milwaukee, Wis., USA) or other salts of hexadimethrine. Other suitable polycations include, e.g., salts of poly-L-ornithine, poly-L-arginine, poly-L-lysine, poly-D-lysine, polyallylamine and polyethyleneimine. In certain embodiments, the formation of the lipid nanoparticles can be carried out either in a mono-phase system (e.g. a Bligh and Dyer monophase or similar mixture of aqueous and organic solvents) or in a two-phase system with suitable mixing.

The lipid nanoparticle may be formed in a mono- or a bi-phase system. In a mono-phase system, the cationic lipid(s) and biologically active agent are each dissolved in a volume of the mono-phase mixture. Combining the two solutions provides a single mixture in which the complexes form. In a bi-phase system, the cationic lipids bind to the biologically active agent (which is present in the aqueous phase), and "pull" it into the organic phase. In one embodiment, the lipid nanoparticles are prepared by a method which comprises: (a) contacting the biologically active agent with a solution comprising noncationic lipids and a detergent to form a compound-lipid mixture; (b) contacting cationic lipids with the compound-lipid mixture to neutralize a portion of the negative charge of the biologically active agent and form a charge-neutralized mixture of biologically active agent and lipids; and (c) removing the detergent from the charge-neutralized mixture.

In one group of embodiments, the solution of neutral lipids and detergent is an aqueous solution. Contacting the biologically active agent with the solution of neutral lipids and detergent is typically accomplished by mixing together a first solution of the biologically active agent and a second solution of the lipids and detergent. Preferably, the biologically active agent solution is also a detergent solution. The amount of neutral lipid which is used in the present method is typically determined based on the amount of cationic lipid used, and is typically of from about 0.2 to 5 times the amount of cationic lipid, preferably from about 0.5 to about 2 times the amount of cationic lipid used.

The biologically active agent-lipid mixture thus formed is contacted with cationic lipids to neutralize a portion of the negative charge which is associated with the molecule of interest (or other polyanionic materials) present. The amount of cationic lipids used is typically 3-8 fold more than the calculated molar ratio of negative charge (phosphates).

The methods used to remove the detergent typically involve dialysis. When organic solvents are present, removal is typically accomplished by diafilitration or evaporation at reduced pressures or by blowing a stream of inert gas (e.g. nitrogen or argon) across the mixture.

There is herein disclosed an apparatus for making a composition of the present invention. The apparatus typically includes a first reservoir for holding an aqueous solution comprising a biologically active agent and a second reservoir for holding an organic lipid solution. The apparatus also typically includes a pump mechanism configured to pump the aqueous and the organic lipid solutions into a mixing region or mixing chamber at substantially equal flow rates. In one embodiment, the mixing region or mixing chamber comprises a T coupling or equivalent thereof, which allows the aqueous and organic fluid streams to combine as input into the T connector and the resulting combined aqueous and organic solutions to exit out of the T connector into a collection reservoir or equivalent thereof. Methods for Delivering Biologically Active Agents and the Treatment of Disease The cationic lipids of formula (I) and lipid compostions thereof are useful in pharmaceutical compositions or formulations used for delivery of biologically active agents. Formulations containing cationic lipds of formula (I) or lipid compositions thereof may be in various forms, including, but not limited to, particle forming delivery agents including microparticles, nanoparticles and transfection agents that are useful for delivering various molecules to cells. Specific formulations are effective at transfecting or delivering biologically active agents, such as antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, polynucleotides (e.g., RNA or DNA), enzymatic nucleic acids, antisense nucleic acids, triplex forming oligonucleotides, antisense DNA or RNA compositions, chimeric DNA:RNA compositions, allozymes, aptamers, ribozyme, decoys and analogs thereof, plasmids and other types of expression vectors, and small nucleic acid molecules, mRNA, RNAi agents, short interfering nucleic acid (siNA), short interfering RNA (siRNA), double-stranded RNA (dsRNA), micro-RNA (miRNA), and short hairpin RNA (shRNA), molecules peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), aiRNA (assymetrical interfering RNA), and siRNA with 1, 2 or more mismatches between the sense and anti-sense strand to relevant cells and/or tissues, such as in a cell culture, subject or organism. The above list of biologically active agents is exemplary only, and is not intended to be limiting. Such compounds may be purified or partially purified, and may be naturally occuring or synthetic, and may be chemically modified.

Such formulations containing biologically active agents are useful, e.g., in providing compositions to prevent, inhibit, or treat diseases, conditions, or traits in a cell, subject or organism. Diseases, conditions or traits include, but are not limited to, proliferative diseases, including cancer, inflammatory disease, transplant and/or tissue rejection, autoimmune diseases or conditions, age-related disease, neurological or neurodegenerative disease, respiratory disease, cardiovacular disease, ocular disease, metabolic disease, dermatological disease, auditory disease, a liver disease, a kidney or renal disease, etc.

The amount of active agent administered per dose is an amount above the minimal therapeutic dose but below a toxic dose. The actual amount per dose may be determined by a physician depending on a number of factors, such as the medical history of the patient, the use of other therapies, the biologically active agent to be provided, and the nature of the disease. The amount of biologically active agent administered may be adjusted throughout treatment, depending on the patient's response to treatment and the presence or severity of any treatment-associated side effects. Exemplary dosages and treatment for compounds that have been approved by an appropriate regulatory agency are known and available to those skilled in the art. See, e.g., Physician's Desk Reference, 64th ed., Physician's Desk Reference Inc. (2010), Remington's Pharmaceutical Sciences, Mack Publishing Company, Philadelphia, Pa. (1985), and Remington The Science and Practice of Pharmacy, 21st ed., Lippincott Williams & Williams Publishers (2005).

In one embodiment, a single dose is administered of a biologically active agent to a patient in need thereof. In one embodiment, multiple doses are administered, wherein the multiple doses may be administered concurrently, sequentially or alternating. In one embodiment, the same formulation is administered over multiple doses. In one embodiment, the formulations differ over multiple doses. In various embodiments, the doses may be administered once a day, or for one, two, three, four or more consecutive days. In one embodiment, the doses are administered once a week. In one embodiment, the doses are administered once every other week. In one embodiment, patients receive at least two courses of a treatment regimen, and potentially more, depending on the response of the patient to the treatment. In single agent regimens, total courses of treatment are determined by the patient and physician based on observed responses and toxicity. The above dosage regimens are to be considered as non-limiting examples. Other dosage regimens are contemplated as being within the scope of the invention, and depend on the therapeutic effect desired.

The invention also provides a method for the treatment of a disease or condition comprising the step of administering a therapeutically effective amount of a lipid composition of the invention to a patient in need of treatment thereof. In one embodiment, the disease or condition is treatable by administering an RNA agent, such as an siRNA or mRNA agent.

The invention also provides for use of a lipid composition of the invention in treating a disease or condition in a patient. In one embodiment, the disease or condition is treatable by administering a siRNA or mRNA agent.

The total amount of lipid in the composition being administered is, in one embodiment, from about 5 to about 30 mg lipid per mg biologically active agent (e.g. mRNA, siRNA, RNA replicon, etc.), in another embodiment from about 5 to about 25 mg lipid per mg biologically active agent (e.g. mRNA, siRNA, RNA replicon,etc.), in another embodiment from about 7 to about 25 mg lipid per mg biologically active agent (e.g. mRNA, siRNA, or RNA replicon, etc.) and in one embodiment from about 7 to about 15 mg lipid per mg biologically active agent (e.g. mRNA, siRNA, or RNA replicon etc.).

As used herein, "treatment" includes ameliorative, curative and prophylactic treatment. As used herein, a "patient" means an animal, preferably a mammal, preferably a human, in need of treatment.

The term "therapeutically effective amount" refers to the amount of the compound of the invention and the biologically active agent (e.g. the therapeutic compound) needed to treat or ameliorate a targeted disease or condition.

The term "immunologically effective amount" refers to the amount of the compound of the invention and of RNA which encodes an immunogen needed to elicit an immune response which recognizes the immunogen (e.g. in the context of a pathogen). The term "immunogen" refers to any substance or organism that provokes an immune response when introduced into the body.

By "proliferative disease" as used herein is meant any disease, condition, trait, genotype or phenotype characterized by unregulated cell growth or replication as is known in the art. In one embodiment, the proliferative disease is cancer. In one embodiment, the proliferative disease is a tumor. In one embodiment, the proliferative disease includes, but are not limited to, e.g., liquid tumors such as, e.g., leukemias, e.g., acute myelogenous leukemia (AML), chronic myelogenous leukemia (CML), acute lymphocytic leukemia (ALL), multiple myeloma, and chronic lymphocytic leukemia; and solid tumors, e.g., AIDS related cancers such as Kaposi's sarcoma; breast cancers; bone cancers; brain cancers; cancers of the head and neck, non-Hodgkins lymphoma, adenoma, squamous cell carcinoma, laryngeal carcinoma, gallbladder and bile duct cancers, cancers of the retina, cancers of the esophagus, gastrointestinal cancers, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, endometrial sarcoma, multidrug resistant cancers. In one embodiment, the proliferative disease includes neovascularization associated with tumor angiogenesis, macular degeneration (e.g. wet/dry age related macular degeneration), corneal neovascularization, diabetic retinopathy, neovascular glaucoma, myopic degeneration. In one embodiment, the proliferative disease includes restenosis and polycystic kidney disease.

By "autoimmune disease" as used herein is meant any disease, condition, trait, genotype or phenotype characterized by autoimmunity as is known in the art. Autoimmune diseases include, but are not limited to, e.g., multiple sclerosis, diabetes mellitus, lupus, scleroderms, fibromyalgia, transplantation rejection (e.g. prevention of allograft rejection), pernicious anemia, rheumatoid arthritis, systemic lupus erythematosus, dermatomyositis, myasthenia gravis, lupus erythematosus, multiple sclerosis, and Grave's disease.

By "infectious disease" is meant any disease, disorder or condition associated with an infectious agent, such as a virus, bacteria, fungus, prion or parasite. The invention can be used to immunize against pathogens which cause infectious disease. Examples of such pathogens are given below.

By "neurologic disease" is meant any disease, disorder, or condition affecting the central or peripheral nervous system. Neurologic diseases include, but are not limited to, diseases or disorders of either the peripheral or the central nervous system including, e.g., Alzheimer's Disease, Aneurysm, Brain Injury, Carpal Tunnel Syndrome, Cerebral Aneurysm, Chronic Pain, Creutzfeldt-Jakob Disease, Epilepsy, Huntington's Disease, Meningitis, Seizure Disorders, and other neurologic diseases, disorders and syndromes.

By "respiratory disease" is meant any disease or condition affecting the respiratory tract. Respiratory diseases include, but are not limited to, e.g., asthma, chronic obstructive pulmonary disease (COPD), allergic rhinitis, sinusitis, allergies, impeded respiration, respiratory distress syndrome, cystic fibrosis, pulmonary hypertension or vasoconstriction and emphysema.

By "cardiovascular disease" is meant and disease or condition affecting the heart and vasculature. Cardiovascular diseases include, but are not limited to, e.g., coronary heart disease (CHD), cerebrovascular disease (CVD), aortic stenosis, peripheral vascular disease, myocardial infarction (heart attack), arrhythmia, ischemia, and congestive heart failure.

By "ocular disease" as used herein is meant any disease, condition, trait, genotype or phenotype of the eye and related structures. Ocular diseases include, but are not limited to, e.g., cystoid macular edema, diabetic retinopathy, lattice degeneration, retinal vein occlusion, retinal artery occlusion, macular degeneration (e.g. age related macular degeneration such as wet AMD or dry AMD), toxoplasmosis, retinitis pigmentosa, conjunctival laceration, corneal laceration, glaucoma, and the like.

By "metabolic disease" is meant any disease or condition affecting metabolic pathways. Metabolic disease can result in an abnormal metabolic process, either congenital due to inherited enzyme abnormality (inborn errors of metabolism) or acquired due to disease of an endocrine organ or failure of a metabolically important organ such as the liver. In one embodiment, metabolic disease includes obesity, insulin resistance, and diabetes (e.g. type I and/or type II diabetes).

By "dermatological disease" is meant any disease or condition of the skin, dermis, or any substructure therein such as a hair, a follicle, etc. Dermatological diseases, disorders, conditions, and traits can include psoriasis, ectopic dermatitis, skin cancers such as melanoma and basal cell carcinoma, hair loss, hair removal and alterations in pigmentation.

By "auditory disease" is meant any disease or condition of the auditory system, including the ear, such as the inner ear, middle ear, outer ear, auditory nerve, and any substructures therein. Auditory diseases, disorders, conditions, and traits can include hearing loss, deafness, tinnitus, vertigo, balance and motion disorders.

By "regenerative disease" is meant any disease or condition where insufficient cell or tissue generation or regeneration in vivo or in vitro prevents the establishment or restoration of proper organ function before or after injury, prevents or slows wound healing or resolution of ulcerative lesions, accelerates ageing, or prevents effective cell-based therapy. The term "messenger ribonucleic acid" (messenger RNA, mRNA) refers to a ribonucleic acid (RNA) molecule that mediates the transfer of genetic information to ribosomes in the cytoplasm, where it serves as a template for protein synthesis. It is synthesized from a DNA template during the process of transcription. See, *The American Heritage® Dictionary of the English Language, Fourth Edition* (Updated in 2009). Houghton Mifflin Company.

A plasmid is a small DNA molecule that is physically separate from, and can replicate independently of, chromosomal DNA within a cell. Plasmid sizes can vary from 1 to over 25 kilobase pairs. A recombinant plasmid can be recombinantly made to be of a size that it can be encapsulated in a lipid nanoparticle of the invention.

A vector is a DNA molecule used as a vehicle to artificially carry genetic material from one cell or from a biochemical reaction in vitro into another cell, where the DNA can be replicated and/or expressed. A vector containing foreign DNA is termed recombinant. Among the types of useful vectors are plasmids and viral vectors.

Viral vectors are generally recombinant viruses carrying modified viral DNA or RNA that has been rendered noninfectious, but that still contain viral promoters and also the transgene, thus allowing for translation of the transgene through a viral promoter. A viral vector can be recombinantly made to be of a size that it can be encapsulated in a lipid nanoparticle of the invention.

The term "short interfering nucleic acid" (siNA) as used herein refers to any nucleic acid molecule capable of inhibiting or down regulating gene expression or viral replication by mediating RNA interference (RNAi) or gene silencing in a sequence-specific manner. It includes short interfering RNA (siRNA), microRNA (miRNA), short interfering oligonucleotides and chemically-modified short interfering nucleic acid molecules. siRNAs are responsible for RNA interference, the process of sequence-specific post-transcriptional gene silencing in animals and plants. siRNAs are generated by ribonuclease III cleavage from longer double-stranded RNA (dsRNA) which are homologous to, or specific to, the silenced gene target.

The term "RNA interference" (RNAi) is a post-transcriptional, targeted gene-silencing technique that uses a RNAi agent to degrade messenger RNA (mRNA) containing a sequence which is the same as or very similar to the RNAi agent. See: Zamore and Haley, 2005, Science, 309, 1519-1524; Zamore et al., 2000, Cell, 101, 25-33; Elbashir et al., 2001, Nature, 411, 494-498; and Kreutzer et al., PCT Publication WO 00/44895; Fire, PCT Publication WO 99/32619; Mello and Fire, PCT Publication WO 01/29058; and the like.

As used herein, RNAi is equivalent to other terms used to describe sequence specific RNA interference, such as post transcriptional gene silencing, translational inhibition, transcriptional inhibition, or epigenetics. For example, the formulations containing lipids of the invention can be used in conjunction with siNA molecules to epigenetically silence genes at both the post-transcriptional level and/or the pre-transcriptional level. In a non-limiting example, modulation of gene expression by siNA molecules can result from siNA mediated cleavage of RNA (either coding or non-coding RNA) via RISC, or alternately, translational inhibition as is known in the art. In another embodiment, modulation of gene expression by siNA can result from transcriptional inhibition such as is reported e.g., in Janowski et al., 2005, Nature Chemical Biology, 1, 216-222.

The term "RNAi inhibitor" is any molecule that can down modulate (e.g. reduce or inhibit) RNA interference function or activity in a cell or patient. An RNAi inhibitor can down regulate, reduce or inhibit RNAi (e.g. RNAi mediated cleavage of a target polynucleotide, translational inhibition, or transcriptional silencing) by interaction with or interfering with the function of any component of the RNAi pathway, including protein components such as RISC, or nucleic acid components such as miRNAs or siRNAs. An RNAi inhibitor can be a siNA molecule, an antisense molecule, an aptamer, or a small molecule that interacts with or interferes with the function of RISC, a miRNA, or a siRNA or any other component of the RNAi pathway in a cell or patient. By inhibiting RNAi (e.g. RNAi mediated cleavage of a target polynucleotide, translational inhibition, or transcriptional silencing), an RNAi inhibitor can be used to modulate (e.g, up-regulate or down-regulate) the expression of a target gene. In one embodiment, an RNA inhibitor is used to up-regulate gene expression by interfering with (e.g. reducing or preventing) endogenous down-regulation or inhibition of gene expression through translational inhibition, transcriptional silencing, or RISC mediated cleavage of a polynucleotide (e.g. mRNA). By interfering with mechanisms of endogenous repression, silencing, or inhibition of gene expression, RNAi inhibitors of the invention can therefore be used to up-regulate gene expression for the treatment of diseases or conditions resulting from a loss of function. The term "RNAi inhibitor" is used interchangeably with the term "siNA" in various embodiments herein.

The term "enzymatic nucleic acid" as used herein refers to a nucleic acid molecule that has complementarity in a substrate binding region to a specified gene target, and also has an enzymatic activity that acts to specifically cleave a target RNA, thereby inactivating the target RNA molecule. The complementary regions allow sufficient hybridization of the enzymatic nucleic acid molecule to the target RNA and thus permit cleavage. Complementarity of 100% is preferred, but complementarity as low as 50-75% can also be useful in this invention (see e.g., Werner and Uhlenbeck, 1995, Nucleic Acids Research, 23, 2092-2096; Hammann et al., 1999, Antisense and Nucleic Acid Drug Dev., 9, 25-31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The key features of an enzymatic nucleic acid molecule are that it has a specific substrate binding site that is complementary to one or more of the target nucleic acid regions, and that it has nucleotide sequences within or surrounding that substrate binding site that impart a nucleic acid cleaving and/or ligation activity to the molecule (see, e.g., Cech et al., U.S. Pat. No. 4,987,071; Cech et al., 1988, 260 JAMA 3030). Ribozymes and enzymatic nucleic acid molecules of the invention can be chemically modified, e.g., as described in the art and elsewhere herein.

The term "antisense nucleic acid", as used herein, refers to a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Antisense DNA can be synthesized chemically or expressed via the use of a single stranded DNA expression vector or equivalent thereof. Antisense molecules of the invention can be chemically modified, e.g. as described in the art.

The term "RNase H activating region" as used herein, refers to a region (generally greater than or equal to 4-25 nucleotides in length, preferably from 5-11 nucleotides in length) of a nucleic acid molecule capable of binding to a target RNA to form a non-covalent complex that is recognized by cellular RNase H enzyme (see e.g., Arrow et al., U.S. Pat. No. 5,849,902; Arrow et al., U.S. Pat. No. 5,989, 912). The RNase H enzyme binds to the nucleic acid molecule-target RNA complex and cleaves the target RNA sequence.

The term "2-5A antisense chimera" as used herein, refers to an antisense oligonucleotide containing a 5'-phosphorylated 2'-5'-linked adenylate residue. These chimeras bind to target RNA in a sequence-specific manner and activate a cellular 2-5A-dependent ribonuclease that, in turn, cleaves the target RNA (Torrence et al., 1993 Proc. Natl. Acad. Sci. USA 90, 1300; Silverman et al., 2000, Methods Enzymol., 313, 522-533; Player and Torrence, 1998, Pharmacol. Ther., 78, 55-113). 2-5A antisense chimera molecules can be chemically modified, e.g. as described in the art.

The term "triplex forming oligonucleotides" as used herein, refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504; Fox, 2000, Curr. Med. Chem., 7, 17-37; Praseuth et. al., 2000, Biochim. Biophys. Acta, 1489, 181-206). Triplex forming oligonucleotide molecules of the invention can be chemically modified, e.g. as described in the art.

The term "decoy RNA" as used herein, refers to an RNA molecule or aptamer that is designed to preferentially bind to a predetermined ligand. Such binding can result in the inhibition or activation of a target molecule. The decoy RNA or aptamer can compete with a naturally occurring binding target for the binding of a specific ligand. Similarly, a decoy RNA can be designed to bind to a receptor and block the binding of an effector molecule, or can be designed to bind to receptor of interest and prevent interaction with the receptor. Decoy molecules of the invention can be chemically modified, e.g. as described in the art.

The term "single stranded DNA" (ssDNA) as used herein refers to a naturally occurring or synthetic deoxyribonucleic acid molecule comprising a linear single strand, e.g., a ssDNA can be a sense or antisense gene sequence or EST (Expressed Sequence Tag).

The term "allozyme" as used herein refers to an allosteric enzymatic nucleic acid molecule, including e.g., U.S. Pat. Nos. 5,834,186, 5,741,679, 5,589,332, 5,871,914, and PCT publication Nos. WO 00/24931, WO 00/26226, WO 98/27104, and WO 99/29842.

The term "aptamer" as used herein is meant a polynucleotide composition that binds specifically to a target molecule, wherein the polynucleotide has a sequence that differs from a sequence normally recognized by the target molecule in a cell. Alternately, an aptamer can be a nucleic acid molecule that binds to a target molecule where the target molecule does not naturally bind to a nucleic acid. The target molecule can be any molecule of interest. Aptamer molecules of the invention can be chemically modified, e.g. as described in the art.

Formulation of Lipid Compositions

For pharmaceutical use, the lipid compositions of the invention may be administered by enteral or parenteral routes, including intravenous, intramuscular, subcutaneous, transdermal, airway (aerosol), oral, intranasal, rectal, vaginal, buccal, nasopharangeal, gastrointestinal or sublingual administration. The administration may be systemic or topical. Topical administration may involve, e.g., catheterization, implantation, osmotic pumping, direct injection, dermal/transdermal application, stenting, ear/eye drops or portal vein administration. The compounds of formula (I) should be assessed for their biopharmaceutical properties, such as solubility and solution stability (across pH), permeability, etc., in order to select the most appropriate dosage form and route of administration for treatment of the proposed indication.

The compositions of the invention will generally, but not necessarily, be administered as a formulation in association with one or more pharmaceutically acceptable excipients. The term "excipient" includes any ingredient other than the compound(s) of the invention, the other lipid component(s) and the biologically active agent. An excipient may impart either a functional (e.g drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

Typical pharmaceutically acceptable excipients include:
diluents, e.g. lactose, dextrose, sucrose, mannitol, sorbitol, cellulose and/or glycine;
lubricants, e.g. silica, talcum, stearic acid, its magnesium or calcium salt and/or polyethyleneglycol;
binders, e.g. magnesium aluminum silicate, starch paste, gelatin, tragacanth, methylcellulose, sodium carboxymethylcellulose and/or polyvinylpyrrolidone;
disintegrants, e.g. starches, agar, alginic acid or its sodium salt, or effervescent mixtures; and/or
absorbants, colorants, flavors and/or sweeteners.

The excipient may be an aqueous solution carrier which may optionally contain a buffer (e.g. a PBS buffer) and/or a sugar.

A thorough discussion of pharmaceutically acceptable excipients is available in Gennaro, *Remington: The Science and Practice of Pharmacy* 2000, 20th edition (ISBN: 0683306472).

The compositions of the invention may be administered orally. Oral administration may involve swallowing, so that the compound enters the gastrointestinal tract, and/or buccal, lingual, or sublingual administration by which the compound enters the blood stream directly from the mouth.

The compositions of the invention can be administered parenterally. The compounds and compositions of the invention may be administered directly into the blood stream, into subcutaneous tissue, into muscle, or into an internal organ. Suitable means for administration include intravenous, intraarterial, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions. Where the solution is aqueous, excipients such as sugars (including but not restricted to glucose, mannitol, sorbitol, etc.) salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water (WFI).

Parenteral formulations may include implants derived from degradable polymers such as polyesters (i.e. polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, e.g., by lyophilisation, may readily be accomplished using standard pharmaceutical techniques well known to the skilled person.

The solubility of the compounds and compositions used in the preparation of parenteral solutions may be increased by the use of appropriate formulation techniques, such as the incorporation of co-solvents and/or solubility-enhancing agents such as surfactants, micelle structures and cyclodextrins.

The compositions of the invention can be administered intranasally or by inhalation, typically in the form of a dry powder (either alone, as a mixture, e.g., in a dry blend with lactose, or as a mixed component particle, e.g., mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, e.g., chitosan or cyclodextrin.

The pressurized container, pump, spray, atomizer, or nebuliser contains a solution or suspension of the compound(s) of the invention comprising, e.g., ethanol, aqueous ethanol, or a suitable alternative agent for dispersing, solubilising, or extending release of the compositions of the invention, a propellant(s) as solvent and an optional surfactant, such as sorbitan trioleate, oleic acid, or an oligolactic acid.

Prior to use in a dry powder or suspension formulation, the composition is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, e.g., from gelatin or hydroxypropylmethylcellulose), blisters and cartridges for use in an inhaler or insufflator may be formulated to contain a powder mix of the compound or composition of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Formulations for inhaled/intranasal administration may be formulated to be immediate and/or modified release using, e.g., PGLA. Modified release formulations include delayed-, sustained-, pulsed-, controlled-, targeted and programmed release.

Suitable formulations for transdermal application include a therapeutically effective amount of a compound or composition of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Lipid compositions of the invention are administered in any of a number of ways, including parenteral, intravenous, systemic, local, oral, intratumoral, intramuscular, subcutaneous, intraperitoneal, inhalation, or any such method of delivery. In one embodiment, the compositions are administered parenterally, i.e., intraarticularly, intravenously, intraperitoneally, subcutaneously, or intramuscularly. In a specific embodiment, the liposomal compositions are administered by intravenous infusion or intraperitoneally by a bolus injection.

Lipid compositions of the invention can be formulated as pharmaceutical compositions suitable for delivery to a subject. The pharmaceutical compositions of the invention will often further comprise one or more buffers (e.g., neutral buffered saline or phosphate buffered saline), carbohydrates (e.g., glucose, mannose, sucrose, dextrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

Suitable formulations for use in the present invention can be found, e.g., in Remington's Pharmaceutical Sciences, Mack Publishing Company, Philadelphia, Pa., 17.sup.th Ed. (1985). Often, compositions will comprise a solution of the lipid nanoparticles suspended in an acceptable carrier, such as an aqueous carrier.

In one embodiment, this invention provides for a pharmaceutical composition (i.e. formulation) comprising a lipid composition of the invention and a pharmaceutically acceptable carrier or excipient. In another embodiment at least one other lipid component is present in the lipid composition. In another embodiment the lipid composition is in the form of a liposome. In another embodiment the lipid composition is in the form of a lipid nanoparticle. In another embodiment the lipid composition is suitable for delivery to the liver. In another embodiment the lipid composition is suitable for delivery to a tumor. In another embodiment the lipid composition is suitable for local delivery applications (eye, ear, skin, lung); delivery to muscle (i.m.), fat, or sub cutaneous cells (s.c. dosing). In another embodiment the biologically active agent is a RNA or DNA.

For immunization purposes a composition will generally be prepared as an injectable, and will be administered by injection (e.g. by intramuscular injection).

The invention also provides a delivery device (e.g. syringe, nebuliser, sprayer, inhaler, dermal patch, etc.) containing a composition of the invention. This device can be used to administer a pharmaceutical composition to a subject e.g. to a vertebrate (e.g., a mammal, such as a human) for immunization.

Cells and Organs Targeted by the Invention

The compounds, compositions, methods and uses of the invention can be used to deliver a biologically active agent to one or more of the following in a patient:

the liver or liver cells (e.g. hepatocytes);
a kidney or kidney cells;
a tumor or tumor cells;
the CNS or CNS cells (Central Nervous System, e.g. brain and/or spinal cord);
the PNS or PNS cells (Peripheral Nervous System);
a lung or lung cells;
the vasculature or vascular cells;
the skin or skin cells (e.g. dermis cells and/or follicular cells);
an eye or ocular cells (e.g. macula, fovea, cornea, retina), and
an ear or cells of the ear (e.g. cells of the inner ear, middle ear and/or outer ear).

The compounds, compositions, methods and uses of the invention can also be used to deliver a biologically active agent (e.g. RNA which encodes an immunogen) to cells of the immune system.

In one embodiment, the compounds, compositions, methods and uses of the invention are for delivering a biologically active agent to liver cells (e.g. hepatocytes). In one embodiment, the compounds, compositions, methods and uses of the invention are for delivering a biologically active agent to a tumor or to tumor cells (e.g. a primary tumor or metastatic cancer cells). In another embodiment, the compounds, compositions, methods and uses are for delivering a biologically active agent to the skin adipose, muscle and lymph nodes (i.e. sc dosing).

For delivery of a biologically active agent to the liver or liver cells, in one embodiment a composition of the invention is contacted with the liver or liver cells of the patient as is generally known in the art, such as via parental administration (e.g. intravenous, intramuscular, subcutaneous administration) or local administration (e.g. direct injection, portal vein injection, catheterization, stenting), to facilitate delivery.

For delivery of a biologically active agent to the kidney or kidney cells, in one embodiment a composition of the invention is contacted with the kidney or kidney cells of the patient as is generally known in the art, such as via parental administration (e.g. intravenous, intramuscular, subcutaneous administration) or local administration (e.g. direct injection, catheterization, stenting), to facilitate delivery.

For delivery of a biologically active agent to a tumor or tumor cells, in one embodiment a composition of the invention is contacted with the tumor or tumor cells of the patient as is generally known in the art, such as via parental administration (e.g. intravenous, intramuscular, subcutaneous administration) or local administration (e.g. direct injection, catheterization, stenting), to facilitate delivery.

For delivery of a biologically active agent to the CNS or CNS cells (e.g. brain cells and/or spinal cord cells), in one embodiment a composition of the invention is contacted with the CNS or CNS cells (e.g. brain cells and/or spinal cord cells) of the patient as is generally known in the art, such as via parental administration (e.g. intravenous, intramuscular, subcutaneous administration) or local administration (e.g. direct injection, catheterization, stenting, osmotic pump administration (e.g. intrathecal or ventricular)), to facilitate delivery.

For delivery of a biologically active agent to the PNS or PNS cells, in one embodiment a composition of the invention is contacted with the PNS or PNS cells of the patient as is generally known in the art, such as via parental administration (e.g. intravenous, intramuscular, subcutaneous administration) or local administration (e.g. direct injection), to facilitate delivery.

For delivery of a biologically active agent to a lung or lung cells, in one embodiment a composition of the invention is contacted with the lung or lung cells of the patient as is generally known in the art, such as via parental administration (e.g. intravenous, intramuscular, subcutaneous administration) or local administration (e.g. pulmonary administration directly to lung tissues and cells), to facilitate delivery.

For delivery of a biologically active agent to the vasculature or vascular cells, in one embodiment a composition of the invention is contacted with the vasculature or vascular cells of the patient as is generally known in the art, such as via parental administration (e.g. intravenous, intramuscular, subcutaneous administration) or local administration (e.g. clamping, catheterization, stenting), to facilitate delivery.

For delivery of a biologically active agent to the skin or skin cells (e.g. dermis cells and/or follicular cells), in one embodiment a composition of the invention is contacted with the skin or skin cells (e.g. dermis cells and/or follicular cells) of the patient as is generally known in the art, such as via parental administration (e.g. intravenous, intramuscular, subcutaneous administration) or local administration (e.g. direct dermal application, iontophoresis), to facilitate delivery.

For delivery of a biologically active agent to an eye or ocular cells (e.g. macula, fovea, cornea, retina), in one embodiment a composition of the invention is contacted with the eye or ocular cells (e.g. macula, fovea, cornea, retina) of the patient as is generally known in the art, such as via parental administration (e.g. intravenous, intramuscular, subcutaneous administration) or local administration (e.g. direct injection, intraocular injection, periocular injection, subretinal, iontophoresis, use of eyedrops, implants), to facilitate delivery.

For delivery of a biologically active agent to an ear or cells of the ear (e.g. cells of the inner ear, middle ear and/or outer ear), in one embodiment composition of the invention is contacted with the ear or cells of the ear (e.g. cells of the inner ear, middle ear and/or outer ear) of the patient as is generally known in the art, such as via parental administration (e.g. intravenous, intramuscular, subcutaneous administration) or local administration (e.g. direct injection), to facilitate delivery.

For delivery of a biologically active agent (e.g. RNA encoding an immunogen) to cells of the immune system (e.g. antigen-presenting cells, including professional antigen presenting cells), in one embodiment composition of the invention is delivered intramuscularly, after which immune cells can infiltrate the delivery site and process delivered RNA. Such immune cells can include macrophages (e.g.

bone marrow derived macrophages), dendritic cells (e.g. bone marrow derived plasmacytoid dendritic cells and/or bone marrow derived myeloid dendritic cells), monocytes (e.g. human peripheral blood monocytes), etc. (e.g. see WO2012/006372).

Immunization According to the Invention

For immunization purposes, the invention involves delivering a RNA which encodes an immunogen. The immunogen elicits an immune response which recognizes the immunogen, and so can be used to provide immunity against a pathogen, or against an allergen, or against a tumor antigen. Immunising against disease and/or infection caused by a pathogen is preferred.

The RNA is delivered with a lipid composition of the invention (e.g. formulated as a liposome or LNP). Typically the invention utilises liposomes within which immunogen-encoding RNA is encapsulated. Encapsulation within liposomes can protect RNA from RNase digestion. The encapsulation efficiency does not have to be 100%. Presence of external RNA molecules (e.g. on the exterior surface of liposome) or "naked" RNA molecules (RNA molecules not associated with a liposome) is acceptable. Preferably, for a composition comprising a population of liposomes and a population of RNA molecules, at least half of the population of RNA molecules (e.g., at least 50%, at least 55%, at least 60%, at least 65%, at least 70%, at least 75%, at least 80%, at least 85%, at least 90%, or at least 95% of the RNA molecules) are encapsulated in liposomes.

RNA molecules may also be complexed with LNPs. For example, it is not necessary that the lipid forms liposomes (with aqueous core) only. Some lipid nanoparticles may comprise a lipid core (e.g., the composition may comprise a mixture of liposomes and nanoparticles with a lipid core). In such cases, the RNA molecules may be encapsulated by LNPs that have an aqueous core, and complexed with the LNPs that have a lipid core by non-covalent interactions (e.g., ionic interactions between negatively charged RNA and cationic lipid). Encapsulation and complexation with LNPs can protect RNA from RNase digestion. The encapsulation/complexation efficiency does not have to be 100%. Presence of "naked" RNA molecules (RNA molecules not associated with a liposome) is acceptable. Preferably, for a composition comprising a population of LNPs and a population of RNA molecules, at least half of the population of RNA molecules (e.g., at least 50%, at least 55%, at least 60%, at least 65%, at least 70%, at least 75%, at least 80%, at least 85%, at least 90%, or at least 95% of the RNA molecules) are either encapsulated in LNPs, or complexed with LNPs.

Liposomes and LNPs

Liposomes are usually divided into three groups: multi-lamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter<50 nm, and LUVs have a diameter >50 nm. For delivery of immunogen-coding RNA, preferred range of diameters is in the range of 60-180 nm, and more preferably in the range of 80-160 nm.

The lipid composition can also be LNPs. The composition can comprise a mixture of nanoparticles having an aqueous core and nanoparticles having a lipid core. For delivery of immunogen-coding RNA, preferred range of diameters is in the range of 60-180 nm, and more preferably in the range of 80-160 nm.

A liposome or LNP can be part of a composition comprising a population of liposomes or LNPs, and the liposomes or LNPs within the population can have a range of diameters. For a composition comprising a population of liposomes or LNPs with different diameters, it is preferred that (i) at least 80% by number of the liposomes or LNPs have diameters in the range of 60-180 nm, and preferably in the range of 80-160 nm, (ii) the average diameter (by intensity e.g. Z-average) of the population is ideally in the range of 60-180 nm, and preferably in the range of 80-160 nm; and/or (iii) the diameters within the plurality have a polydispersity index<0.2.

To obtain liposomes or LNPs with the desired diameter(s), mixing can be performed using a process in which two feed streams of aqueous RNA solution are combined in a single mixing zone with one stream of an ethanolic lipid solution, all at the same flow rate e.g. in a microfluidic channel.

Useful mixtures of lipids, for forming lipid compositions (e.g., liposomes or LNPs) for immunization uses, comprise: a lipid of formula (I); cholesterol; and a PEGylated lipid, such as PEG-DMG i.e. PEG-conjugated 1,2-dimyristoyl-sn-glycero-3-phosphoethanolamine-N-[methoxy(polyethylene glycol). This mixture may also include a neutral zwitterionic lipid, such as DSPC (1,2-Diastearoyl-sn-glycero-3-phosphocholine) or DPyPE. These (and other) mixtures are used in the examples.

RNA Molecules

After in vivo administration of an immunization composition, the delivered RNA is released and is translated inside a cell to provide the immunogen in situ. In certain embodiments, the RNA is plus ("+") stranded, so it can be translated by cells without needing any intervening replication steps such as reverse transcription. It may also bind to TLR7 receptors expressed by immune cells, thereby initiating an adjuvant effect.

In certain embodiments, the RNA is a self-replicating RNA. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus typically a + strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall result of this sequence of transcriptions is the amplification in the number of the introduced replicon RNAs and so the encoded immunogen becomes a major polypeptide product of the host cell.

One suitable system for achieving self-replication is to use an alphavirus-based RNA replicon. These (+) stranded replicons are translated after delivery to a cell to give of a replicase (or replicase-transcriptase). The replicase is translated as a polyprotein which auto cleaves to provide a replication complex which creates genomic (−) strand copies of the (+) strand delivered RNA. These (−) strand transcripts can themselves be transcribed to give further copies of the (+) stranded parent RNA and also to give a subgenomic transcript which encodes the immunogen. Translation of the subgenomic transcript thus leads to in situ expression of the immunogen by the infected cell. Suitable alphavirus replicons can use a replicase from a sindbis virus, a semliki forest virus, an eastern equine encephalitis virus, a Venezuelan equine encephalitis virus, etc. Mutant or wild-type viruses sequences can be used e.g. the attenuated TC83 mutant of VEEV has been used in replicons.

A preferred self-replicating RNA molecule thus encodes (i) a RNA-dependent RNA polymerase which can transcribe RNA from the self-replicating RNA molecule and (ii) an immunogen. The polymerase can be an alphavirus replicase e.g. comprising one or more of alphavirus proteins nsP1, nsP2, nsP3 and nsP4.

Whereas natural alphavirus genomes encode structural virion proteins in addition to the non structural replicase polyprotein, it is preferred that a self-replicating RNA molecule of the invention does not encode alphavirus structural proteins. Thus a preferred self replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self replicating RNAs of the invention and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. The first (5') open reading frame encodes a replicase; the second (3') open reading frame encodes an immunogen. In some embodiments the RNA may have additional (e.g. downstream) open reading frames e.g. to encode further immunogens (see below) or to encode accessory polypeptides.

A self-replicating RNA molecule can have a 5' sequence which is compatible with the encoded replicase.

Self-replicating RNA molecules can have various lengths but they are typically 5000-25000 nucleotides long e.g. 8000-15000 nucleotides, or 9000-12000 nucleotides. Thus the RNA is longer than seen in siRNA delivery.

A RNA molecule may have a 5' cap (e.g. a 7-methylguanosine). This cap can enhance in vivo translation of the RNA.

The 5' nucleotide of a RNA molecule useful with the invention may have a 5' triphosphate group. In a capped RNA this may be linked to a 7-methylguanosine via a 5'-to-5' bridge. A 5' triphosphate can enhance RIG-I binding and thus promote adjuvant effects.

A RNA molecule may have a 3' poly A tail. It may also include a poly A polymerase recognition sequence (e.g. AAUAAA) near its 3' end.

A RNA molecule useful with the invention for immunization purposes will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

RNA molecules for immunization purposes can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the RNA from a DNA template. Appropriate capping and poly A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT transcribed RNA can function efficiently as a substrate for its self-encoded replicase.

As discussed in WO2011/005799, the self-replicating RNA can include (in addition to any 5' cap structure) one or more nucleotides having a modified nucleobase. For instance, a self-replicating RNA can include one or more modified pyrimidine nucleobases, such as pseudouridine and/or 5 methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7' methylguanosine). In other embodiments, the RNA may include a 5' cap comprising a 7' methylguanosine, and the first 1, 2 or 3 5' ribonucleotides may be methylated at the 2' position of the ribose.

A RNA used with the invention for immunization purposes ideally includes only phosphodiester linkages between nucleosides, but in some embodiments it can contain phosphoramidate, phosphorothioate, and/or methylphosphonate linkages.

Immunogens

RNA molecules used with the invention for immunization purposes encode a polypeptide immunogen. After administration the RNA is translated in vivo and the immunogen can elicit an immune response in the recipient. The immunogen may elicit an immune response against a pathogen (e.g. a bacterium, a virus, a fungus or a parasite) but, in some embodiments, it elicits an immune response against an allergen or a tumor antigen. The immune response may comprise an antibody response (usually including IgG) and/or a cell mediated immune response. The polypeptide immunogen will typically elicit an immune response which recognises the corresponding pathogen (or allergen or tumor) polypeptide, but in some embodiments the polypeptide may act as a mimotope to elicit an immune response which recognises a saccharide. The immunogen will typically be a surface polypeptide e.g. an adhesin, a hemagglutinin, an envelope glycoprotein, a spike glycoprotein, etc.

The RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

In some embodiments the immunogen elicits an immune response against one of these bacteria:

*Neisseria meningitidis*: useful immunogens include, but are not limited to, membrane proteins such as adhesins, autotransporters, toxins, iron acquisition proteins, and factor H binding protein. A combination of three useful polypeptides is disclosed in Giuliani et al. (2006) *Proc Natl Acad Sci USA* 103(29):10834-9.

*Streptococcus pneumoniae*: useful polypeptide immunogens are disclosed in WO2009/016515. These include, but are not limited to, the RrgB pilus subunit, the beta-N-acetyl-hexosaminidase precursor (spr0057), spr0096, General stress protein GSP-781 (spr2021, SP2216), serine/threonine kinase StkP (SP1732), and pneumococcal surface adhesin PsaA.

*Streptococcus pyogenes*: useful immunogens include, but are not limited to, the polypeptides disclosed in WO02/34771 and WO2005/032582.

*Moraxella catarrhalis.*

*Bordetella pertussis*: Useful pertussis immunogens include, but are not limited to, pertussis toxin or toxoid (PT), filamentous haemagglutinin (FHA), pertactin, and agglutinogens 2 and 3.

*Staphylococcus aureus*: Useful immunogens include, but are not limited to, the polypeptides disclosed in WO2010/119343, such as a hemolysin, esxA, esxB, ferrichrome-binding protein (sta006) and/or the sta011 lipoprotein.

*Clostridium tetani*: the typical immunogen is tetanus toxoid.

*Cornynebacterium diphtheriae*: the typical immunogen is diphtheria toxoid.

*Haemophilus influenzae*: Useful immunogens include, but are not limited to, the polypeptides disclosed in WO2006/110413 and WO2005/111066.

*Pseudomonas aeruginosa*

*Streptococcus agalactiae*: useful immunogens include, but are not limited to, the polypeptides disclosed in WO02/34771.

*Chlamydia trachomatis*: Useful immunogens include, but are not limited to, PepA, LcrE, ArtJ, DnaK, CT398, OmpH-like, L7/L12, OmcA, AtoS, CT547, Eno, HtrA and MurG (e.g. as disclosed in WO2005/002619). LcrE (WO2006/138004) and HtrA (WO2009/109860) are two preferred immunogens.

*Chlamydia pneumoniae*: Useful immunogens include, but are not limited to, the polypeptides disclosed in WO02/02606.

*Helicobacter pylori*. Useful immunogens include, but are not limited to, CagA, VacA, NAP, and/or urease (WO03/018054).

*Escherichia coli*: Useful immunogens include, but are not limited to, immunogens derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). Useful UPEC immunogens are disclosed in WO2006/091517 and WO2008/020330. Useful MNEC immunogens are disclosed in WO2006/089264. A useful immunogen for several *E. coli* types is AcfD (WO2009/104092).

*Bacillus anthracis*

*Yersinia pestis*: Useful immunogens include, but are not limited to, those disclosed in WO2007/049155 and WO2009/031043.

*Staphylococcus epidermis*
*Clostridium perfringens* or *Clostridium botulinums*
*Legionella pneumophila*
*Coxiella burnetii*
*Brucella*, such as *B. abortus, B. canis, B. melitensis, B. neotomae, B. ovis, B. suis, B. pinnipediae.*
*Francisella*, such as *F. novicida, F. philomiragia, F. tularensis.*
*Neisseria gonorrhoeae*
*Treponema pallidum*
*Haemophilus ducreyi*
*Enterococcus faecalis* or *Enterococcus faecium*
*Staphylococcus saprophyticus*
*Yersinia enterocolitica*
*Mycobacterium tuberculosis*
*Rickettsia*
*Listeria monocytogenes*
*Vibrio cholerae*
*Salmonella typhi*
*Borrelia burgdorferi*
*Porphyromonas gingivalis*
*Klebsiella*

In some embodiments the immunogen elicits an immune response against one of these viruses:

Orthomyxovirus: Useful immunogens can be from an influenza A, B or C virus, such as the hemagglutinin, neuraminidase or matrix M2 proteins. Where the immunogen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: immunogens include, but are not limited to, those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles virus).

Poxviridae: immunogens include, but are not limited to, those derived from Orthopoxvirus such as Variola vera, including but not limited to, Variola major and Variola minor.

Picornavirus: immunogens include, but are not limited to, those derived from Picornaviruses, such as Enteroviruses, Rhinoviruses, Heparnavirus, Cardioviruses and Aphthoviruses. In one embodiment, the enterovirus is a poliovirus e.g. a type 1, type 2 and/or type 3 poliovirus. In another embodiment, the enterovirus is an EV71 enterovirus. In another embodiment, the enterovirus is a coxsackie A or B virus.

Bunyavirus: immunogens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Heparnavirus: immunogens include, but are not limited to, those derived from a Heparnavirus, such as hepatitis A virus (HAV).

Filovirus: immunogens include, but are not limited to, those derived from a filovirus, such as an Ebola virus (including a Zaire, Ivory Coast, Reston or Sudan ebolavirus) or a Marburg virus.

Togavirus: immunogens include, but are not limited to, those derived from a Togavirus, such as a Rubivirus, an Alphavirus, or an Arterivirus. This includes rubella virus.

Flavivirus: immunogens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: immunogens include, but are not limited to, those derived from a Pestivirus, such as Bovine viral diarrhea (BVDV), Classical swine fever (CSFV) or Border disease (BDV).

Hepadnavirus: immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: immunogens include, but are not limited to, those derived from a Rhabdovirus, such as a Lyssavirus (e.g. a Rabies virus) and Vesiculovirus (VSV).

Caliciviridae: immunogens include, but are not limited to, those derived from Calciviridae, such as Norwalk virus (Norovirus), and Norwalk-like Viruses, such as Hawaii Virus and Snow Mountain Virus.

Coronavirus: immunogens include, but are not limited to, those derived from a SARS coronavirus, avian infectious bronchitis (IBV), Mouse hepatitis virus (MHV), and Porcine transmissible gastroenteritis virus (TGEV). The coronavirus immunogen may be a spike polypeptide.

Retrovirus: immunogens include, but are not limited to, those derived from an Oncovirus, a Lentivirus (e.g. HIV-1 or HIV-2) or a Spumavirus.

Reovirus: immunogens include, but are not limited to, those derived from an Orthoreovirus, a Rotavirus, an Orbivirus, or a Coltivirus.

Parvovirus: immunogens include, but are not limited to, those derived from Parvovirus B19.

Herpesvirus: immunogens include, but are not limited to, those derived from a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: immunogens include, but are not limited to, those derived from Papillomaviruses and Polyomaviruses. The (human) papillomavirus may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: immunogens include those derived from serotype 36 (Ad-36).

In some embodiments, the immunogen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

Fungal immunogens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album,* var. *discoides,* var. *ochraceum, Trichophyton violaceum,* and/or *Trichophyton faviforme*; or from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In some embodiments the immunogen elicits an immune response against a parasite from the *Plasmodium* genus, such as *P. falciparum, P. vivax, P. malariae* or *P. ovale*. Thus the invention may be used for immunising against malaria.

In some embodiments the immunogen elicits an immune response against a parasite from the Caligidae family, particularly those from the *Lepeophtheirus* and *Caligus* genera e.g. sea lice such as *Lepeophtheirus salmonis* or *Caligus rogercresseyi*.

In some embodiments the immunogen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and *Sorghum*, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of *Hymenoptera* including bees (*Apidae*), wasps (*Vespidea*), and ants (*Formicoidae*).

In some embodiments the immunogen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

Pharmaceutical Compositions

A pharmaceutical composition of the invention, particularly one useful for immunization, may include one or more small molecule immunopotentiators. For example, the composition may include a TLR2 agonist (e.g. Pam3CSK4), a TLR4 agonist (e.g. an aminoalkyl glucosaminide phosphate, such as E6020), a TLR7 agonist (e.g. imiquimod), a TLR8 agonist (e.g. resiquimod) and/or a TLR9 agonist (e.g. IC31). Any such agonist ideally has a molecular weight of <2000 Da. Such agonist(s) can, in some embodiments, be encapsulated with the RNA inside liposomes, or encapsulated or complexed with LNPs, but in other embodiments they are unencapsulated or uncomplexed.

Pharmaceutical compositions of the invention may have an osmolality of between 200 mOsm/kg and 400 mOsm/kg, e.g. between 240-360 mOsm/kg, or between 290-310 mOsm/kg. Pharmaceutical compositions of the invention may include one or more preservatives, such as thiomersal or 2 phenoxyethanol. Mercury-free compositions are preferred, and preservative-free vaccines can be prepared.

Compositions comprise an immunologically effective amount of lipid compositions described herein (e.g., liposomes and LNPs), as well as any other components, as needed. Immunologically effective amount refers to the amount administered to an individual, either in a single dose or as part of a series, is effective for treatment (e.g., prophylactic immune response against a pathogen). This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctors assessment of the medical situation, and other relevant factors. It is expected that the amount will fall in a relatively broad range that can be determined through routine trials. The compositions of the invention will generally be expressed in terms of the amount of RNA per dose. A preferred dose has ≤100 µg RNA (e.g. from 10-100 µg, such as about 10 µg, 25 µg, 50 µg, 75 µg or 100 µg), but expression can be seen at much lower levels e.g. ≤1 µg/dose, ≤100 ng/dose, ≤10 ng/dose, ≤1 ng/dose, etc.

The invention also provides a delivery device (e.g. syringe, nebuliser, sprayer, inhaler, dermal patch, etc.) containing a pharmaceutical composition of the invention. This device can be used to administer the composition to a vertebrate subject.

Liposomes or LNPs of the invention do not comprise ribosomes.

Methods of Treatment and Medical Uses

The liposome-formulated or LNP-formulated RNA and pharmaceutical compositions described herein are for in vivo use for inducing an immune response against an immunogen of interest.

The invention provides a method for inducing an immune response in a vertebrate comprising administering an effective amount of the liposome-formulated or LNP-formulated RNA, or pharmaceutical composition, as described herein. The immune response is preferably protective and preferably involves antibodies and/or cell-mediated immunity. The compositions may be used for both priming and boosting purposes. Alternatively, a prime-boost immunization schedule can be a mix of RNA and the corresponding polypeptide antigen (e.g., RNA prime, protein boost).

The invention also provides a liposome, LNP, or pharmaceutical composition for use in inducing an immune response in a vertebrate.

The invention also provides the use of a liposome, LNP, or pharmaceutical composition in the manufacture of a medicament for inducing an immune response in a vertebrate.

By inducing an immune response in the vertebrate by these uses and methods, the vertebrate can be protected against various diseases and/or infections e.g. against bacterial and/or viral diseases as discussed above. The liposomes, LNPs, and compositions are immunogenic, and are more preferably vaccine compositions. Vaccines according to the invention may either be prophylactic (i.e. to prevent infection) or therapeutic (i.e. to treat infection), but will typically be prophylactic.

The vertebrate is preferably a mammal, such as a human or a large veterinary mammal (e.g. horses, cattle, deer, goats, pigs). As used herein "large mammal" refers to mammals having a typical or average adult weight of at least 5 kg, preferably at least 7 kg. Such large mammals can include, for example, humans, non-human primates, dogs, pigs, cattle, deerd, goats, and is meant to exclude small mammals, such as mice, rats, guinea pigs, and other rodents.

Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

Vaccines prepared according to the invention may be used to treat both children and adults. Thus a human patient may be less than 1 year old, less than 5 years old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population. Compositions of the invention will generally be administered directly to a patient. Direct delivery may be accomplished by parenteral injection (e.g. subcutaneously, intraperitoneally, intravenously, intramuscularly, intradermally, or to the interstitial space of a tissue; intraglossal injection is not typically used for immunization purposes. Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml.

The invention may be used to induce systemic and/or mucosal immunity, preferably to elicit an enhanced systemic and/or mucosal immunity.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks and 14 weeks after birth, e.g. at an age of 6 weeks, 10 weeks and 14 weeks, as often used in the World Health Organisation's Expanded Program on Immunisation ("EPI"). In an alternative embodiment, two primary doses are administered about two months apart, e.g. about 7, 8 or 9 weeks apart, followed by one or more booster doses about 6 months to 1 year after the second primary dose, e.g. about 6, 8, 10 or 12 months after the second primary dose. In a further embodiment, three primary doses are administered about two months apart, e.g. about 7, 8 or 9 weeks apart, followed by one or more booster doses about 6 months to 1 year after the third primary dose, e.g. about 6, 8, 10, or 12 months after the third primary dose.

EXAMPLES

Cationic Lipids of Formula (I)

The following examples are intended to illustrate the invention and are not to be construed as being limitations thereon. Temperatures are given in degrees centigrade. If not mentioned otherwise, all evaporative concentrations are performed under reduced pressure, preferably between about 15 mm Hg and 100 mm Hg (=20-133 mbar). The structure of final products, intermediates and starting materials is confirmed by standard analytical methods, e.g., microanalysis or spectroscopic characteristics, e.g., MS, IR, or NMR. Abbreviations used are those conventional in the art, some of which are defined below.

Flash column purification is preferably carried out on silica gel using an appropriate eluent of isocratic or gradient composition.

HPLC analysis is performed on a Waters Atlantis dC18 column (4.6×150 mm, 3 mm), with gradient elution (0% to 95% acetonitrile in water modified with 0.1% v/v trifluoroacetic acid over 20 min and a flow rate of 1.4 mL/min), unless otherwise described.

1H NMR spectra were recorded on a Bruker Avance II 400 MHz spectrometer. All chemical shifts are reported in parts per million (δ) relative to tetramethylsilane. The following abbreviations are used to denote signal patterns: s=singlet, d=doublet, t=triplet, q=quartet, m=multiplet, br=broad. ES-MS data were recorded using a Waters LTC Premier mass spectrometer with a dual electrospray ionization source on an Agilent 1100 liquid chromatograph. Sulfadimethoxine [Sigma, m/z=311.0814 (M+1)] was used as a reference acquired through the LockSpray™ channel every third scan. The mass accuracy of the system has been found to be <5 ppm.

ABBREVIATIONS

AcOH acetic acid
Aq aqueous
Ar aryl
Atm atmosphere
BOC tert-Butyl-carbonate
br.s., bs broad singlet
° C. Celsius
$CD_2Cl_2$ deuterated dichloromethane
$CDCl_3$ deuterated chloroform
$CH_2Cl_2$, DCM dichloromethane
$CH_3CN$, MeCN acetonitrile
d doublet
dd doublet of doublets
ddd doublet of doublets of doublets
DIEA, DIPEA N-ethyldiisopropylamine
DME 1,4-dimethoxyethane
DMF N,N-dimethylformamide DMAP dimethyl aminopyridine
DMSO dimethylsulfoxide
dt doublet of triplets
EDC 1-ethyl-3-(3-dimethylaminopropyl)carbodiimide
EtOAc ethyl acetate
EtOH ethanol
FCC flash column chromatography
G gauge
h hour
HBTU (2-(1H-benzotriazole-1-yl)-1,1,3,3-tetramethyluronium hexafluorophosphate
HCl hydrochloric acid
HMPA hexamethylphosphoramide
HPLC high pressure liquid chromatography
HT high throughput
IBX 2-Iodoxybenzoic acid
i-PrOH isopropyl alcohol
$H_2O$ water
K kelvin
KOH potassium hydroxide
LC liquid chromatography
M molar
m multiplet, mass
MeOH methanol
$MgSO_4$ magnesium sulfate
MHz megahertz
ml, mL milliliter
mm millimeter
mmol millimole
min. minute
mRNA messenger ribonucleic acid
MS mass spectroscopy
mw microwave
NaH sodium hydride
NaHMDS sodium hexamethyldisilazane
NaOEt sodium ethoxide
NaOH sodium hydroxide
$Na_2SO_4$ sodium sulfate
$NEt_3$ triethylamine
ng nanogram
$NH_3$ ammonia
NMR nuclear magnetic resonance
quint. quintuplet
Pd/C palladium on carbon
ppt precipitate
rbf round bottom flask
Rf retardation factor
rt room temperature
Rt Retention time
s singlet
sat. saturated
siRNA small interfering ribonucleic acid
SM starting material
t triplet
TFA trifluoroacetic acid
THF tetrahydrofuran
TLC thin layer chromatography
UPLC ultra performance liquid chromatography
wt weight
pg microgram
pL microliter
All compounds are named using AutoNom.
LC Specificity:
 LC Method 1:
 The retention times (Rt) were obtained on a Waters Acquity SDS system with an Inersil C8 3.0 μm, 3.0×53 mm column. A gradient of $H_2O$ (+0.1% formic acid)/$CH_3CN$ (+0.1% formic acid) 40/60 to 5/95 was applied over 1.0 min., then held for 2.1 min. (1.0 mL/min. as solvent flow) at an oven temperature of 50° C.
 LC Method 2:
 The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 45/55 to 1/99 was applied over 1.4 min., then held for 3.6 min. (1.0 mL/min. as solvent flow) at an oven temperature of 50° C.
 LC Method 3:
 The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 45/55 to 1/99 was applied over 0.7 min., then held for 1.3 min. (1.0 mL/min. as solvent flow) at an oven temperature of 50° C.
 LC Method 4:
 The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 45/55 to 0.1/99.9 was applied over 3.6 min., then held for 1.4 min. (1.0 mL/min. as solvent flow) at an oven temperature of 50° C.
 LC Method 5:
 The retention times (Rt) were obtained on a Waters Acquity SDS system with an ACQUITY UPLC BEH C18 130 Å 1.7 μm 2.1 mm×50 mm column. A gradient of $H_2O$ (+0.1% formic acid)/$CH_3CN$ (+0.1% formic acid) 60/40 to 2/98 was applied over 3.40 min., then held for 1.40 min. (1.0 mL/min. as solvent flow) at an oven temperature of 50° C.
 LC Method 6:
 The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 45/55 to 1/99 was applied over 1.4 min, followed by an increase to 0/100 over 3.75 min and a decrease to 45/55 over 0.04 min (1.0 mL/min. as solvent flow) at an oven temperature of 50° C.
Synthetic Strategy Scheme 1

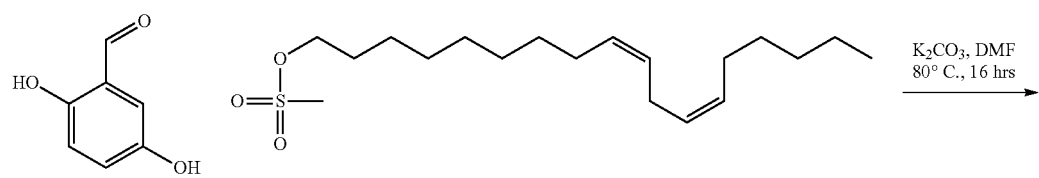

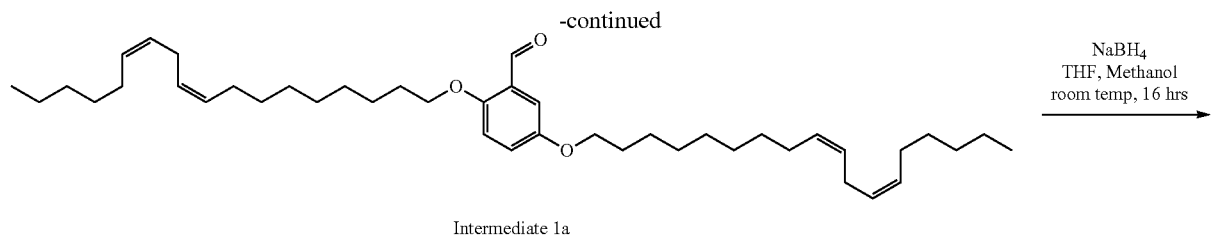

Intermediate 1a

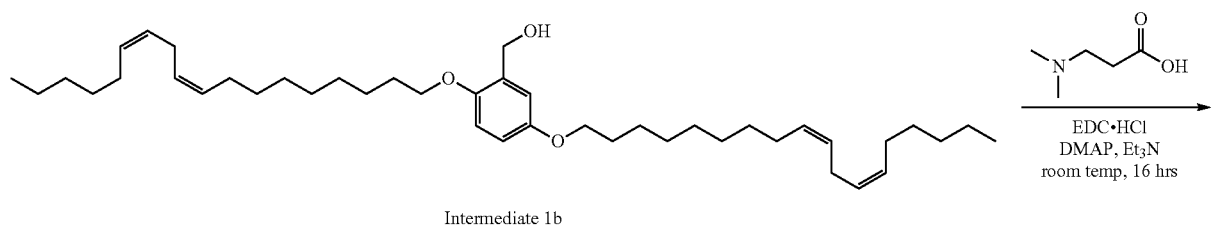

Intermediate 1b

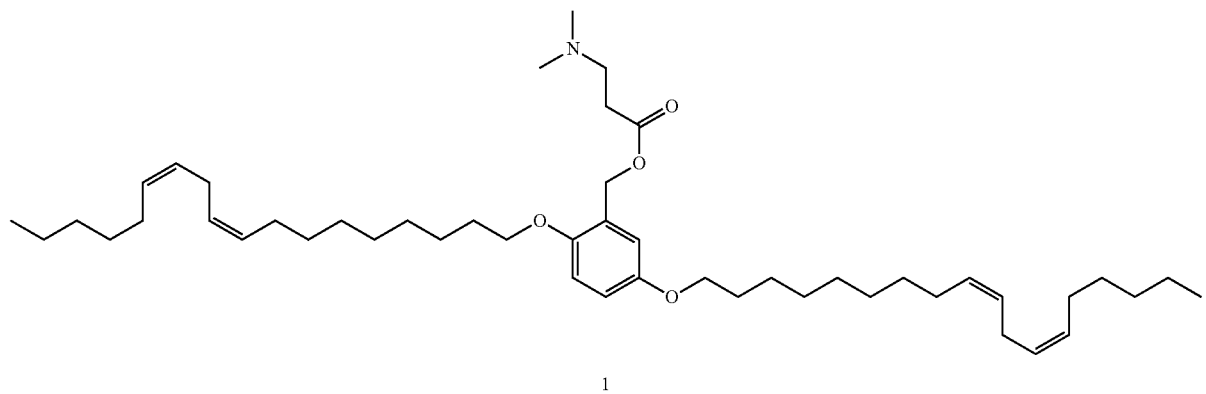

1

Synthesis of Example 1: 2,5-bis((9Z,12Z)-octadeca-9,12-dien-1-yloxy)benzyl 4-(dimethylamino)butanoate Intermediate 1a: 2,5-bis((9Z,12Z)-octadeca-9,12-dien-1-yloxy)benzaldehyde

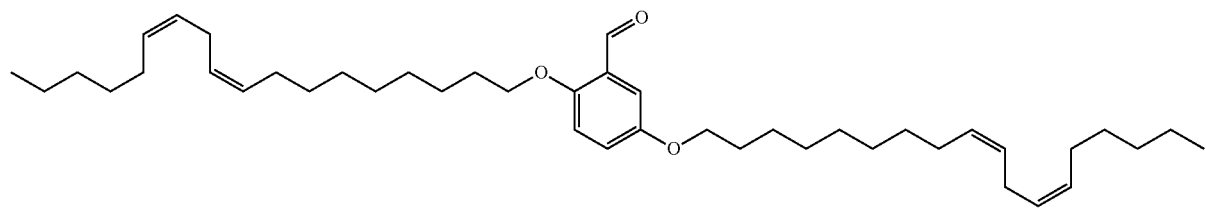 [SMILES: CCCCC/C=C\C/C=C\CCCCCCCCOc1ccc(OCCCCCCCC/C=C\C/C=C\CCCCC)c(C=O)c1]

To a solution of 2,5-dihydroxybenzaldehyde (0.551 g, 3.99 mmol) in DMF (35 mL) was added (9Z,12Z)-octadeca-9,12-dienyl methanesulfonate (2.75 g, 7.98 mmol) followed by K$_2$CO$_3$ (4.41 g, 31.9 mmol) and heated to 80° C. for 16 h. Reaction was diluted with 100 ml ethyl acetate and 100 ml water. Organic layer was separated, washed with 2×50 ml water, dried over Na$_2$SO$_4$ and concentrated under reduced pressure to give crude product. Crude product was purified by silica gel chromatography eluting with 10-90% ethyl acetate: heptane to afford desired product as colorless oil (1.3 g, 26% yield). $^1$H NMR (400 MHz, CDCl$_3$) δ: 10.48 (s, 1H), 7.31 (d, J=3.5 Hz, 1H), 7.12 (dd, J=9.0, 3.5 Hz, 1H), 6.93 (d, J=9.0 Hz, 1H), 5.29-5.46 (m, 8H), 4.03 (t, J=6.5 Hz, 2H), 3.94 (t, J=6.5 Hz, 2H), 2.78 (t, J=6.3 Hz, 4H), 2.01-2.13 (m, 8H), 1.72-1.87 (m, 4H), 1.46 (dt, J=14.1, 7.0 Hz, 4H), 1.24-1.41 (m, 28H), 0.89 (t, J=7.0 Hz, 6H). $^{13}$C NMR (400 MHz, CDCl$_3$) δ: 189.7, 156.3, 153.0, 130.2, 130.1, 130.0, 128.0, 128.0, 127.9, 127.9, 125.0, 124.1, 114.3, 110.7, 69.1, 68.6, 31.5, 29.6, 29.4, 29.3, 29.2, 29.2, 27.2, 26.0, 26.0, 25.6, 22.6, 14.1.

Intermediate 1b: (2,5-bis((9Z,12Z)-octadeca-9,12-dien-1-yloxy)phenyl)methanol

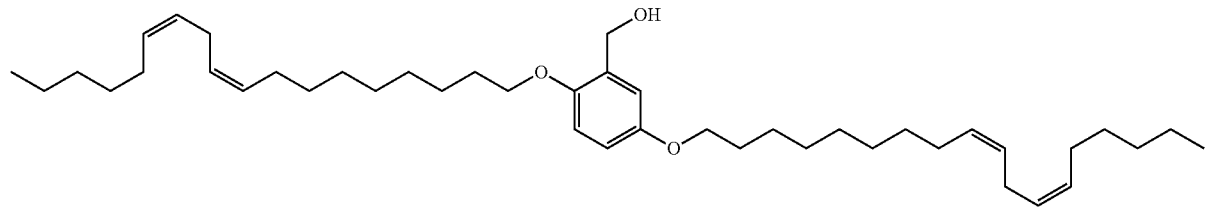 [SMILES: CCCCC/C=C\C/C=C\CCCCCCCCOc1ccc(OCCCCCCCC/C=C\C/C=C\CCCCC)c(CO)c1]

To a solution of Intermediate 1a (1.165 g, 1.835 mmol) in THF (10 ml) and Methanol (5 ml) was added NaBH$_4$ (0.090 g, 2.385 mmol) and stirred for 16 h at room temp. Reaction was diluted with 100 ml ethyl acetate and 100 ml water. Organic layer was separated, washed with 2×50 ml water, dried over Na$_2$SO$_4$ and concentrated under reduced pressure to give crude product. Crude product was purified by silica gel chromatography eluting with 10-90% ethyl acetate: heptane to afford desired product as a colorless oil (0.75 g, 64% yield). $^1$H NMR (400 MHz, CDCl$_3$) δ: 6.86 (d, J=2.0 Hz, 1H), 6.76-6.80 (m, 2H), 5.27-5.48 (m, 8H), 4.66 (s, 2H), 3.96 (t, J=6.5 Hz, 2H), 3.91 (t, J=6.8 Hz, 2H), 2.79 (t, J=6.5 Hz, 4H), 2.06 (q, J=6.9 Hz, 8H), 1.77 (dquin, J=14.2, 7.0 Hz, 4H), 1.41-1.54 (m, J=7.5, 5.5 Hz, 4H), 1.23-1.41 (m, 28H), 0.90 (t, J=7.0 Hz, 6H). $^{13}$C NMR (400 MHz, CDCl$_3$) δ: 153.0, 150.9, 130.2, 130.1, 130.1, 130.1, 128.0, 128.0, 127.9, 115.4, 113.7, 112.0, 68.6, 68.5, 62.5, 31.5, 29.6, 29.5, 29.4, 29.3, 29.2, 27.2, 27.2, 26.1, 26.0, 25.6, 22.6, 14.1.

Example 1: 2,5-bis((9Z,12Z)-octadeca-9,12-dien-1-yloxy)benzyl 4-(dimethylamino)butanoate

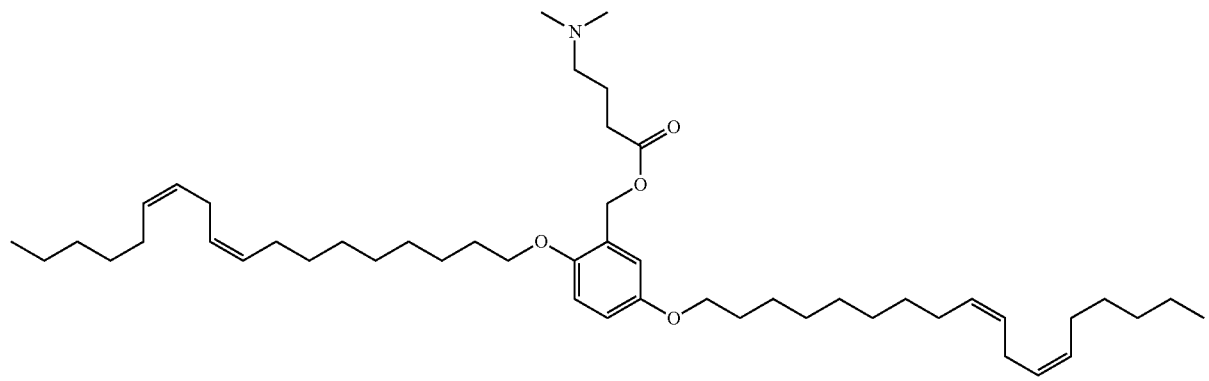 [SMILES: CCCCC/C=C\C/C=C\CCCCCCCCOc1ccc(OCCCCCCCC/C=C\C/C=C\CCCCC)c(COC(=O)CCCN(C)C)c1]

To a solution of 4-(dimethylamino)butanoic acid (26.3 mg, 0.157 mmol) in DCM (25 ml) was added EDC.HCl (45.1 mg, 0.235 mmol) and DMAP (1.918 mg, 0.016 mmol) followed by NEt$_3$ (0.087 ml, 0.628 mmol) and stirred for 30 min at room temp. To the mixture was added Intermediate 1b (100 mg, 0.157 mmol) and stirred for 16 h. Reaction was diluted with 100 ml dichloromethane and 100 ml water. Organic layer was separated, washed with 2×50 ml water, dried over MgSO$_4$ and concentrated under reduced pressure to give crude product. Crude product was purified by silica gel chromatography on Biotage purification system eluting with 10-90% ethyl acetate: heptane to afford desired product as colorless oil (84 mg, 71% yield).

$^1$H NMR (400 MHz, DICHLOROMETHANE-d$_2$) δ: 6.90 (d, J=2.5 Hz, 1H), 6.78-6.85 (m, 2H), 5.28-5.54 (m, 8H), 5.14 (s, 2H), 3.85-4.01 (m, 4H), 2.82 (t, J=6.5 Hz, 4H), 2.42 (t, J=7.3 Hz, 2H), 2.30 (t, J=7.0 Hz, 2H), 2.21 (s, 6H), 2.01-2.15 (m, 8H), 1.69-1.88 (m, 6H), 1.44-1.57 (m, 4H), 1.26-1.44 (m, 28H), 0.93 (t, J=7.0 Hz, 6H). $^{13}$C NMR (400 MHz, DICHLOROMETHANE-d$_2$) δ: 173.8, 153.4, 151.4, 130.6, 130.6, 128.5, 128.4, 126.3, 116.4, 114.6, 113.0, 69.4, 69.0, 61.9, 59.2, 45.7, 32.5, 32.1, 30.2, 30.1, 30.0, 30.0, 29.9, 29.8, 29.8, 27.7, 27.7, 26.6, 26.6, 26.1, 23.5, 23.1, 14.4.

The following example can be prepared using similar coupling methods to those employed for the synthesis of Example 1.

Example 2: 2,5-bis((9Z,12Z)-octadeca-9,12-dien-1-yloxy)benzyl 3-(dimethylamino)propanoate

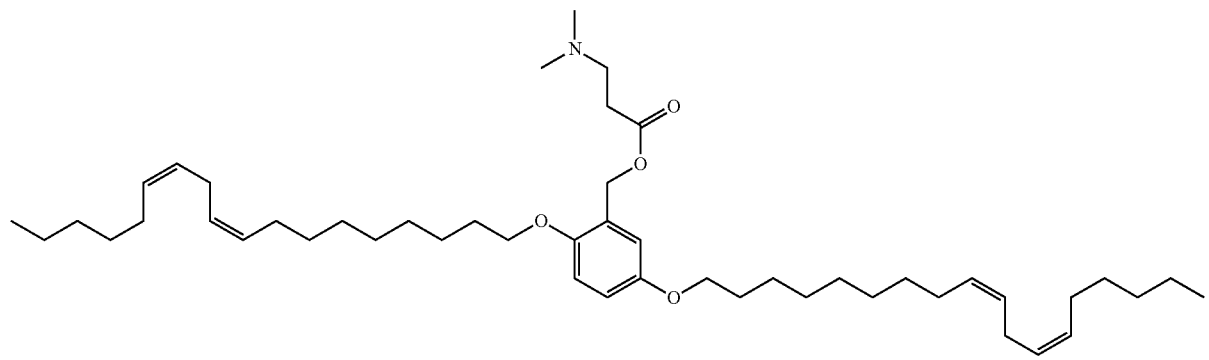 [SMILES: CCCCC/C=C\C/C=C\CCCCCCCCOc1ccc(OCCCCCCCC/C=C\C/C=C\CCCCC)c(COC(=O)CCN(C)C)c1]

Desired product was isolated as colorless oil (120 mg, 69% yield). $^1$H NMR (400 MHz, DICHLOROMETHANE-$d_2$) δ: 6.92 (d, J=2.5 Hz, 1H), 6.81-6.84 (m, 2H), 5.32-5.48 (m, 9H), 5.15 (s, 2H), 3.84-4.03 (m, 4H), 2.82 (t, J=6.5 Hz, 4H), 2.61-2.70 (m, 2H), 2.50-2.61 (m, 2H), 2.25 (s, 6H), 2.09 (q, J=6.9 Hz, 7H), 1.72-1.84 (m, 4H), 1.44-1.56 (m, 4H), 1.26-1.44 (m, 28H), 0.93 (t, J=7.0 Hz, 6H). $^{13}$C NMR (400 MHz, DICHLOROMETHANE-$d_2$) δ: 172.8, 153.5, 151.4, 130.6, 130.6, 128.5, 128.4, 126.2, 116.3, 114.6, 113.0, 69.4, 69.0, 62.0, 55.4, 45.6, 33.6, 32.1, 30.2, 30.2, 30.1, 30.0, 29.9, 29.9, 29.8, 29.8, 27.7, 27.7, 26.6, 26.6, 26.1, 23.1, 14.4.

Scheme 2

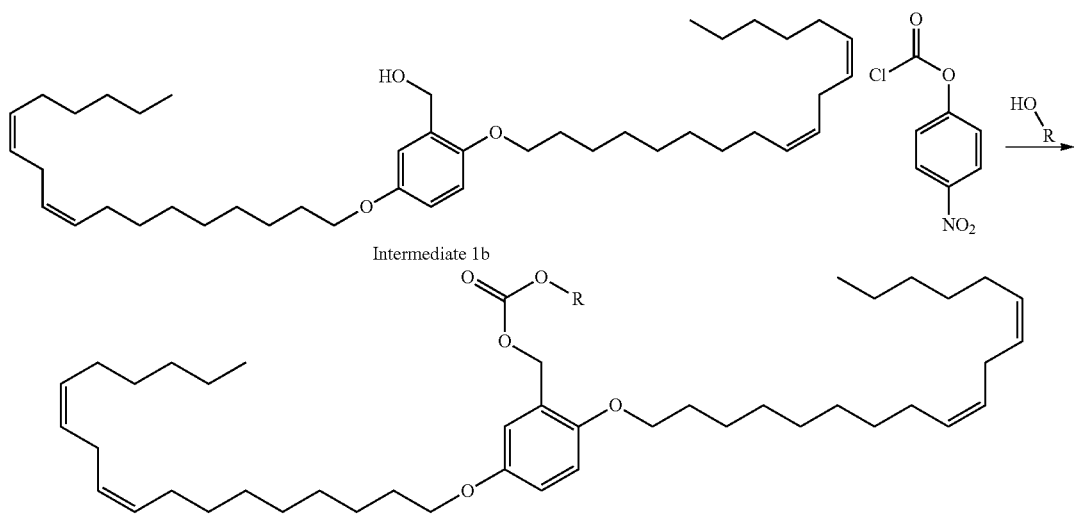

R is an optionally substituted alkylene-amine, heterocyclyl or heterocyclyl-alkyl Synthesis of Example 3: 2,5-bis((9Z,12Z)-octadeca-9,12-dienyloxy)benzyl 3-(dimethylamino)propyl Carbonate

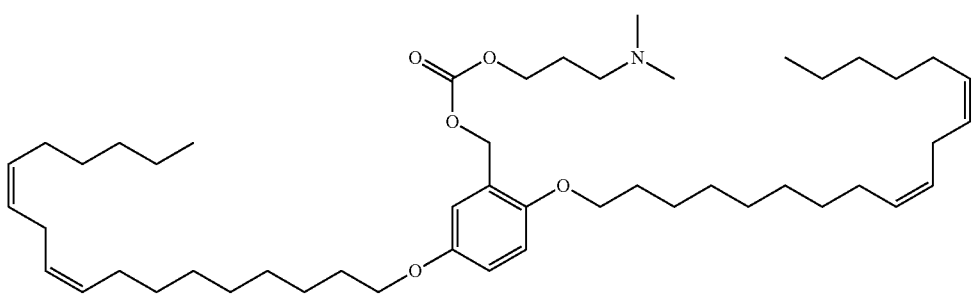 [SMILES: CCCCC/C=C\C/C=C\CCCCCCCCOc1ccc(OCCCCCCCC/C=C\C/C=C\CCCCC)c(COC(=O)OCCCN(C)C)c1]

To a solution of Intermediate 1b (150 mg, 0.235 mmol) in dry CDCl$_3$ (2 mL) was added para-nitrophenylchloroformate (61.7 mg, 0.306 mmol) followed by pyridine (23.1 μL, 0.286 mmol). The reaction was stirred at 50° C. After 4 h the reaction was concentrated under reduced pressure and re-dissolved in 2 mL DCM. N,N-dimethylaminopropanol (121 mg, 1.18 mmol) was added followed by DMAP (5.75 mg, 0.047 mmol). The reaction was stirred at room temperature. After 18 h the reaction was quenched with 2 mL water and extracted into additional 3×5 mL DCM. The combined organic layers were concentrated under reduced pressure and purified by silica gel chromatography on ISCO purification system eluting with MeOH/DCM (0 to 3%) to provide 141.3 mg (78%) of desired product as a clear oil. $^1$H NMR (400 MHz, CHLOROFORM-d) δ: 6.95 (d, J=2.0 Hz, 1H), 6.78-6.83 (m, 2H), 5.29-5.48 (m, 8H), 5.22 (s, 2H), 4.24 (t, J=6.6 Hz, 2H), 3.94 (dt, J=9.6, 6.6 Hz, 4H), 2.81 (t, J=6.3 Hz, 4H), 2.38 (t, J=7.3 Hz, 2H), 2.24 (s, 6H), 2.08 (q, J=6.6 Hz, 8H), 1.87 (quin, J=6.9 Hz, 2H), 1.78 (m, 4H), 1.28-1.52 (m, 32H), 0.92 (t, J=6.6 Hz, 6H). MS (m+1)=766.5, Rt=1.22 min (LC Method 1).

The following example can be prepared using similar coupling methods to those employed for the synthesis of Example 3

Example 4: 2,5-bis((9Z,12Z)-octadeca-9,12-dienyloxy)benzyl 3-(diethylamino)propyl Carbonate

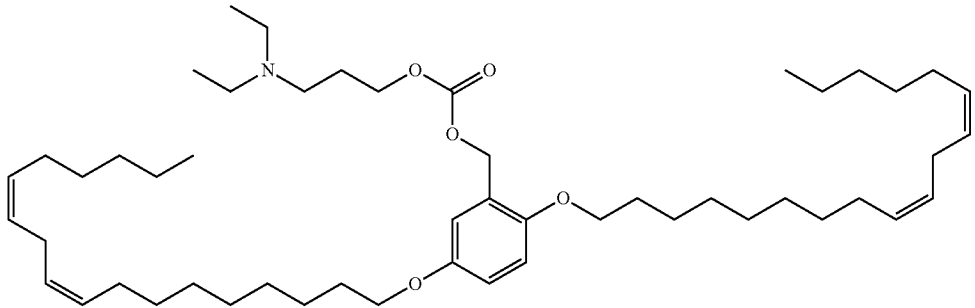 [SMILES: CCCCC/C=C\C/C=C\CCCCCCCCOc1ccc(OCCCCCCCC/C=C\C/C=C\CCCCC)c(COC(=O)OCCCN(CC)CC)c1]

$^1$H NMR (400 MHz, CHLOROFORM-d) δ: 6.95 (d, J=2.0 Hz, 1H), 6.77-6.84 (m, 2H), 5.30-5.48 (m, 8H), 5.22 (s, 2H), 4.24 (t, J=6.6 Hz, 2H), 3.94 (dt, J=9.1, 6.6 Hz, 4H), 2.81 (t, J=6.3 Hz, 4H), 2.53 (q, J=7.1 Hz, 6H), 2.08 (q, J=6.6 Hz, 8H), 1.71-1.91 (m, 6H), 1.44-1.53 (m, 4H), 1.26-1.44 (m, 28H), 1.03 (t, J=7.1 Hz, 6H), 0.92 (t, J=7.1 Hz, 6H). MS (m+1)=794.5, Rt=1.38 min (LC Method 1).

Scheme 3:
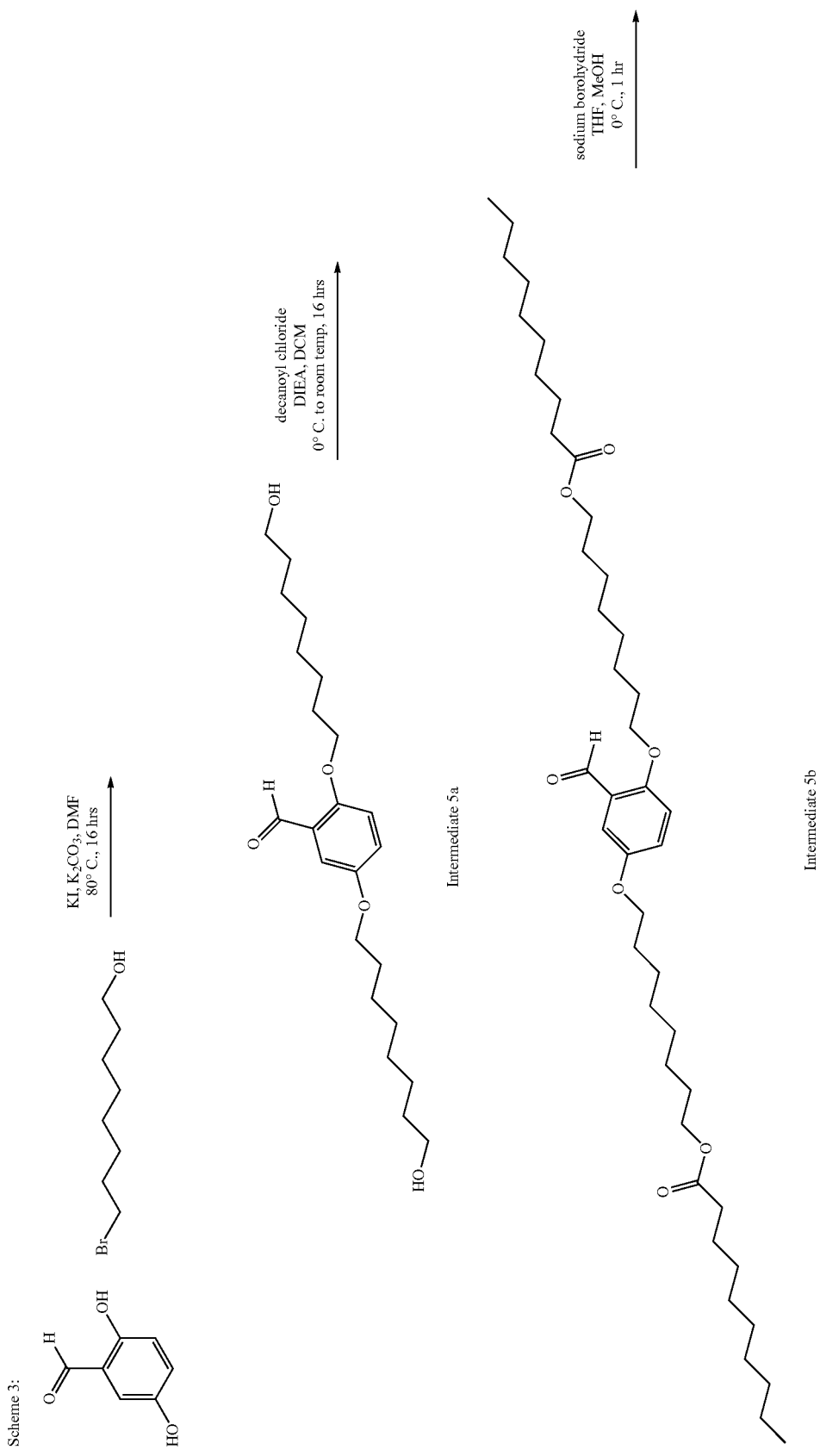

-continued
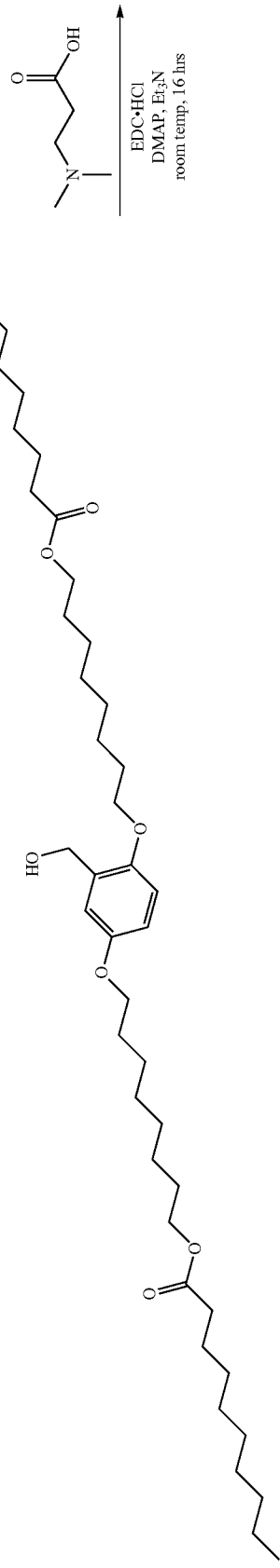
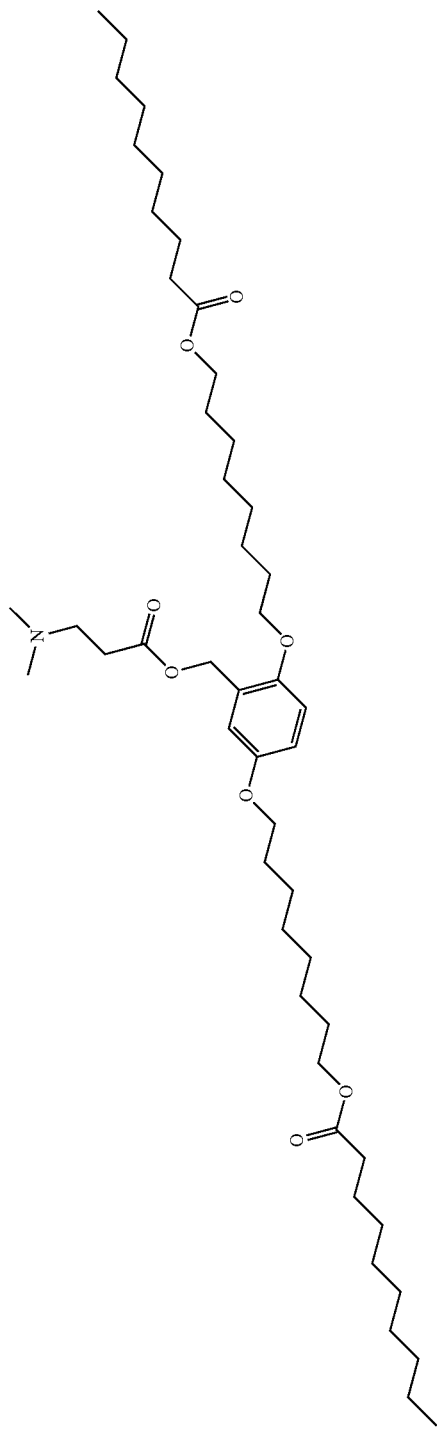
Intermediate 5c

Synthesis of Example 5: 2,5-bis((9Z,12Z)-octadeca-9,12-dien-1-yloxy)benzyl 4-(dimethylamino)butanoate Intermediate 5a: 2,5-bis((8-hydroxyoctyl)oxy)benzaldehyde

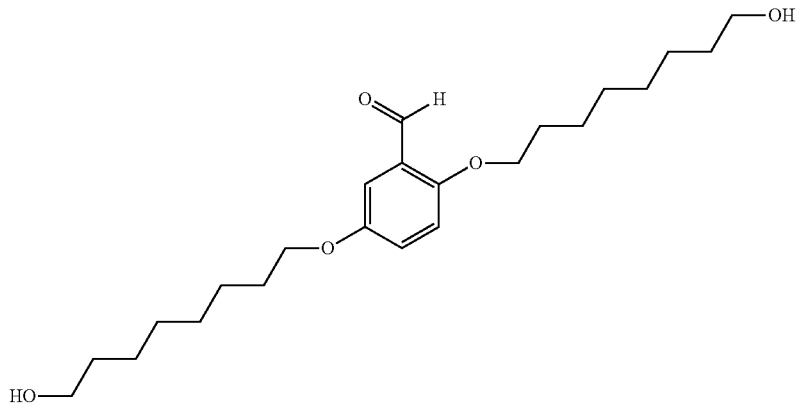 [SMILES: O=Cc1cc(OCCCCCCCCO)ccc1OCCCCCCCCO]

To a solution of 2,5-dihydroxybenzaldehyde (1 g, 7.24 mmol) in DMF (15 mL) was added 8-bromooctan-1-ol (3.03 g, 14.48 mmol), $K_2CO_3$ (5.00 g, 36.2 mmol) and KI (0.012 g, 0.072 mmol) and heated to 80° C. for 16 h. Reaction was diluted with 100 ml ethyl acetate and 100 ml water. Organic layer was separated, washed with 2×50 ml water, dried over $Na_2SO_4$ and concentrated under reduced pressure to give crude product. Crude product was purified by prep-HPLC chromatography eluting with 10-90% acetonitrile: water and 0.1% TFA to afford desired product (550 mg, 19% yield). $^1$H NMR (400 MHz, CHLOROFORM-d) δ: 10.47 (s, 1H), 7.31 (d, J=3.0 Hz, 1H), 7.11 (dd, J=9.0, 3.3 Hz, 1H), 6.92 (d, J=9.0 Hz, 1H), 4.03 (t, J=6.4 Hz, 2H), 3.94 (t, J=6.5 Hz, 2H), 3.65 (t, J=6.7 Hz, 4H), 1.69-1.79 (m, 4H), 1.52-1.65 (m, 4H), 1.43-1.50 (m, 4H), 1.30-1.40 (m, 12H). $^{13}$C NMR (400 MHz, CHLOROFORM-d) δ: 189.9, 156.3, 152.9, 124.9, 124.2, 114.3, 110.7, 69.1, 68.6, 63.0, 63.0, 32.7, 32.7, 29.3, 29.1, 26.0, 25.9, 25.6.

Intermediate 5b: ((2-formyl-1,4-phenylene)bis(oxy))bis(octane-8,1-diyl) bis(decanoate)

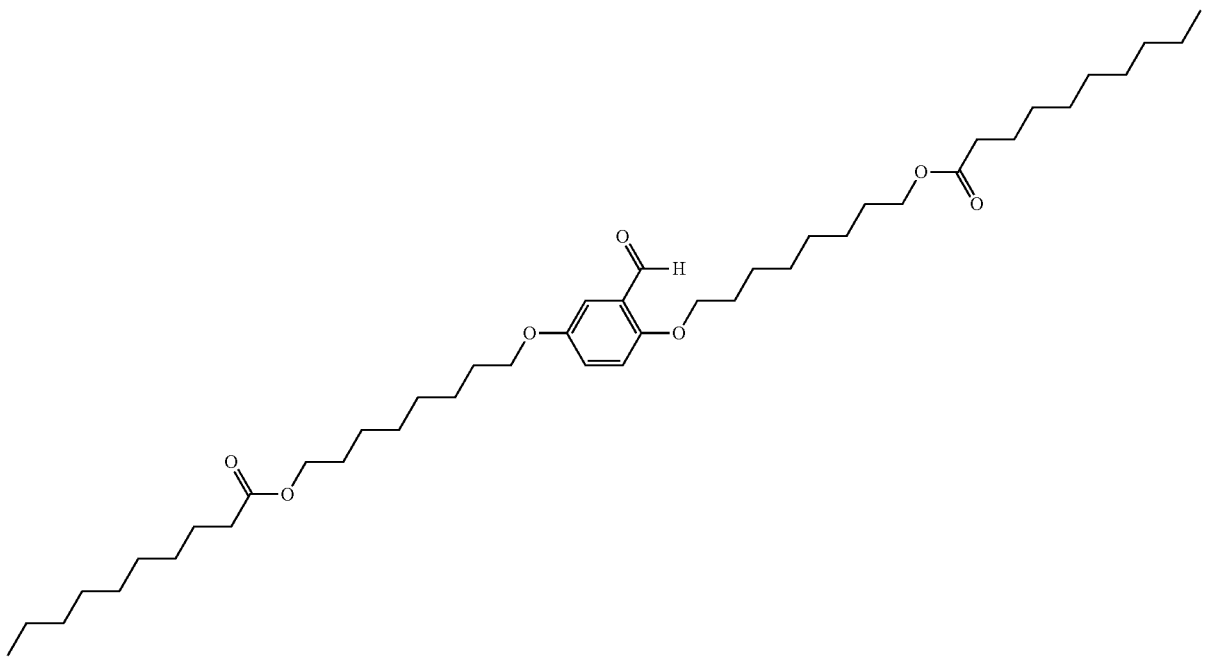 [SMILES: CCCCCCCCCC(=O)OCCCCCCCCOc1ccc(OCCCCCCCCOC(=O)CCCCCCCCC)c(C=O)c1]

To a solution of Intermediate 5a (455 mg, 1.153 mmol) in DCM (11.5 mL) was added decanoyl chloride (484 mg, 2.54 mmol) followed by addition of DIEA (1.01 mL, 5.77 mmol) at room temp and stirred for 16 h. Reaction was diluted with 100 ml dichloromethane and 100 ml water. Organic layer was separated, washed with 50 ml water, dried over $MgSO_4$ and concentrated under reduced pressure to give crude product. Crude product was purified by silica gel chromatography on ISCO purification system eluting with 10-90% ethyl acetate: heptane to afford desired product (591 mg, 73% yield). $^1$H NMR (400 MHz, CHLOROFORM-d) δ: 10.47 (s, 1H), 7.31 (d, J=3.3 Hz, 1H), 7.12 (dd, J=9.0, 3.3 Hz, 1H), 6.93 (d, J=9.0 Hz, 1H), 3.99-4.12 (m, 6H), 3.94 (t, J=6.5 Hz, 2H), 2.30 (t, J=7.5 Hz, 4H), 1.72-1.95 (m, 4H), 1.11-1.54 (m, 48H), 0.81-0.96 (m, 6H). $^{13}$C NMR (400 MHz, CHLOROFORM-d) δ: 189.8, 179.0, 174.1, 156.3, 152.9, 125.0, 124.2, 114.3, 69.1, 68.6, 64.3, 34.4, 31.8, 29.5, 29.4, 29.4, 29.2, 29.2, 28.6, 26.0, 25.9, 25.9, 25.0, 24.7, 22.7, 14.1.

Intermediate 5c: ((2-(hydroxymethyl)-1,4-phenylene)bis(oxy))bis(octane-8,1-diyl) bis(decanoate)

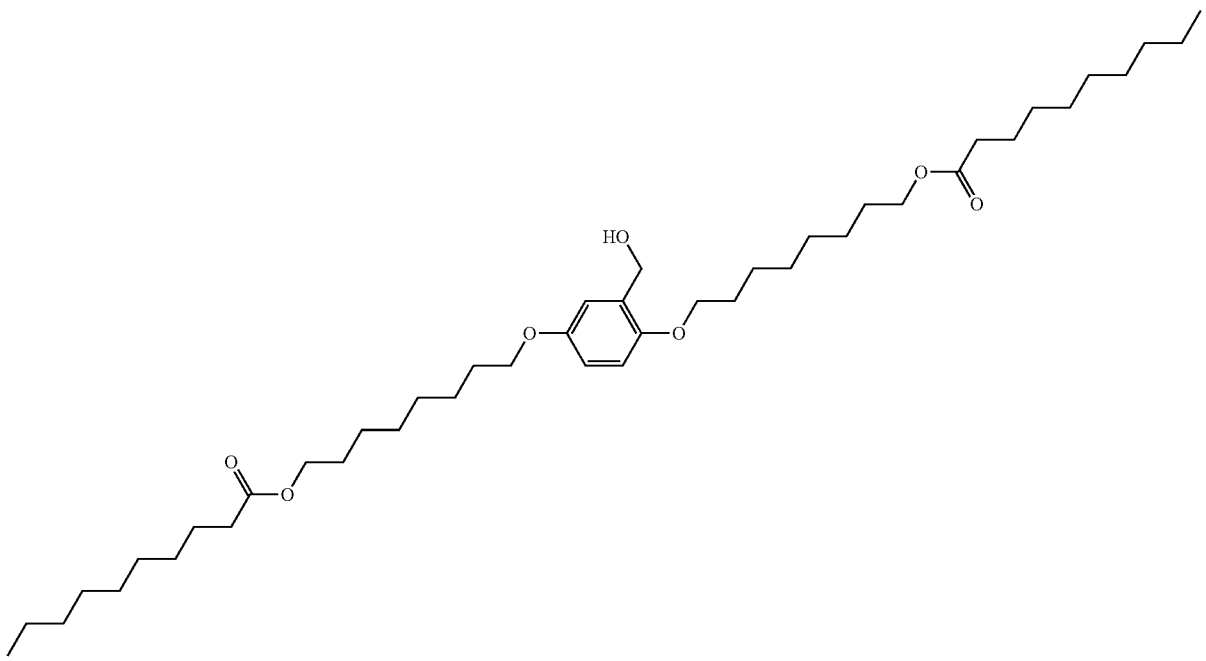 [SMILES: CCCCCCCCCC(=O)OCCCCCCCCOc1ccc(OCCCCCCCCOC(=O)CCCCCCCCC)c(CO)c1]

To a solution of Intermediate 5b (590 mg, 0.839 mmol) in tetrahydrofuran (4.2 mL) and methanol (4.2 mL) was added sodium borohydride (31.7 mg, 0.839 mmol) at 0° C. and stirred for 1 h. Reaction was diluted with 100 ml ethyl acetate and 50 ml water. Organic layer was separated, washed with 50 ml water, dried over $Na_2SO_4$ and concentrated under reduced pressure to give crude product. Crude product was purified by silica gel chromatography on ISCO purification system eluting with 10-90% ethyl acetate: heptane to afford desired product (450 mg, 76% yield). $^1$H NMR (400 MHz, CHLOROFORM-d) δ: 6.87 (d, J=2.5 Hz, 1H), 6.76-6.79 (m, 2H), 4.66 (s, 2H), 4.06 (t, J=6.8 Hz, 4H), 3.96 (t, J=6.5 Hz, 2H), 3.91 (t, J=6.5 Hz, 2H), 2.30 (t, J=7.5 Hz, 4H), 1.70-1.86 (m, 4H), 1.62 (t, J=7.0 Hz, 8H), 1.41-1.52 (m, 4H), 1.14-1.40 (m, 36H), 0.80-0.95 (m, 6H). $^{13}$C NMR (400 MHz, CHLOROFORM-d) δ: 174.1, 153.0, 150.9, 130.1, 115.3, 113.7, 112.0, 68.5, 68.4, 64.3, 64.3, 62.4, 34.4, 31.8, 29.4, 29.4, 29.3, 29.3, 29.2, 29.1, 28.6, 26.1, 26.0, 25.8, 25.0, 24.7, 22.7, 14.1.

Example 5: ((2-(((3-(dimethylamino)propanoyl)oxy)methyl)-1,4-phenylene)bis(oxy))bis(octane-8,1-diyl) bis(decanoate

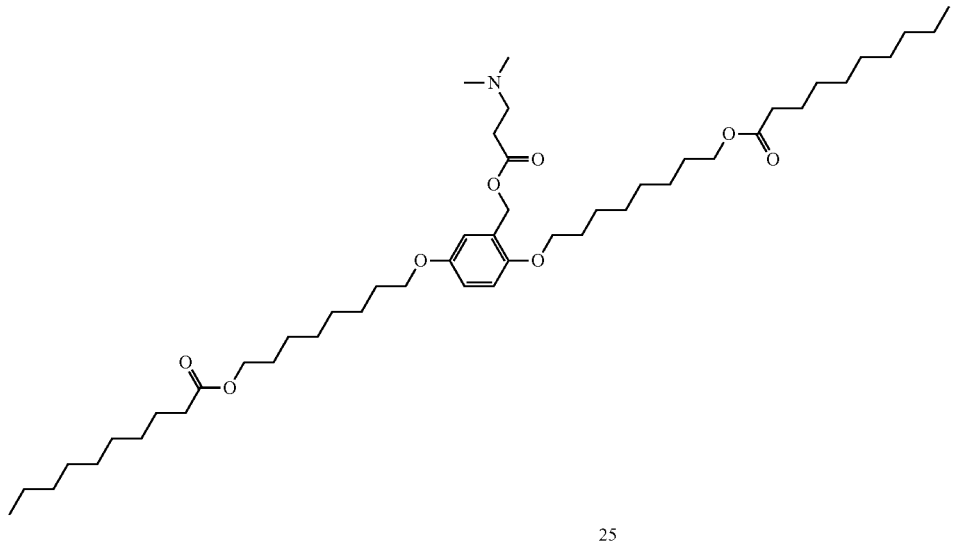

A mixture of Intermediate 5c (65 mg, 0.092 mmol), 3-(dimethylamino)propanoic acid (16. mg, 0.138 mmol), EDC.HCl (35. mg, 0.184 mmol) and DIEA (32.2 μl, 0.184 mmol) in DCM (Volume: 922 μl) was stirred at 0° C. for 16 h while letting it warm to room temp. Reaction was diluted with 20 ml dichloromethane and 20 ml water. Organic layer was separated, washed with 2×20 ml water, dried over $MgSO_4$ and concentrated under reduced pressure to give crude product. Crude product was purified by silica gel chromatography on ISCO purification system eluting with 10-90% ethyl acetate: heptane to afford desired product as a colorless oil (40 mg, 51% yield). $^1$H NMR (400 MHz, CHLOROFORM-d) δ: 6.91 (s, 1H), 6.79 (d, J=1.5 Hz, 2H), 5.17 (s, 2H), 4.06 (t, J=6.7 Hz, 4H), 3.91 (q, J=6.8 Hz, 4H), 2.61-2.73 (m, 2H), 2.50-2.60 (m, 2H), 2.30 (t, J=7.5 Hz, 4H), 2.26 (s, 6H), 1.70-1.83 (m, 4H), 1.52-1.69 (m, 8H), 1.42-1.48 (m, 4H), 1.18-1.35 (m, 36H), 0.79-0.95 (m, 6H). $^{13}$C NMR (400 MHz, CHLOROFORM-d) δ: 174.0, 172.3, 152.8, 150.9, 125.4, 116.0, 114.3, 112.5, 68.8, 68.5, 64.3, 61.7, 54.7, 45.2, 34.4, 32.9, 31.8, 29.4, 29.3, 29.3, 29.2, 29.2, 29.1, 28.6, 26.0, 26.0, 25.9, 25.9, 25.0, 22.7, 14.1.

The following examples can be prepared using similar coupling methods to those employed for the synthesis of Example 5.

Example 6: ((2-(((1-methylpiperidine-4-carbonyl)oxy)methyl)-1,4-phenylene)bis(oxy))bis(octane-8,1-diyl) bis(decanoate)

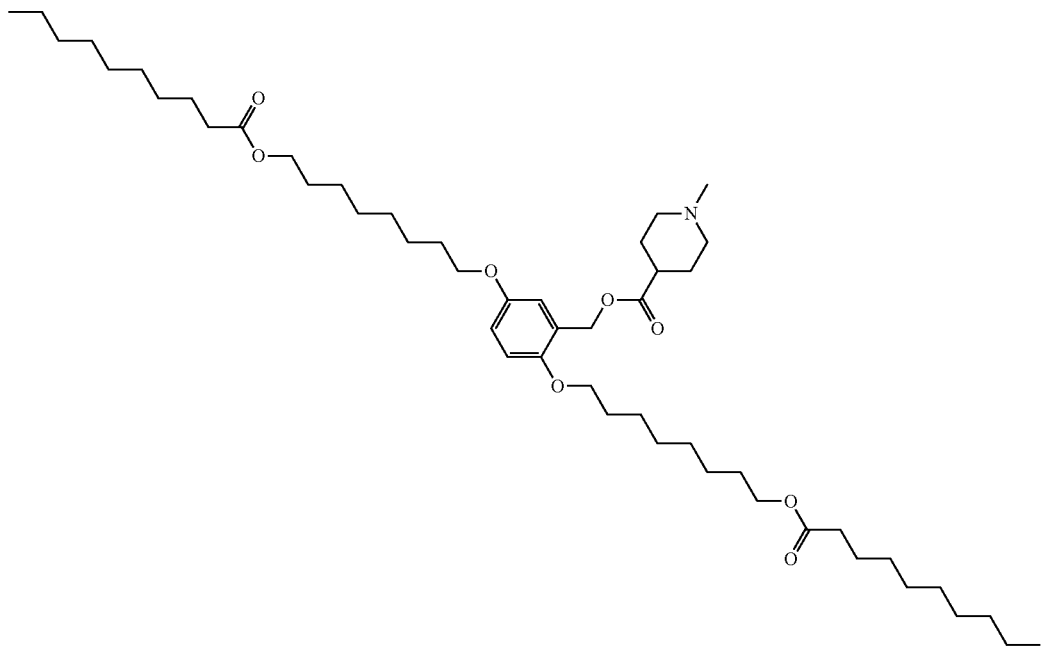

Desired product was isolated as colorless oil (72 mg, 77% yield). $^1$H NMR (400 MHz, CHLOROFORM-d) δ: 6.87 (s, 1H), 6.78 (s, 2H), 5.14 (s, 2H), 4.06 (t, J=6.7 Hz, 4H), 3.90 (q, J=6.3 Hz, 4H), 2.85 (d, J=11.3 Hz, 2H), 2.19-2.44 (m, 8H), 2.03-2.15 (m, 2H), 1.99 (d, J=11.8 Hz, 2H), 1.81-1.91 (m, 2H), 1.70-1.80 (m, 4H), 1.58-1.66 (m, 8H), 1.40-1.52 (m, 4H), 1.14-1.39 (m, 36H), 0.88 (t, J=6.5 Hz, 6H). $^{13}$C NMR (400 MHz, CHLOROFORM-d) δ: 174.7, 174.0, 152.8, 150.9, 125.5, 115.9, 114.2, 112.4, 68.7, 68.5, 64.3, 61.7, 54.8, 46.2, 34.4, 31.8, 29.7, 29.4, 29.3, 29.2, 29.2, 29.1, 28.6, 28.0, 26.0, 25.9, 25.0, 22.6, 14.1.

Example 7: ((2-(((4-(dimethylamino)butanoyl)oxy)methyl)-1,4-phenylene)bis(oxy))bis(octane-8,1-diyl) bis(decanoate)

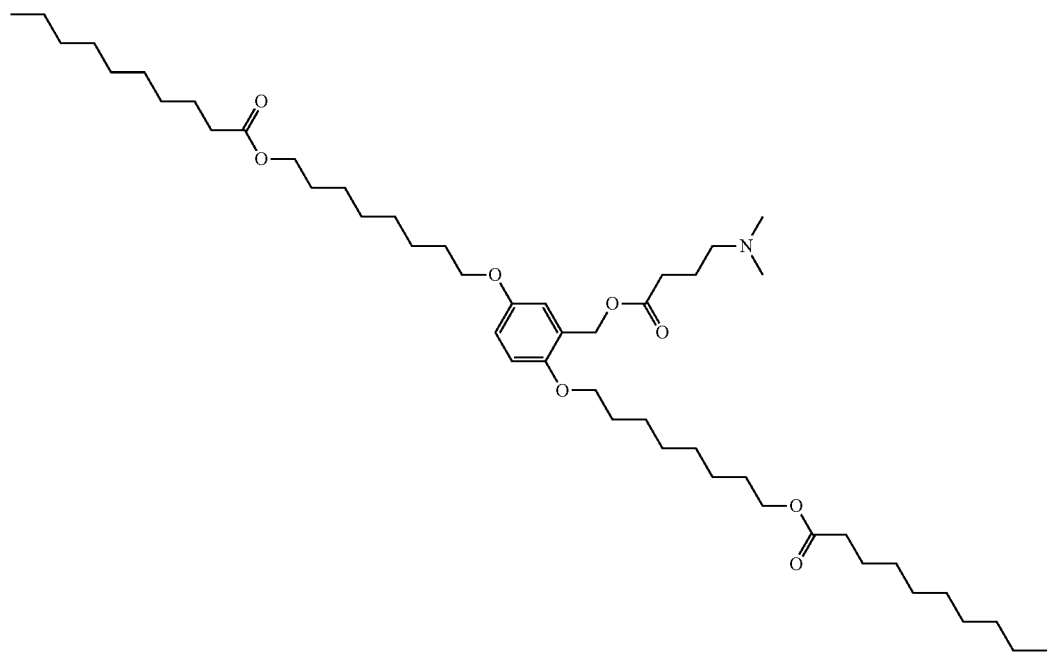 [SMILES: CCCCCCCCCC(=O)OCCCCCCCCOc1ccc(OCCCCCCCCOC(=O)CCCCCCCCC)c(COC(=O)CCCN(C)C)c1]

Desired product was isolated as a colorless oil (40 mg, 50% yield). $^1$H NMR (400 MHz, CHLOROFORM-d) δ: 6.90 (s, 1H), 6.78 (d, J=1.5 Hz, 2H), 5.15 (s, 2H), 4.06 (t, J=6.7 Hz, 4H), 3.91 (q, J=6.5 Hz, 4H), 2.42 (t, J=7.4 Hz, 2H), 2.28-2.34 (m, 6H), 2.24 (s, 6H), 1.84 (quin, J=7.5 Hz, 2H), 1.70-1.80 (m, 4H), 1.53-1.69 (m, 8H), 1.42-1.48 (m, 4H), 1.15-1.40 (m, 36H), 0.79-0.94 (m, 6H). $^{13}$C NMR (400 MHz, CHLOROFORM-d) δ: 174.0, 173.4, 152.8, 150.9, 125.5, 115.9, 114.2, 112.5, 68.8, 68.5, 64.3, 61.6, 58.8, 45.3, 34.4, 32.1, 31.8, 29.4, 29.3, 29.3, 29.2, 29.1, 28.6, 26.0, 26.0, 25.9, 25.9, 25.0, 22.9, 22.7, 14.1.

Example 8: ((2-(((1-ethylpiperidine-4-carbonyl)oxy)methyl)-1,4-phenylene)bis(oxy))bis(octane-8,1-diyl) bis(decanoate)

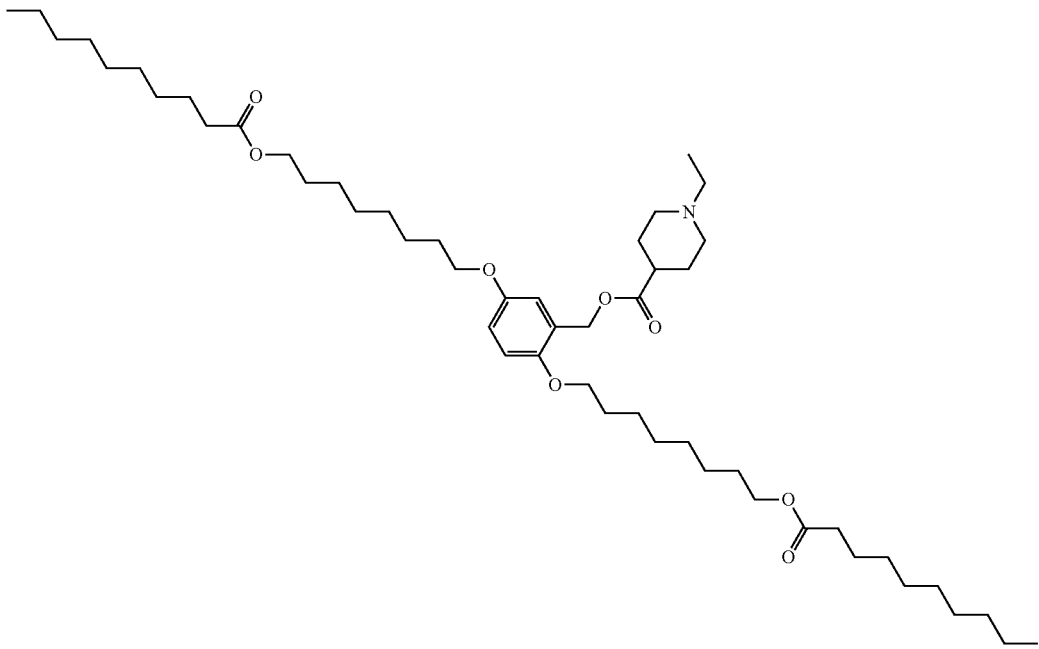 [SMILES: CCCCCCCCCC(=O)OCCCCCCCCOc1ccc(OCCCCCCCCOC(=O)CCCCCCCCC)c(COC(=O)C2CCN(CC)CC2)c1]

Desired product was isolated as a colorless oil (65 mg, 73%). $^1$H NMR (400 MHz, CHLOROFORM-d) δ: 6.87 (s, 1H), 6.78 (d, J=1.5 Hz, 2H), 5.14 (s, 2H), 4.06 (t, J=6.7 Hz, 4H), 3.90 (q, J=6.4 Hz, 4H), 2.92 (d, J=10.8 Hz, 2H), 2.41 (dt, J=13.9, 6.8 Hz, 3H), 2.29 (t, J=7.7 Hz, 4H), 1.98 (d, J=12.0 Hz, 4H), 1.80-1.91 (m, 2H), 1.69-1.80 (m, 4H), 1.53-1.68 (m, 8H), 1.40-1.50 (m, 4H), 1.16-1.39 (m, 36H), 1.10 (t, J=7.2 Hz, 3H), 0.79-0.94 (m, 6H). $^{13}$C NMR (400 MHz, CHLOROFORM-d) δ: 174.8, 174.0, 152.8, 150.8, 125.5, 115.8, 114.1, 112.4, 68.7, 68.5, 64.3, 61.6, 52.5, 34.4, 31.8, 29.4, 29.3, 29.2, 29.2, 29.2, 29.1, 28.6, 28.1, 26.0, 26.0, 25.9, 25.8, 25.0, 22.6, 14.1, 11.9.

Example 9: ((2-(((1-isopropylpiperidine-4-carbonyl)oxy)methyl)-1,4-phenylene)bis(oxy))bis(octane-8,1-diyl) bis(decanoate)

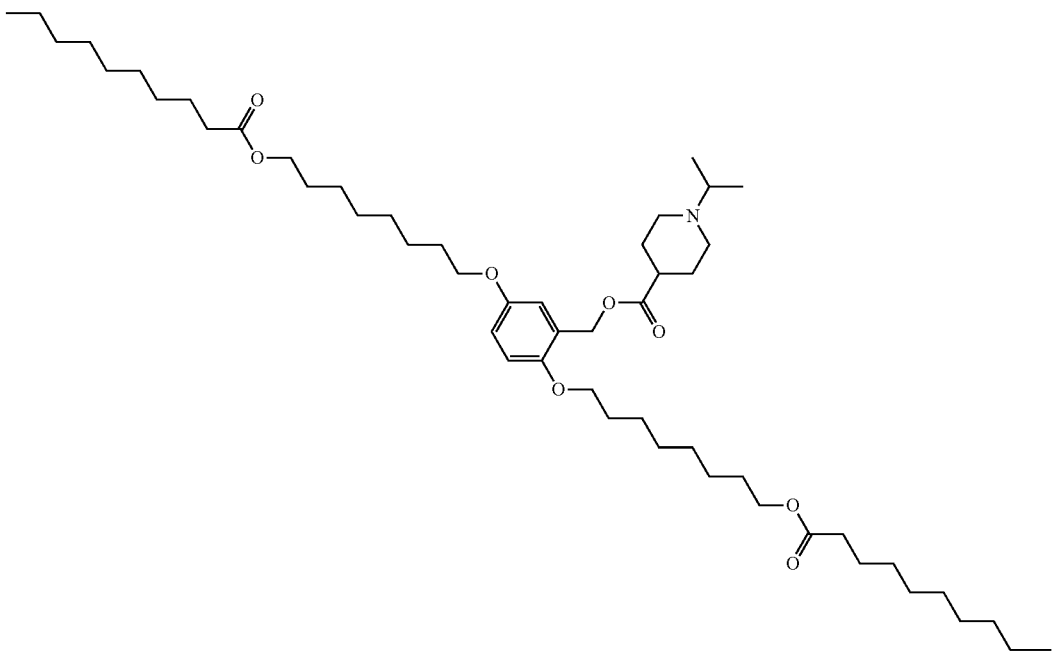 [SMILES: CCCCCCCCCC(=O)OCCCCCCCCOc1ccc(OCCCCCCCCOC(=O)CCCCCCCCC)c(COC(=O)C2CCN(C(C)C)CC2)c1]

The desired product was isolated as a colorless oil (62 mg, 69%). ¹H NMR (400 MHz, CHLOROFORM-d) δ: 6.87 (s, 1H), 6.78 (d, J=1.5 Hz, 2H), 5.14 (s, 2H), 4.06 (t, J=6.7 Hz, 4H), 3.90 (q, J=6.4 Hz, 4H), 2.88 (d, J=11.3 Hz, 2H), 2.72-2.77 (m, 1H), 2.20-2.38 (m, 7H), 1.98 (br. s., 2H), 1.84 (br. s., 1H), 1.69-1.79 (m, 5H), 1.54-1.68 (m, 8H), 1.42-1.46 (m, 4H), 1.16-1.39 (m, 36H), 1.06 (d, J=5.3 Hz, 6H), 0.81-0.93 (m, 6H). ¹³C NMR (400 MHz, CHLOROFORM-d) δ: 174.0, 152.8, 150.8, 125.5, 115.9, 114.1, 112.4, 68.7, 68.5, 64.3, 61.6, 48.0, 34.4, 31.8, 29.4, 29.3, 29.2, 29.2, 29.2, 29.1, 28.6, 26.0, 26.0, 25.9, 25.9, 25.0, 22.6, 18.2, 14.1.

Example 10: ((2-(((4-(pyrrolidin-1-yl)butanoyl)oxy)methyl)-1,4-phenylene)bis(oxy)) bis(octane-8,1-diyl)bis(decanoate)

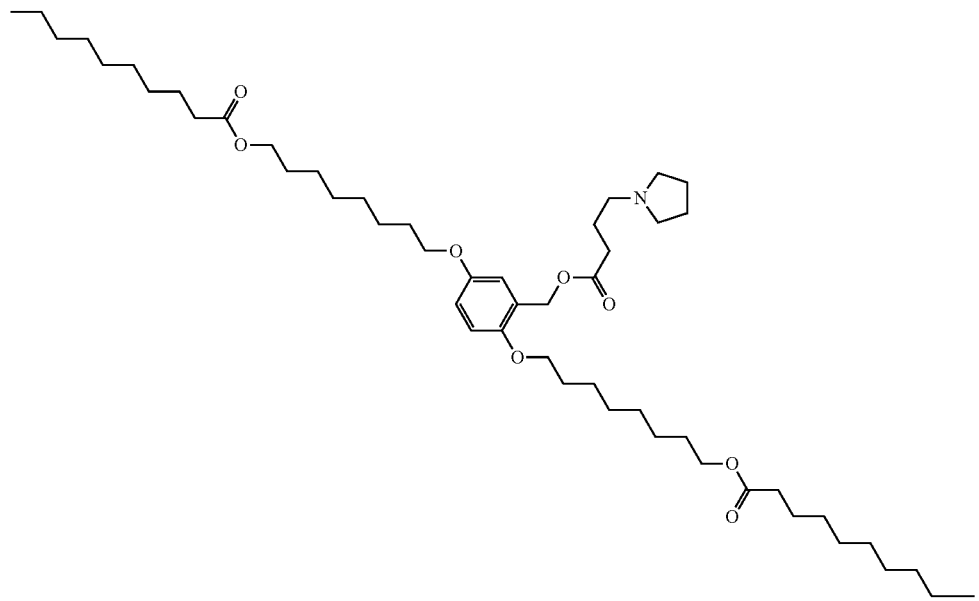 [SMILES: CCCCCCCCCC(=O)OCCCCCCCCOc1ccc(OCCCCCCCCOC(=O)CCCCCCCCC)c(COC(=O)CCCN2CCCC2)c1]

The desired product was isolated as a colorless oil (50 mg, 56%). ¹H NMR (400 MHz, CHLOROFORM-d) δ: 6.86 (s, 1H), 6.79 (s, 2H), 5.14 (s, 2H), 4.05 (t, J=6.7 Hz, 4H), 3.85-3.96 (m, 4H), 3.76-3.84 (m, 2H), 3.10-3.18 (m, 2H), 2.74-2.84 (m, 2H), 2.48 (t, J=6.3 Hz, 2H), 2.29 (t, J=7.5 Hz, 4H), 1.94-2.19 (m, 6H), 1.74 (quin, J=6.8 Hz, 4H), 1.61 (d, J=5.0 Hz, 8H), 1.42 (d, J=7.3 Hz, 4H), 1.15-1.39 (m, 36H), 0.76-0.94 (m, 6H). ¹³C NMR (400 MHz, CHLOROFORM-d) δ: 174.2, 174.2, 172.1, 152.8, 150.9, 124.8, 116.2, 114.6, 112.6, 68.8, 68.5, 64.3, 62.2, 54.4, 53.6, 34.4, 31.8, 30.5, 29.4, 29.3, 29.2, 29.2, 29.1, 28.5, 25.9, 25.8, 25.8, 25.0, 23.2, 22.6, 20.7, 14.1.

Example 11: ((2-((2-(1-methylpiperidin-4-yl)acetoxy)methyl)-1,4-phenylene)bis(oxy))bis(octane-8,1-diyl) bis(decanoate)

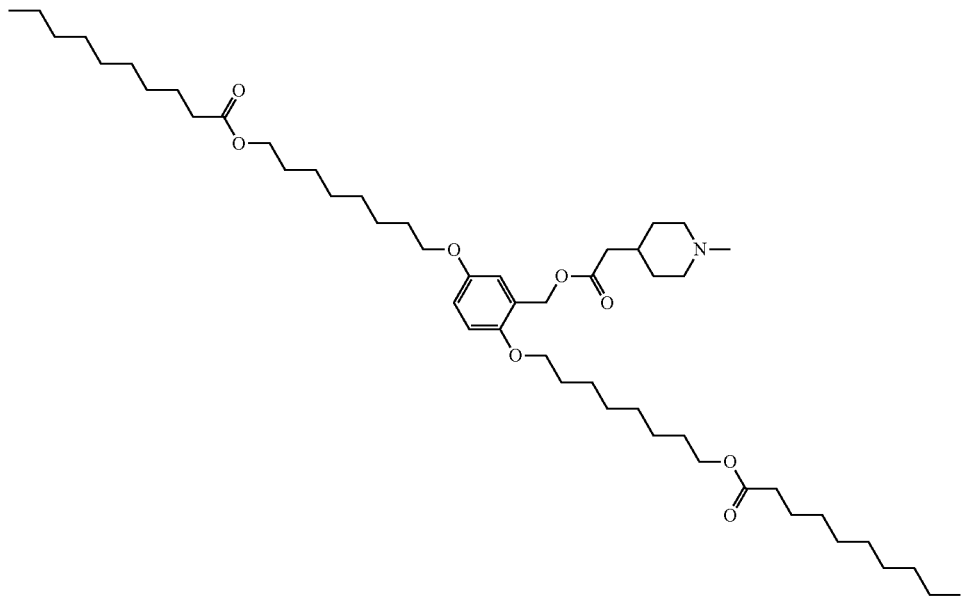 [SMILES: CCCCCCCCCC(=O)OCCCCCCCCOc1ccc(OCCCCCCCCOC(=O)CCCCCCCCC)c(COC(=O)CC2CCN(C)CC2)c1]

The desired product was isolated as a colorless oil (62 mg, 70%). $^1$H NMR (400 MHz, CHLOROFORM-d) δ: 6.88 (s, 1H), 6.78 (d, J=1.3 Hz, 2H), 5.13 (s, 2H), 4.06 (t, J=6.8 Hz, 4H), 3.90 (q, J=6.5 Hz, 4H), 2.87 (d, J=11.3 Hz, 2H), 2.22-2.35 (m, 8H), 2.00 (t, J=11.4 Hz, 2H), 1.69-1.88 (m, 6H), 1.53-1.68 (m, 8H), 1.44 (d, J=4.3 Hz, 4H), 1.18-1.41 (m, 40H), 0.80-0.95 (m, 6H). $^{13}$C NMR (400 MHz, CHLOROFORM-d) δ: 174.0, 172.5, 152.8, 150.9, 125.3, 116.0, 114.4, 112.4, 68.7, 68.5, 64.3, 61.6, 55.5, 46.2, 41.0, 34.4, 32.2, 31.8, 29.4, 29.3, 29.2, 29.2, 29.2, 29.2, 29.1, 28.6, 26.0, 25.9, 25.9, 25.0, 22.6, 14.1.

Scheme 4

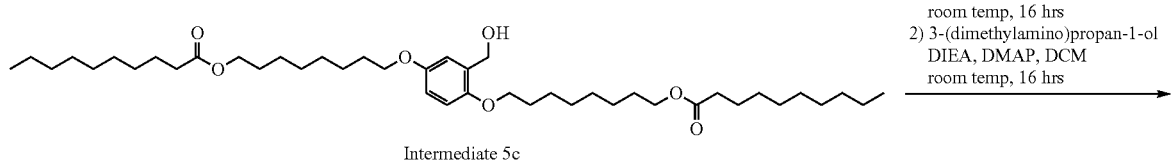

Intermediate 5c 1) 4-nitriphenylchloroformate pyridine, DCM room temp, 16 hrs
2) 3-(dimethylamino)propan-1-ol DIEA, DMAP, DCM room temp, 16 hrs

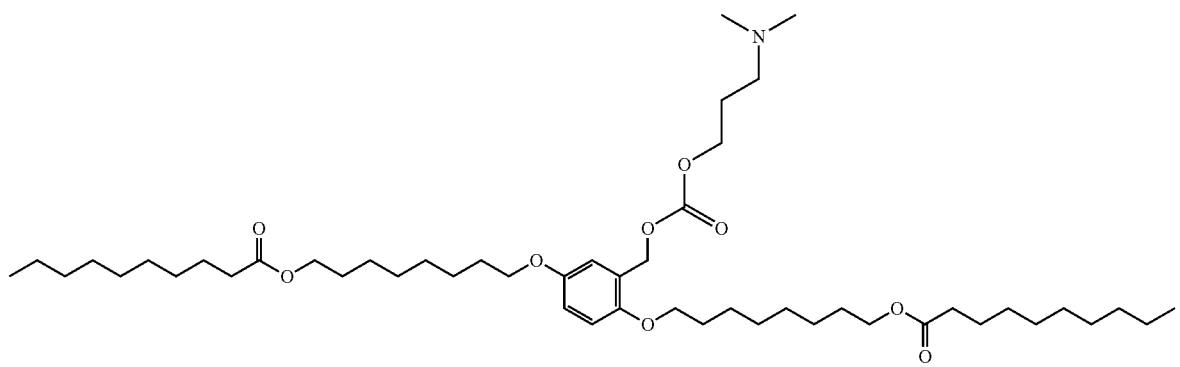

Synthesis of Example 12: ((2-((((3-(dimethylamino) propoxy)carbonyl)oxy)methyl)-1,4-phenylene)bis (oxy))bis(octane-8,1-diyl) bis(decanoate)

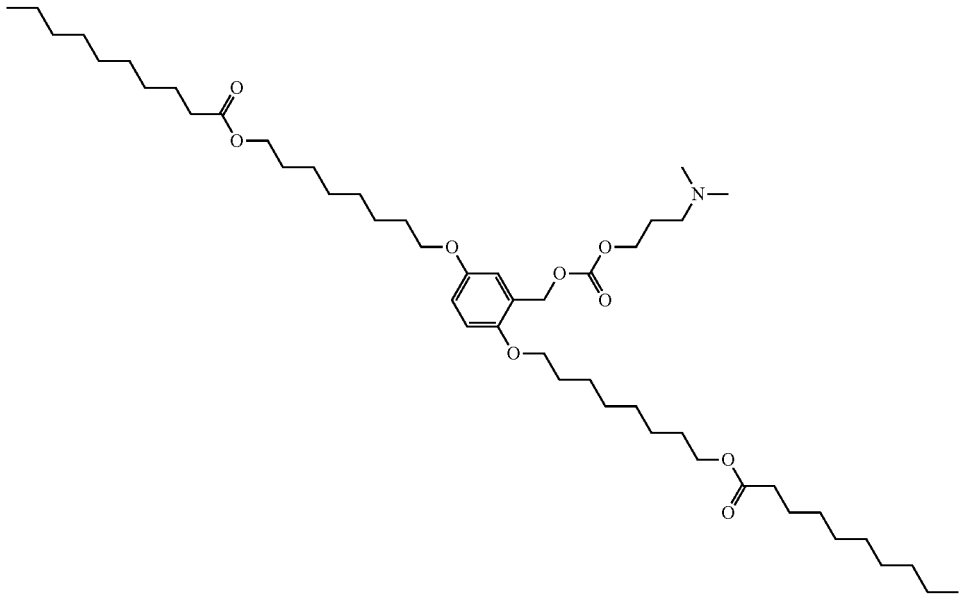 [SMILES: CCCCCCCCCC(=O)OCCCCCCCCOc1ccc(OCCCCCCCCOC(=O)CCCCCCCCC)c(COC(=O)OCCCN(C)C)c1]

To a solution of Intermediate 5c (83 mg, 0.118 mmol) in DCM (0.5 mL) was added 4-nitrophenylchloroformate (35.6 mg, 0.177 mmol) followed by pyridine (38.1 µl, 0.471 mmol) and stirred for 16 h at room temp. The reaction was concentrated under reduced pressure. Solid was dissolved in DCM (0.5 mL) and 3-(dimethylamino)propan-1-ol (36.4 mg, 0.353 mmol) was added followed by DIEA (123 µl, 0.706 mmol) and DMAP (1.438 mg, 0.012 mmol) and stirred for 16 h at room temp. Reaction was diluted with 20 ml dichloromethane and 20 ml water. Organic layer was separated, washed with 2×20 ml water, dried over $MgSO_4$ and concentrated under reduced pressure to give crude product. Crude was purified by silica gel chromatography on ISCO purification system eluting with 10-90% ethyl acetate: heptane but impure product was isolated. Product was re-purified by supercritical fluid chromatography purification eluting with methanol and $CO_2$ to afford desired product as a colorless oil (30 mg, 29% yield). $^1$H NMR (400 MHz, CHLOROFORM-d) δ: 6.93 (d, J=2.3 Hz, 1H), 6.75-6.86 (m, 2H), 5.20 (s, 2H), 4.23 (t, J=6.4 Hz, 2H), 4.06 (t, J=6.7 Hz, 4H), 3.83-3.97 (m, 4H), 2.50 (br. s., 2H), 2.33 (s, 6H), 2.30 (t, J=7.7 Hz, 4H), 1.94 (quin, J=6.7 Hz, 2H), 1.69-1.84 (m, 4H), 1.53-1.69 (m, 8H), 1.40-1.52 (m, 4H), 1.15-1.40 (m, 36H), 0.88 (t, J=6.8 Hz, 6H). $^{13}$C NMR (400 MHz, CHLOROFORM-d) δ: 174.0, 155.1, 152.8, 150.9, 124.6, 116.0, 114.8, 112.5, 68.7, 68.5, 66.1, 65.0, 64.3, 55.9, 45.0, 34.4, 31.8, 29.4, 29.3, 29.3, 29.2, 29.1, 28.6, 26.0, 25.9, 25.0, 22.7, 14.1.

The following example can be prepared using similar coupling methods to those employed for the synthesis of Example 12.

Example 13: ((2-((((3-(diethylamino)propoxy)carbonyl)oxy)methyl)-1,4-phenylene)bis(oxy))bis(octane-8,1-diyl) bis(decanoate)

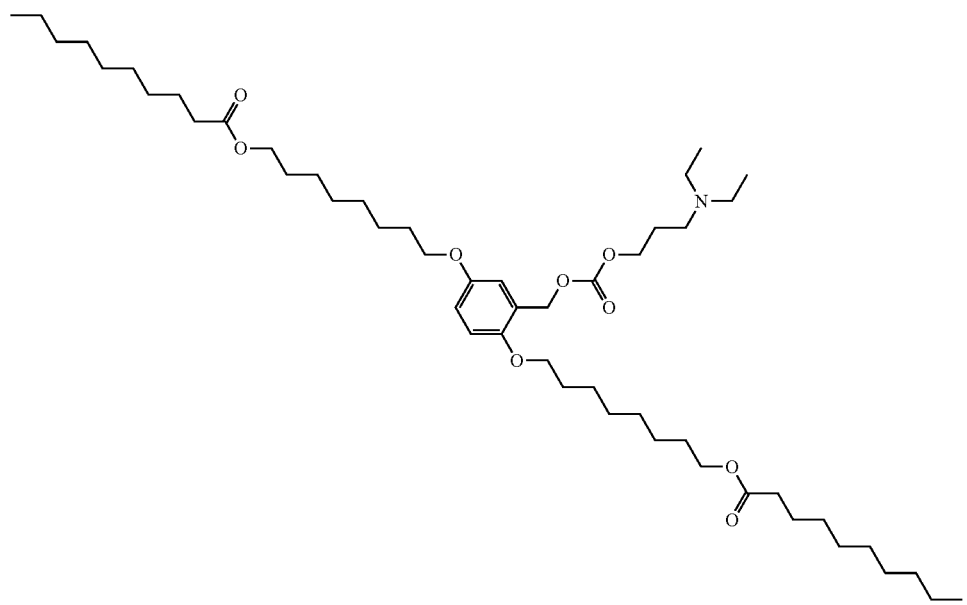 [SMILES: CCCCCCCCCC(=O)OCCCCCCCCOc1ccc(OCCCCCCCCOC(=O)CCCCCCCCC)c(COC(=O)OCCCN(CC)CC)c1]

The desired product was isolated as a colorless oil (35 mg, 27%). ¹H NMR (400 MHz, CHLOROFORM-d) δ: 6.93 (d, J=2.0 Hz, 1H), 6.75-6.84 (m, 2H), 5.20 (s, 2H), 4.22 (t, J=6.4 Hz, 2H), 4.06 (t, J=6.8 Hz, 4H), 3.83-3.96 (m, 4H), 2.61 (br. s., 6H), 2.30 (t, J=7.5 Hz, 4H), 1.83-2.03 (m, 2H), 1.76 (dq, J=13.3, 6.5 Hz, 4H), 1.52-1.68 (m, 8H), 1.40-1.51 (m, 4H), 1.19-1.40 (m, 38H), 1.0-1.12 (m, 4H), 0.88 (t, J=6.8 Hz, 6H). ¹³C NMR (400 MHz, CHLOROFORM-d) δ: 174.0, 155.2, 152.8, 150.9, 124.7, 116.0, 114.8, 112.5, 68.8, 68.5, 65.0, 64.3, 49.1, 46.8, 34.4, 31.8, 29.4, 29.3, 29.3, 29.2, 29.1, 28.6, 26.0, 25.9, 25.0, 22.7, 14.1.

Scheme 5:

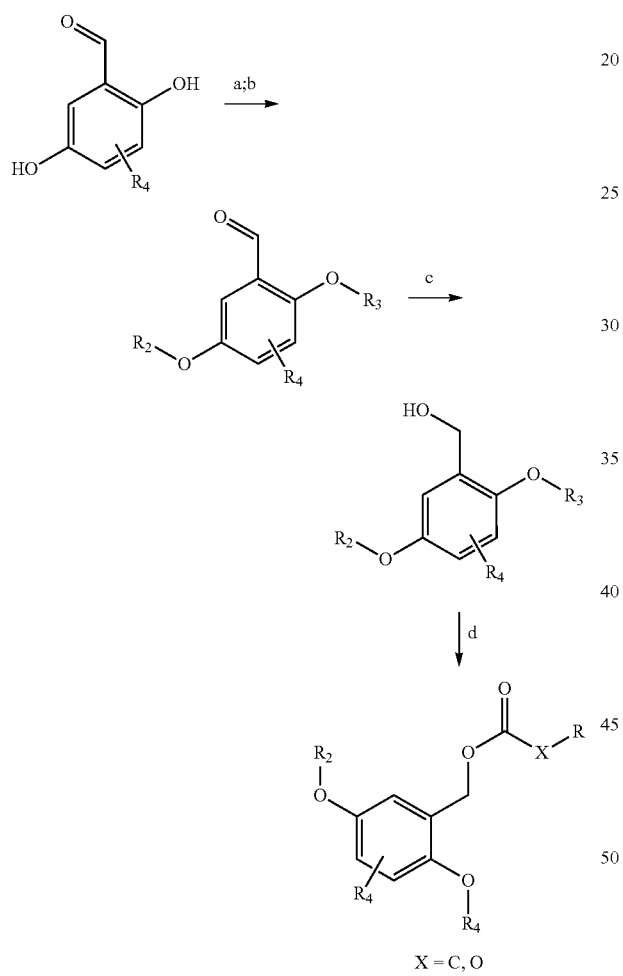

a) Prepartion of acylation partner (if needed) b) Selective bis-acylation for symmetric tail installation. c) Reduction to benzyl alcohol. d) Ester or carbonate cationic head coupling. R is an optionally substituted alkylene-amine, heterocyclyl, heterocyclyl-alkyl Synthesis of Example 14: 3-(dimethylamino)propyl 4-methyl-2,5-bis((9Z,12Z)-octadeca-9,12-dien-1-yloxy)benzyl Carbonate Intermediate 14a:
2,5-dimethoxy-4-methylbenzaldehyde

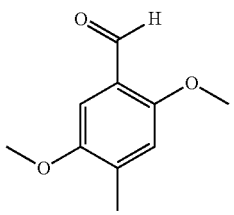

Phosphorous oxychloride (12.5 mL) was slowly added to 2,5-dimethoxy-toluene (5 g, 3.3 mmol) in 10 mL DMF. The reaction was stirred at room temperature for 4 h then heated to 80° C. for 4 h. Then the reaction was poured into ice water and filtered. The filtrate was collected, dried over sodium sulfate and concentrated under reduced pressure to provide 5.1 g (85.9%) of the desired product as a pale yellow solid. TLC: Rf=0.4 (EtOAc: Hexane, 1:9), UV active.

Intermediate 14b:
2,5-dihydroxy-4-methylbenzaldehyde

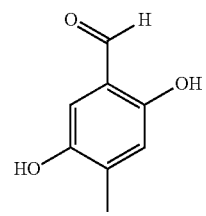

In a round bottom flask Intermediate 14a (1.2 g, 6.6 mmol) was dissolved in 8 mL DCM. The solution was cooled to −78° C. and 1 M borontribromide in DCM (33.3 mL, 33.3 mmol) was added and stirred at the same temperature for 8 h. The reaction mixture was then quenched with 5 mLof water and extracted with ethyl acetate. The combined organic layers were dried over sodium sulfate and evaporated to dryness to provide 1.0 g (99%) desired material as a solid. TLC: Rf=0.3 (EtOAc:Hexane, 1:90), UV active.

Intermediate 14c: 4-methyl-2,5-bis((9Z,12Z)-octadeca-9,12-dien-1-yloxy)benzaldehyde

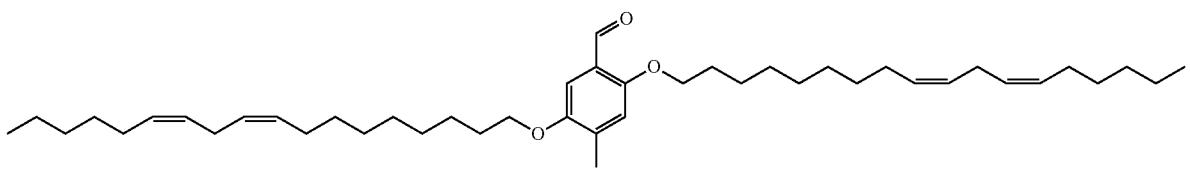

The Intermediate 14c can be prepared using a similar method to that employed for the synthesis of Intermediate 1a from Intermediate 14b. TLC: Rf=0.8 (EtOAc:Hexane, 2:8), UV active.

Intermediate 14d: (4-methyl-2,5-bis((9Z,12Z)-octadeca-9,12-dien-1-yloxy)phenyl)methanol

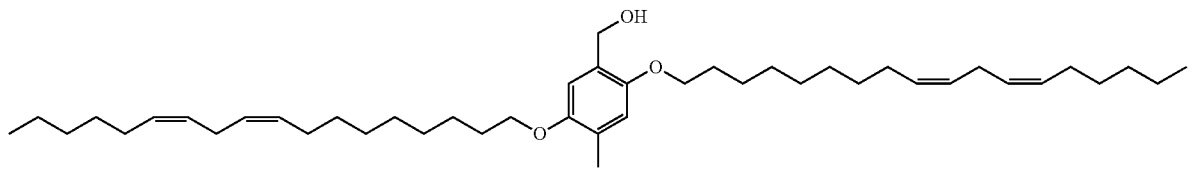 [SMILES: CCCCC/C=C\C/C=C\CCCCCCCCOc1cc(CO)c(OCCCCCCCC/C=C\C/C=C\CCCCC)cc1C]

In a round bottom flask Intermediate 14c (2.8 g, 4.3 mmol) was dissolved in 25 mL methanol. Sodium borohydride (328 mg, 8.6 mmol) was added portion wise at rt and allowed to stir. After 1 hour the reaction was quenched with 10 mL of water and extracted with ethyl acetate (3×). The combined organic layers were dried over sodium sulfate and concentrated under reduced pressure. The crude residue was purified by silica gel using EtOAc/Hexane (30%) as eluent to afford 2.3 g (82.1%) of the desired product. $^1$H NMR (400 MHz, Chloroform-d) δ: 6.76 (s, 1H), 6.69 (s, 1H), 5.30-5.39 (m, 8H), 4.63 (d, J=5.9 Hz, 2H), 3.95 (dd, J=6.4, 6.3 Hz, 2H), 3.90 (dd, J=6.4, 6.3 Hz, 2H), 2.76 (dd, J=6.4, 6.4 Hz, 2H), 2.21 (s, 3H), 2.08-2.03 (m, 8H), 1.80-1.74 (m, 4H), 1.45-1.25 (m, 34H), 0.88 (t, J=6.4, 6.4 Hz, 6H).

The following examples can be prepared using similar coupling methods to those employed for the synthesis of Example 3 from Intermediate 14d.

Example 14: 3-(dimethylamino)propyl 4-methyl-2,5-bis((9Z,12Z)-octadeca-9,12-dien-1-yloxy)benzyl Carbonate

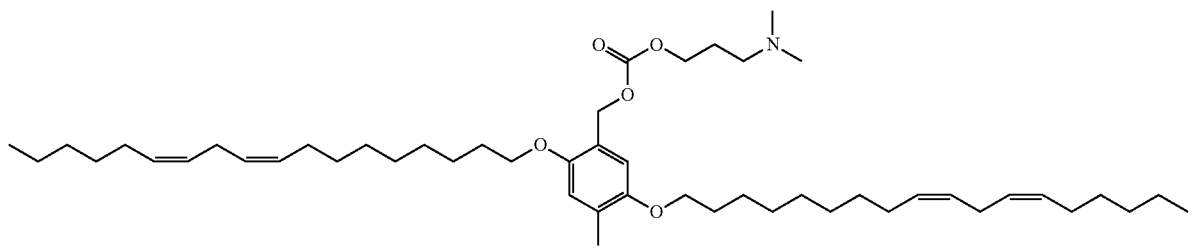 [SMILES: CCCCC/C=C\C/C=C\CCCCCCCCOc1cc(COC(=O)OCCCN(C)C)c(OCCCCCCCC/C=C\C/C=C\CCCCC)cc1C]

$^1$H NMR (400 MHz, Chloroform-d) δ: 6.85 (s, 1H), 6.71 (s, 1H), 5.39 (tq, J=11.0, 5.5, 4.4 Hz, 8H), 5.20 (s, 2H), 4.23 (t, J=6.5 Hz, 2H), 3.93 (td, J=6.4, 4.7 Hz, 4H), 2.80 (t, J=6.5 Hz, 4H), 2.28 (br. s, 6H), 2.23 (s, 3H), 2.15-2.02 (m, 8H), 1.90 (d, J=4.1 Hz, 2H), 1.78 (ddt, J=11.2, 6.1, 2.9 Hz, 4H), 1.53-1.43 (m, 4H), 1.43-1.21 (m, 30H), 0.99-0.87 (m, 6H). MS (m+1)=780.8, Rt=1.38 min (LC Method 2).

Example 15: 4-(dimethylamino)butyl 4-methyl-2,5-bis((9Z,12Z)-octadeca-9,12-dienyloxy)benzyl Carbonate

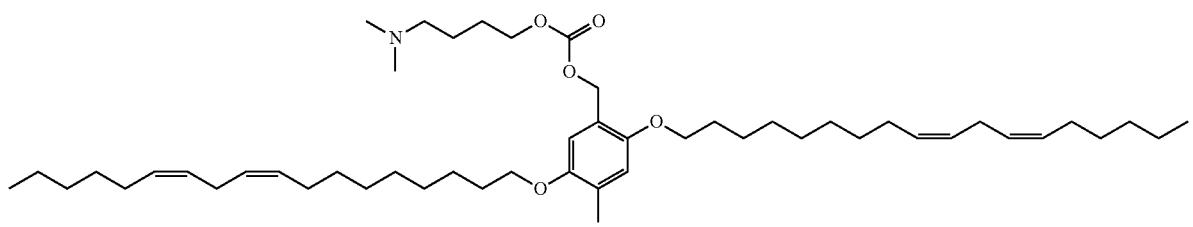 [SMILES: CCCCC/C=C\C/C=C\CCCCCCCCOc1cc(COC(=O)OCCCCN(C)C)c(OCCCCCCCC/C=C\C/C=C\CCCCC)cc1C]

¹H NMR (400 MHz, CHLOROFORM-d) δ: 6.83 (s, 1H), 6.70 (s, 1H), 5.48-5.26 (m, 8H), 5.18 (s, 2H), 4.17 (t, J=6.5 Hz, 2H), 3.91 (dt, J=4.3, 6.4 Hz, 4H), 2.78 (t, J=6.5 Hz, 4H), 2.28 (t, J=6.8 Hz, 2H), 2.21 (s, 9H), 2.06 (q, J=6.7 Hz, 8H), 1.83-1.65 (m, 6H), 1.55 (s, 2H), 1.45 (d, J=5.5 Hz, 4H), 1.41-1.25 (m, 28H), 0.89 (t, J=6.8 Hz, 6H).

Example 16: 4-methyl-2,5-bis((9Z,12Z)-octadeca-9,12-dien-1-yloxy)benzyl 4-(dimethylamino)butanoate

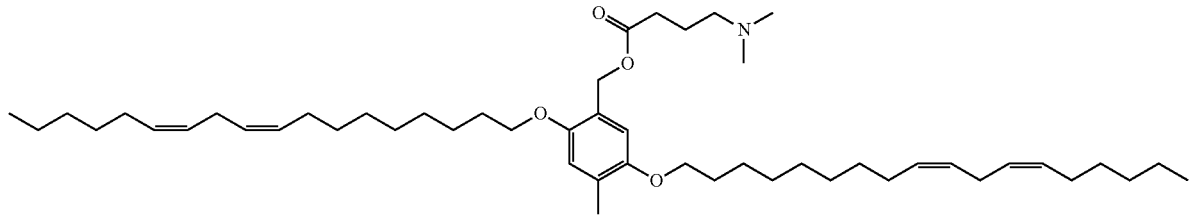 [SMILES: CCCCC/C=C\C/C=C\CCCCCCCCOc1cc(COC(=O)CCCN(C)C)c(OCCCCCCCC/C=C\C/C=C\CCCCC)cc1C]

1H NMR (400 MHz, Chloroform-d) δ: 6.81 (s, 1H), 6.72 (s, 1H), 5.47-5.28 (m, 8H), 5.15 (s, 2H), 3.93 (q, J=6.3 Hz, 4H), 2.80 (t, J=6.5 Hz, 4H), 2.53 (br. s, 6H), 2.44 (t, J=7.2 Hz, 4H), 2.23 (s, 3H), 2.07 (q, J=7.0 Hz, 8H), 1.98 (br. s, 2H), 1.77 (td, J=8.8, 4.4 Hz, 4H), 1.47 (t, J=6.9 Hz, 4H), 1.43-1.20 (m, 28H), 0.91 (t, J=6.7 Hz, 6H). MS (m+1)= 765.0, Rt=1.38 min (LC Method 3)

Synthesis of Example 17: (9Z,9'Z,12Z,12'Z)-2,2'-(2-((4-(dimethylamino)butanoyloxy)methyl)-1,4-phenylene)bis(oxy)bis(ethane-2,1-diyl) dioctadeca-9,12-dienoate Intermediate 17a: (9Z,12Z)-3-hydroxypropyl octadeca-9,12-dienoate

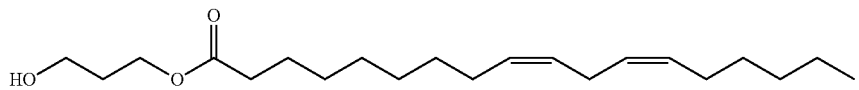 [SMILES: CCCCC/C=C\C/C=C\CCCCCCCC(=O)OCCCO]

In a round bottom flask linoleic acid (3.0 g, 10.7 mmol) was dissolved in glycol (15 mL). HOBT (2.5, 16.1 mmol) and EDC (3.1 g, 16.1 mmol) were added followed by TEA (4.5 mL, 32.1 mmol) and DMAP (653 mg, 5.4 mmol) and the reaction was stirred at room temperature. After 18 hours the reaction was diluted with DCM and water. The organic layer was separated, washed with brine and dried over sodium sulfate and concentrated under reduced pressure to provide desired product 2.46 g (67.8%) as a colorless oil. ¹H NMR (400 MHz, Chloroform-d) δ: 5.41-5.23 (m, 4H), 4.18 (t, J=6.2 Hz, 2H), 3.64 (t, J=6.1 Hz, 2H), 2.72 (t, J=6.2 Hz, 2H), 2.25 (t, J=7.5 Hz, 2H), 2.00 (q, J=6.7 Hz, 4H), 1.88-1.75 (m, 2H), 1.58 (t, J=7.4 Hz, 2H), 1.39-1.15 (m, 14H), 0.84 (td, J=6.9, 3.5 Hz, 3H).

Intermediate 17b: (9Z,9'Z,12Z,12'Z)-2,2'-(5-formyl-1,3-phenylene)bis(oxy)bis(ethane-2,1-diyl) dioctadeca-9,12-dienoate

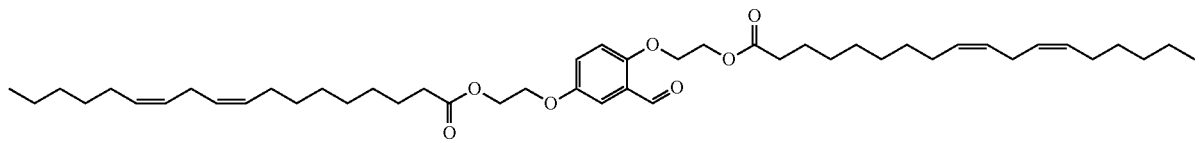 [SMILES: CCCCC/C=C\C/C=C\CCCCCCCC(=O)OCCOc1ccc(OCCOC(=O)CCCCCCC/C=C\C/C=C\CCCCC)c(C=O)c1]

In a round bottom flask Intermediate 17a (1.0 g, 3.08 mmol), 2,5-dihydroxybenzaldehyde (213 mg, 1.54 mmol) and triphenyl phosphine (0.849 g, 3.24 mmol) were dissolved in 12.5 mL THF. DIAD (0.849 mL, 3.24 mmol) was then added. The reaction was stirred at room temperature 3 days and directly concentrated onto celite under reduced pressure prior to purification by silica gel column chromatography on an ISCO purification system, using EtOAc/Heptanes (10 to 20%) as eluent to provide 71.4 mg (3.1%) desired product as a pale yellow oil.

Intermediate 17c: (9Z,9'Z,12Z,12'Z)-2,2'-(2-(hydroxymethyl)-1,4-phenylene)bis(oxy)bis(ethane-2,1-diyl) dioctadeca-9,12-dienoate

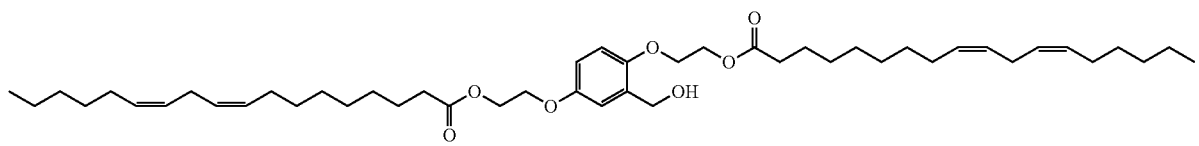

In a round bottom flask Intermediate 17b (71.4 mg, 0.095 mmol) was dissolved in 2 mL ethanol under nitrogen. Sodium borohydride (5.39 mg, 0.143 mmol) was added in one portion and stirred at room temperature. After 30 minutes the reaction was quenched with acetic acid, diluted with water and extracted into DCM (3×). The organic layers were combined, dried over sodium sulfate, and concentrated under reduced pressure to provide 57.1 mg (80%) of desired product as a clear oil.

Example 17: (9Z,9'Z,12Z,12'Z)-2,2'-(2-((4-(dimethylamino)butanoyloxy)methyl)-1,4-phenylene)bis(oxy)bis(ethane-2,1-diyl) dioctadeca-9,12-dienoate

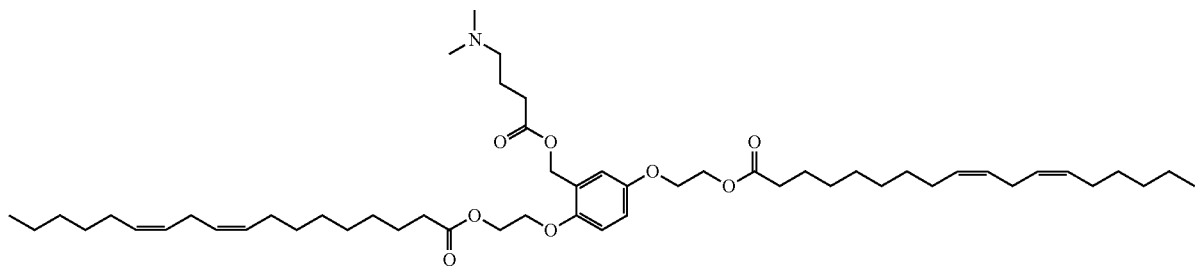 [SMILES: CCCCC/C=C\C/C=C\CCCCCCCC(=O)OCCOc1ccc(OCCOC(=O)CCCCCCC/C=C\C/C=C\CCCCC)c(COC(=O)CCCN(C)C)c1]

In a reaction vial, Intermediate 17c was dissolved in DCM. HATU and dimethylamine were added followed by TEA and DMAP. The reaction was stirred at room temperature. After 18 hours the reaction was diluted with DCM and water. The organic layer was separated, washed with brine and dried over sodium sulfate and concentrated under reduced pressure. The crude residue was purified by prep. HPLC, (TFA modifier). Purity enriched product was then purified by silica gel chromatography on ISCO purification system eluting with MeOH/DCM (0 to 10%). Recovered material was purified again by silica gel chromatography on ISCO purification system eluting with MeOH/DCM (0% to 3% then to 8%) to provide 11.6 mg (17.6%) of desired product isolated as a clear oil. $^1$H NMR (400 MHz, Chloroform-d) δ: 6.94 (s, 1H), 6.83 (d, J=1.5 Hz, 2H), 5.31-5.45 (m, 8H), 5.17 (s, 2H), 4.40 (t, J=4.8 Hz, 4H), 4.09-4.23 (m, 4H), 2.79 (t, J=6.1 Hz, 4H), 2.61 (s, 2H), 2.44-2.51 (m, 2H), 2.30-2.39 (m, 4H), 2.18 (s, 6H), 2.01-2.12 (m, 8H), 1.92 (quin, J=7.2 Hz, 2H), 1.57-1.73 (m, 6H), 1.23-1.45 (m, 26H), 0.91 (t, J=6.8 Hz, 6H). MS (m+1)=866.5, Rt=1.22 min (LC Method 1).

Synthesis of Example 18: (9Z,9'Z,12Z,12'Z)-2,2'-(2-((4-(dimethylamino)butanoyloxy)methyl)-1,4-phenylene)bis(oxy)bis(ethane-2,1-diyl) dioctadeca-9,12-dienoate Intermediate 18a: (9Z,12Z)-4-hydroxybutyl hexadeca-9,12-dienoate

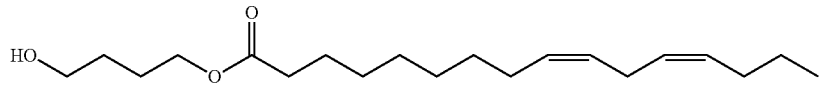 [SMILES: CCC/C=C\C/C=C\CCCCCCCC(=O)OCCCCO]

In a round bottom flask, a mixture of linoleic acid (5.0 g, 17.83 mmol), butanediol (64.3 g, 713 mmol), EDC (3.42 g, 17.83 mmol), DIPEA (3.11 ml, 17.83 mmol) and DMAP (0.163 g, 1.337 mmol) was stirred at 40° C. overnight (high temperature necessary to maintain butane diol as liquid). After 18 hours the reaction was cooled to room temperature and diluted with DCM and water. The organic layer was separated, washed with brine, dried over sodium sulfate and concentrated under reduced pressure. The crude mixture was dry loaded onto celite and purified by silica gel chromatography on ISCO purification system eluting with EtOAc/Heptane (20% to 50%) to provide desired material 3.37 g (58.3%) as a clear oil.

Intermediate 18b: (9Z,9'Z,12Z,12'Z)-((2-formyl-1,4-phenylene)bis(oxy))bis(butane-4,1-diyl) bis(octadeca-9,12-dienoate)

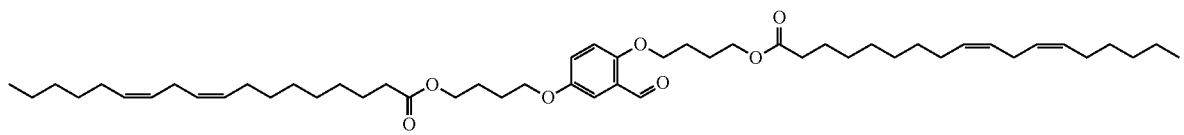 [SMILES: CCCCC/C=C\C/C=C\CCCCCCCC(=O)OCCCCOc1ccc(OCCCCOC(=O)CCCCCCC/C=C\C/C=C\CCCCC)c(C=O)c1]

In a round bottom flask 2,5-dihydroxybenzaldehyde (100 mg, 0.724 mmol), Intermediate 18a (517 mg, 1.593 mmol) and PPh$_3$ (399 mg, 1.520 mmol) were dissolved in 10.5 mL THF. DIAD (0.296 mL, 1.520 mmol) was added and the reaction was allowed to stir at room temperature. After 18 hours the crude reaction mixture was concentrated onto celite under reduced pressure for purification by silica gel chromatography on ISCO purification system eluting with EtOAc/Heptanes (0 to 40%) to provide 86.4 mg (14.8%) of desired product as a yellow oil.

Intermediate 18c: (9Z,9'Z,12Z,12'Z)-((2-(hydroxymethyl)-1,4-phenylene)bis(oxy))bis(butane-4,1-diyl) bis(octadeca-9,12-dienoate)

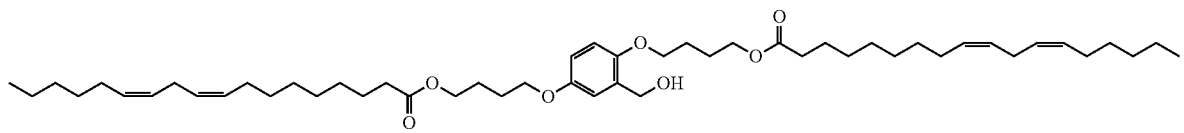 [SMILES: CCCCC/C=C\C/C=C\CCCCCCCC(=O)OCCCCOc1ccc(OCCCCOC(=O)CCCCCCC/C=C\C/C=C\CCCCC)c(CO)c1]

In a reaction vial Intermediate 18b (86.4 mg, 0.107 mmol) was dissolved in 0.5 mL MeOH. Sodium borohydride (4.86 mg, 0.128 mmol) was added and the reaction was stirred at room temperature. After one hour the reaction was quenched by the addition of acetic acid and concentrated under reduced pressure. The crude material was redissolved in DCM then filtered and concentrated under reduced pressure to provide 85 mg (98%) desired product as a colorless oil.

The following example can be prepared using similar coupling methods to those employed for the synthesis of Example 17 with Intermediate 18c.

Example 18: (9Z,9'Z,12Z,12'Z)-2,2'-(2-((4-(dimethylamino)butanoyloxy)methyl)-1,4-phenylene)bis(oxy)bis(ethane-2,1-diyl) dioctadeca-9,12-dienoate

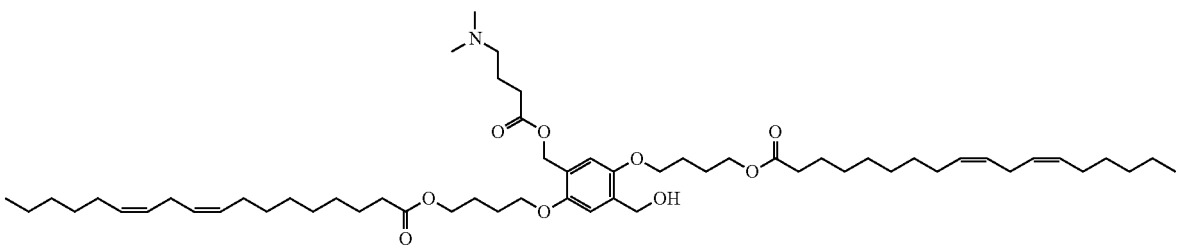 [SMILES: CCCCC/C=C\C/C=C\CCCCCCCC(=O)OCCCCOc1cc(COC(=O)CCCN(C)C)c(OCCCCOC(=O)CCCCCCC/C=C\C/C=C\CCCCC)cc1CO]

1H NMR (400 MHz, Chloroform-d) δ: 6.88 (t, J=1.6 Hz, 1H), 6.77 (d, J=1.7 Hz, 2H), 5.46-5.25 (m, 8H), 5.14 (s, 2H), 4.13 (h, J=2.4 Hz, 4H), 3.94 (dt, J=9.2, 5.3 Hz, 4H), 2.77 (t, J=6.5 Hz, 4H), 2.44 (t, J=7.3 Hz, 2H), 2.35 (s, 6H), 2.32-2.25 (m, 4H), 2.04 (q, J=6.9 Hz, 8H), 1.91 (s, 2H), 1.81 (dq, J=8.3, 5.0, 4.1 Hz, 8H), 1.67-1.56 (m, 4H), 1.40-1.23 (m, 30H), 0.89 (t, J=6.7 Hz, 6H). MS (m+1)=922.9, Rt=1.29 min (LC Method 3).

Synthesis of Example 19: 2,4-bis((9Z,12Z)-octadeca-9,12-d ienyloxy)benzyl 4-(dimethylamino)butanoate Intermediate 19a: 2,4-bis((9Z,12Z)-octadeca-9,12-dien-1-yloxy)benzaldehyde

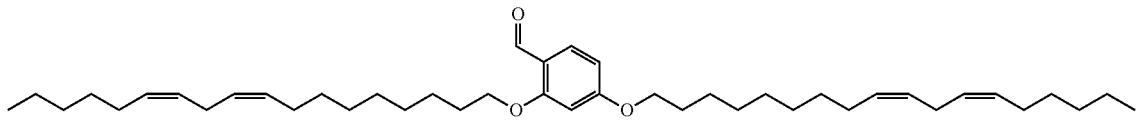 [SMILES: CCCCC/C=C\C/C=C\CCCCCCCCOc1ccc(C=O)c(OCCCCCCCC/C=C\C/C=C\CCCCC)c1]

Can be prepared using similar methods to Intermediate 1a using 2,4-dihydroxybenzaldehyde as starting material. TLC: Rf=0.8 (EtOAc: Hexane, 2:8), UV active.

Intermediate 19b: (2,4-bis((9Z,12Z)-octadeca-9,12-dien-1-yloxy)phenyl)methanol

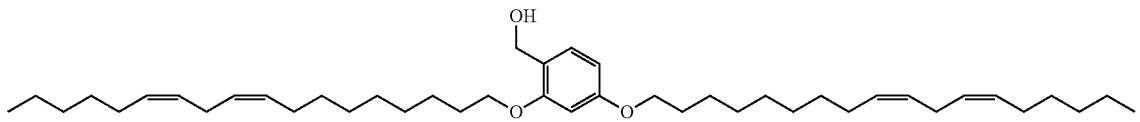

Can be prepared using similar methods to Intermediate 1 b using Intermediate 19a as starting material. TLC: Rf=0.5 (EtOAc: Hexane, 2:8), UV active.

Example 19: 2,4-bis((9Z,12Z)-octadeca-9,12-dienyloxy)benzyl 4-(dimethylamino)butanoate

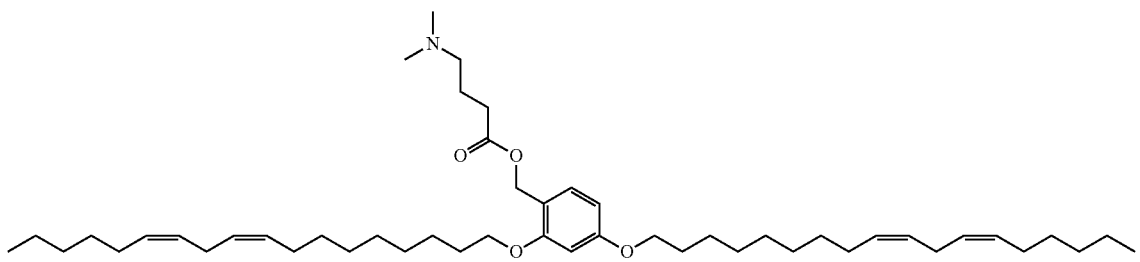 [SMILES: CCCCC/C=C\C/C=C\CCCCCCCCOc1ccc(COC(=O)CCCN(C)C)c(OCCCCCCCC/C=C\C/C=C\CCCCC)c1]

In a round bottom flask Intermediate 19b (2.2 g, 3.5 mmol) was dissolved in 30 mL DCM. EDCI.HCl (1.98 g, 10.38 mmol) was added dropwise followed by 4-(dimethylamino)butanoic acid (1.74 g, 10.4 mmol), DIPEA (2.7 g, 20.75 mmol) and DMAP (84 mg, 0.70 mmol) in that order. The reaction was stirred 14 h at room temperature. Then reaction was extracted into EtOAc. The organic layer was concentrated under a reduced pressure and the crude residue was purified by silica gel column chromatography eluting with MeOH/DCM (5%) as gradient to provide desired product 0.90 g (34.3%) as a yellow oil. $^1$H NMR (400 MHz, CHLOROFORM-d) δ: 7.20 (d, J=8.6 Hz, 1H), 6.40-6.50 (m, 2H), 5.29-5.47 (m, 8H), 5.12 (s, 2H), 3.96 (td, J=6.4, 2.8 Hz, 4H), 2.80 (t, J=6.3 Hz, 4H), 2.32-2.45 (m, 4H), 2.20-2.31 (m, 6H), 2.07 (q, J=6.6 Hz, 8H), 1.68-1.92 (m, 6H), 1.43-1.57 (m, 4H), 1.19-1.43 (m, 28H), 0.91 (t, J=7.1 Hz, 6H). MS (m+1)=750.5, Rt=1.19 min (LC Method 1).

Synthesis of Example 20: ((2-(((4-(Dimethylamino) butanoyl)oxy)methyl)-1,4-phenylene)bis(oxy))bis (propane-3,1-diyl) bis(4,4-bis(octyloxy)butanoate)

Intermediate 20a: 3-((Tert-butyldimethylsilyl)oxy)propyl Methanesulfonate

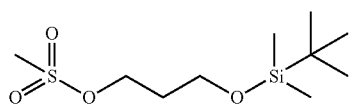 [SMILES: CC(C)(C)[Si](C)(C)OCCCOS(C)(=O)=O]

To the solution of 3-((tert-butyldimethylsilyl)oxy)propan-1-ol (2 g, 10.51 mmol) and triethylamine (2.2 ml, 15.77 mmol) in 30 ml of DCM at 0° C. was added methanesulfonyl chloride (1 ml, 12.62 mmol) slowly dropwise. Reaction mixture was allowed to stir at 30° C. for 30 min. Progress of the reaction was monitored by TLC. Reaction mixture was quenched with 50 ml of water and extracted with DCM (2×50 ml). The combined organic layers were dried over sodium sulfate and evaporated to dryness to afford 2.7 g (96% yield) of a pale brown color liquid. TLC: EtOAc: Hexanes (2:8): Rf=0.5.

Intermediate 20b: 2,5-Bis(3-((tert-butyldimethylsilyl)oxy)propoxy)benzaldehyde

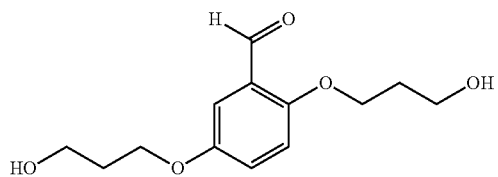

To the suspension of $K_2CO_3$ (1.67 g, 12.08 mmol) in 20 ml of DMF was added 2,5-dihydroxybenzaldehyde (556 mg, 4.02 mmol) and Intermediate 20a (2.7 g, 10.07 mmol), followed by tetrabutyl ammonium iodide (200 mg, cat.). Reaction mixture was heated to 100° C. for 3 h. Progress of the reaction was monitored by TLC. Reaction mixture was quenched with 50 ml of water and extracted with (3×50 ml) of EtOAc. The combined organic layers were washed with brine, dried over sodium sulfate and evaporated to dryness to afford pale brown color liquid. The product was purified by flash-chromatography (Silica gel (230-400 mesh)). Product was eluted at 5% EtOAc in Hexanes to give 1.6 g (82% yield) of a pale brown color liquid. TLC: EtOAc: Hexanes (2:8): Rf=0.9.

Intermediate 20c: 2,5-Bis(3-hydroxypropoxy)benzaldehyde

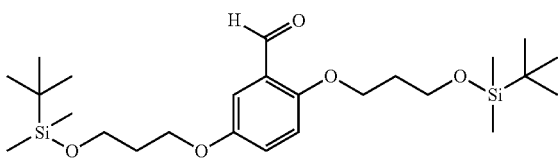 [SMILES: CC(C)(C)[Si](C)(C)OCCCOc1ccc(OCCCO[Si](C)(C)C(C)(C)C)c(C=O)c1]

To the solution of Intermediate 20b (500 mg, 1.03 mmol) in 5 ml of dry THF at 0° C. was added 1M TBAF in THF (4.1 ml, 4.14 mmol) and stirred for 1 h at the same temperature, then allowed to stir at 30° C. for 1 h. Progress of the reaction was monitored by TLC. Reaction mixture was quenched with 20 ml of water and extracted with EtOAc (3×50 ml). The combined organic layers were washed with brine, dried over sodium sulfate and evaporated to dryness to afford 250 mg of a pale yellow colored liquid. TLC: EtOAc: Hexanes (2:8): Rf=0.3.

Intermediate 20d: ((2-Formyl-1,4-phenylene)bis (oxy))bis(propane-3,1-diyl) bis(4,4-bis(octyloxy) butanoate)

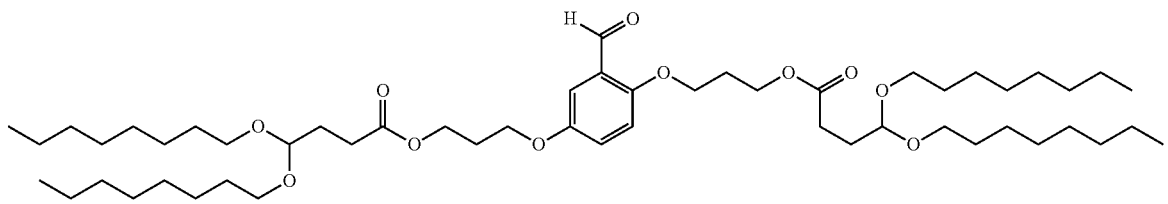 [SMILES: CCCCCCCCOC(CCC(=O)OCCCOc1ccc(OCCCOC(=O)CCC(OCCCCCCCC)OCCCCCCCC)c(C=O)c1)OCCCCCCCC]

To the solution of Intermediate 20c (250 mg, 0.98 mmol) and 4,4-bis(octyloxy)butanoic acid (746 mg, 2.16 mmol) in 10 ml of DMF was added DIPEA (0.7 ml, 3.92 mmol), DMAP (60 mg, 0.49 mmol) followed by HATU (930 mg, 2.45 mmol) and stirred at 30° C. for 24 h. Progress of the reaction was monitored by TLC. Reaction mixture was quenched with 50 ml of water and extracted with EtOAc (3×50 ml). The combined organic layers were washed with brine, dried over sodium sulfate and evaporated to dryness to afford pale yellow color liquid. The product was purified by flash-chromatography (Silica gel 230-400 mesh). Product was eluted at 20 EtOAc in Hexanes to give 500 mg (56% yield) of a pale yellow liquid. TLC: EtOAc: Hexanes (2:8): Rf=0.4.

Intermediate 20e: ((2-(Hydroxymethyl)-1,4-phenylene)bis(oxy))bis(propane-3,1-diyl) bis(4,4-bis(octyloxy)butanoate)

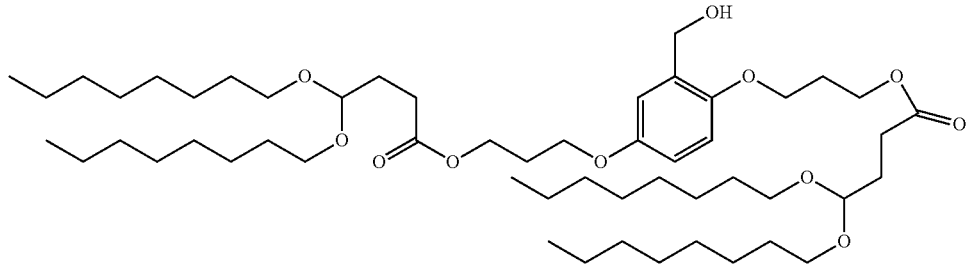 [SMILES: CCCCCCCCOC(CCC(=O)OCCCOc1ccc(OCCCOC(=O)CCC(OCCCCCCCC)OCCCCCCCC)c(CO)c1)OCCCCCCCC]

To the solution of Intermediate 20d (500 mg, 0.551 mmol) in 5.5 ml of methanol and 2 ml of THF was added sodium borohydride (13 mg, 0.341 mmol) at 0° C. and stirred for 5 min. Progress of the reaction was monitored by TLC. Reaction mixture was quenched with 10 ml of water and extracted with EtOAc (3×30 ml). The combined organic layers were washed with 30 ml of brine solution, dried over sodium sulfate and evaporated to dryness to afford desired the product, 450 mg (89% yield) as a colorless liquid. TLC: EtOAc: Hexanes (2:8): Rf=0.3.

Example 20: ((2-(((4-(Dimethylamino)butanoyl)oxy)methyl)-1,4-phenylene)bis(oxy))bis(propane-3,1-diyl) bis(4,4-bis(octyloxy)butanoate)

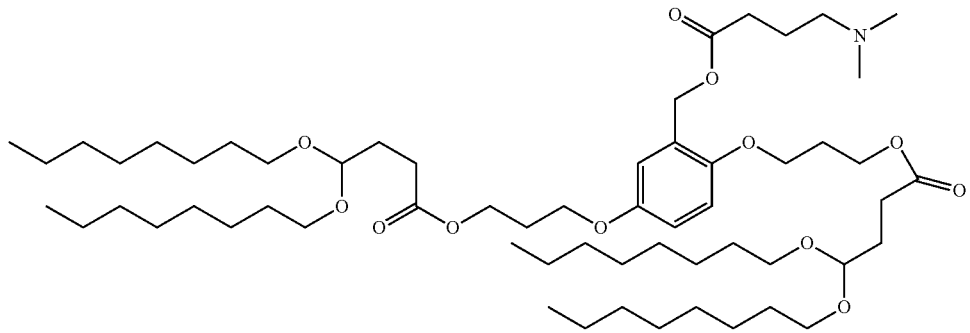 [SMILES: CCCCCCCCOC(CCC(=O)OCCCOc1ccc(OCCCOC(=O)CCC(OCCCCCCCC)OCCCCCCCC)c(COC(=O)CCCN(C)C)c1)OCCCCCCCC]

To the solution of Intermediate 20e (190 mg, 0.20 mmol), 4-dimethyl amino butanoic acid hydrochloride (70 mg, 0.41 mmol) and DIPEA (0.12 ml, 0.83 mmol), in DCM (7 ml) was added EDC.HCl (80 mg, 0.41 mmol) followed by DMAP (51 mg, 0.41 mmol). Reaction was stirred at 30° C. for 20 h. Progress of the reaction was monitored by TLC. Reaction mixture was quenched with 20 ml of water and extracted with DCM (3×50 ml). The combined organic layers were dried over sodium sulfate and evaporated to dryness to afford crude solid. The product was purified by flash-chromatography (Silica gel (230-400 mesh)). Product was eluted at 4% methanol in DCM to give 140 mg (65% yield) as a yellow colored, viscous liquid. $^1$H NMR (400 MHz, CDCl$_3$): δ=6.89 (s, 1H), 6.77 (s, 2H), 5.13 (s, 2H), 4.48 (t, J=5.6 Hz, 2H), 4.28 (t, J=6.4 Hz, 4H), 4.00 (q, J=6.0 Hz, 4H), 3.57 (q, J=6.8 Hz, 4H), 3.40 (q, J=6.4 Hz, 4H), 2.43-1.81 (m, 26H), 1.56-1.49 (m, 12H), 1.49-1.26 (m, 34H), 0.87 (t, J=6.4 Hz, 12H) ppm. MS (m+1)=1022.5, Rt=1.17 min (LC Method 4).

Synthesis of Example 21: ((2-(((4-(Dimethylamino)butanoyl)oxy)methyl)-1,4-phenylene)bis(oxy))bis(pentane-5,1-diyl) bis(4,4-bis(octyloxy)butanoate)

Intermediate 21a: 2,5-Bis((5-((tert-butyldimethylsilyl)oxy)pentyl)oxy)benzaldehyde

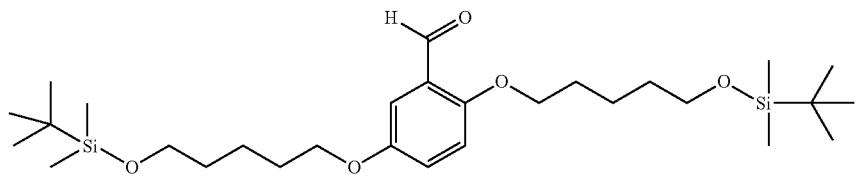 [SMILES: CC(C)(C)[Si](C)(C)OCCCCCOc1ccc(OCCCCCO[Si](C)(C)C(C)(C)C)c(C=O)c1]

Can be prepared using similar method to that employed for the synthesis of Intermediate 20b from 2,5-dihydroxybenzaldehyde and 5-((tert-butyldimethylsilyl)oxy)pentyl methanesulfonate. TLC: EtOAc: Hexanes (2:8): Rf=0.9.

Intermediate 21b: 2,5-Bis((5-hydroxypentyl)oxy)benzaldehyde

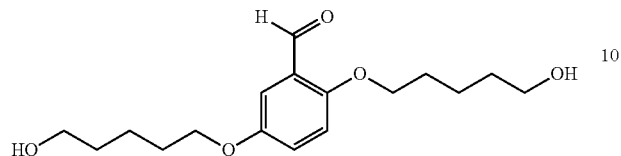

Can be prepared using similar method that employed for the synthesis of Intermediate 20c from 2,5-bis((5-((tert-butyldimethylsilyl)oxy)pentyl)oxy)benzaldehyde (Intermediate 21a). TLC: EtOAc: Hexanes (8:2): Rf=0.1.

Intermediate 21c: ((2-Formyl-1,4-phenylene)bis(oxy))bis(pentane-5,1-diyl) bis(4,4-bis(octyloxy)butanoate)

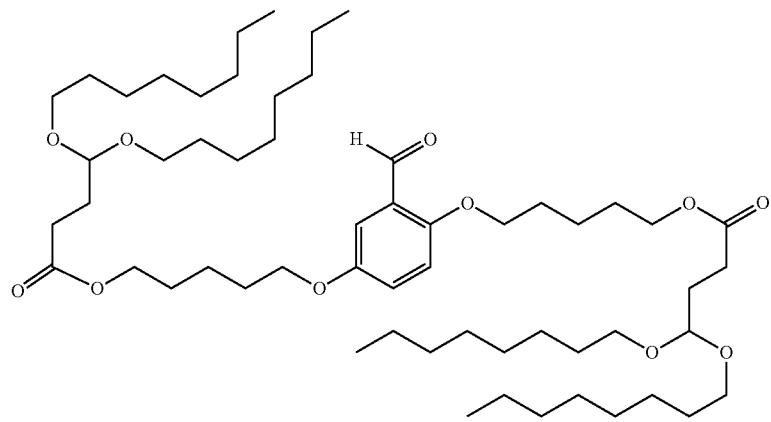 [SMILES: CCCCCCCCOC(CCC(=O)OCCCCCOc1ccc(OCCCCCOC(=O)CCC(OCCCCCCCC)OCCCCCCCC)c(C=O)c1)OCCCCCCCC]

Can be prepared using similar method to that employed for the synthesis of Intermediate 20d from 2,5-bis((5-hydroxypentyl)oxy)benzaldehyde (Intermediate 21b) and 4-dimethyl amino butanoic acid. TLC: EtOAc: Hexanes (2:8): Rf=0.4.

Intermediate 21d: ((2-(Hydroxymethyl)-1,4-phenylene)bis(oxy))bis(pentane-5,1-diyl) bis(4,4-bis(octyloxy)butanoate)

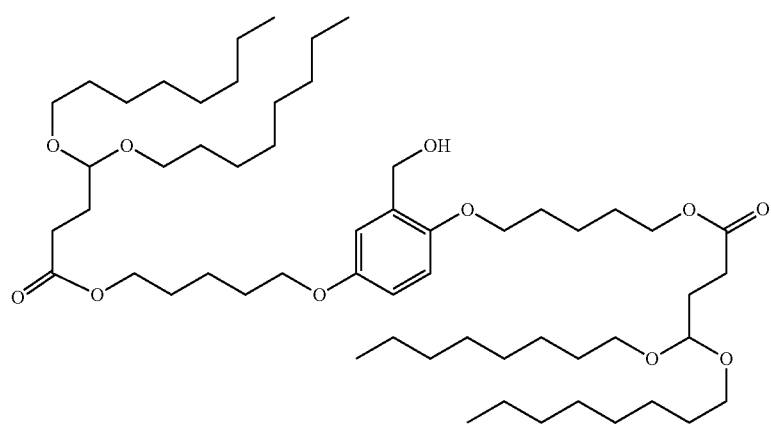 [SMILES: CCCCCCCCOC(CCC(=O)OCCCCCOc1ccc(OCCCCCOC(=O)CCC(OCCCCCCCC)OCCCCCCCC)c(CO)c1)OCCCCCCCC]

Can be prepared using similar method to that employed for the synthesis of Intermediate 20e from Intermediate 21c. TLC: EtOAc: Hexanes (2:8): Rf=0.3.

Example 21: ((2-(((4-(Dimethylamino)butanoyl)oxy)methyl)-1,4-phenylene)bis(oxy))bis(pentane-5,1-diyl) bis(4,4-bis(octyloxy)butanoate)

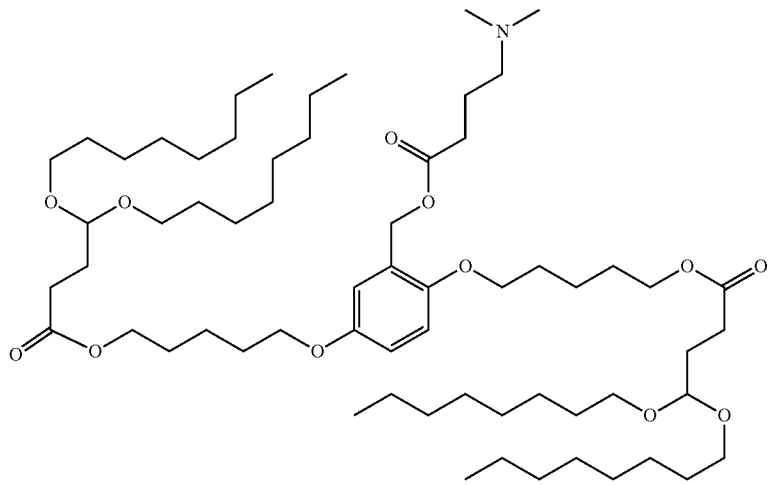 [SMILES: CCCCCCCCOC(CCC(=O)OCCCCCOc1ccc(OCCCCCOC(=O)CCC(OCCCCCCCC)OCCCCCCCC)c(COC(=O)CCCN(C)C)c1)OCCCCCCCC]

To the solution of Intermediate 21d, 4-dimethyl amino butanoic acid hydrochloride (104 mg, 0.62 mmol) and DIPEA (0.2 ml, 1.24 mmol) in DCM (10 ml) was added EDC.HCl (119 mg, 0.62 mmol) and followed by DMAP (76 mg, 0.62 mmol). Reaction was stirred at 30° C. for 16 h. Progress of the reaction was monitored by TLC. Reaction mixture was quenched with 20 ml of water and extracted with DCM (3×50 ml). The combined organic layers were dried over sodium sulfate and evaporated to dryness to afford a crude solid. The product was purified by flash-chromatography (Silica gel (230-400 mesh)). Product was eluted at 4% methanol in DCM to give 180 mg (54% yield) of a pale yellow colored, viscous liquid. $^1$H NMR (400 MHz, CDCl$_3$): δ=6.89 (s, 1H), 6.77 (s, 2H), 5.13 (s, 2H), 4.49 (t, J=5.6 Hz, 2H), 4.09 (t, J=6 Hz, 4H), 3.90 (q, J=4 Hz, 4H), 3.57 (q, J=6.8 Hz, 4H), 3.41 (q, J=6.4 Hz, 4H), 2.40-2.22 (m, 8H), 2.00 (s, 6H), 1.95-1.66 (m, 30H), 1.50-1.27 (m, 37H), 0.87 (t, J=6.4 Hz, 11H) ppm. MS (m+1)= 1078.6, Rt=1.20 min (LC Method 4).

Synthesis of Example 22: ((2-(((4-(diethylamino)butanoyl)oxy)methyl)-1,4-phenylene)bis(oxy))bis(pentane-5,1-diyl) bis(4,4-bis(octyloxy)butanoate)

Intermediate 22a: methyl 4-(diethylamino)butanoate

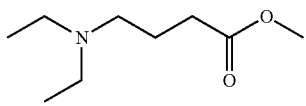

In a 500 ml sealed tube, methyl 4-bromo butanoate (30.0 g, 165.7 mmol) was taken into dry THF (200 ml). Diethylamine (86 ml, 828.7 mmol) was added. The resulting mixture was stirred for 16 h at 70° C. and monitored by TLC. The reaction mixture was then diluted with water (200 ml), extracted with EtOAc (2×500 ml). The combined organic layers were washed with brine (500 ml), dried over Na$_2$SO$_4$, and concentrated under reduced pressure to provide 25 g (87% yield) of the desired product as a pale brown liquid. TLC: EtOAc:Hexane (3:7), Rf=0.2, Iodine & PMA stain active.

Intermediate 22b: 2: 4-(diethylamino)butanoic Acid

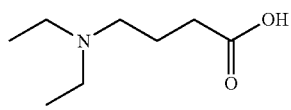

In a round bottom flask, a mixture of Intermediate 22a (25.0 g, 144.4 mmol) and 6 N HCl (200 ml) was heated and refluxed for 7 h. The reaction was monitored by TLC. The reaction mixture was then evaporated and dried to afford 26 g (92% yield) of the desired product as a white solid. TLC: methanol:dichloromethane (1:9), Rf=0.13, Iodine & PMA stain active.

Example 22: ((2-(((4-(diethylamino)butanoyl)oxy)methyl)-1,4-phenylene)bis(oxy))bis(pentane-5,1-diyl) bis(4,4-bis(octyloxy)butanoate)

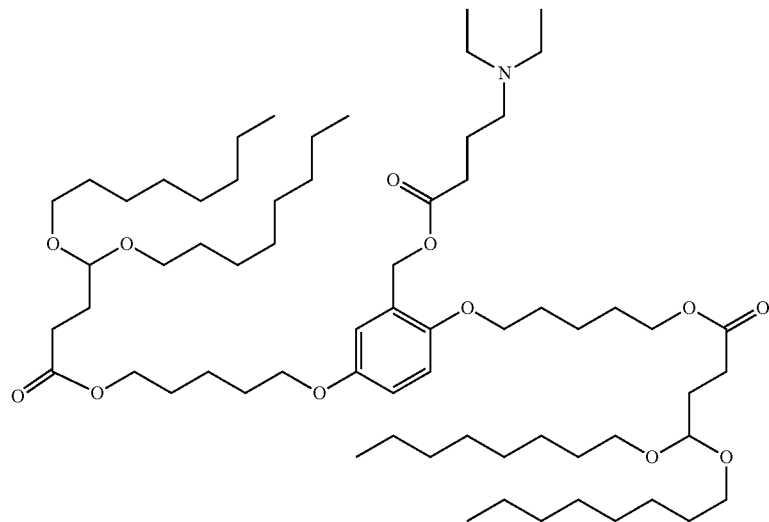 [SMILES: CCCCCCCCOC(CCC(=O)OCCCCCOc1ccc(OCCCCCOC(=O)CCC(OCCCCCCCC)OCCCCCCCC)c(COC(=O)CCCN(CC)CC)c1)OCCCCCCCC]

In a round bottom flask, Intermediate 21d (190 mg, 0.196 mmol), Intermediate 22b (0.581 g, 4.75 mmol) and DIPEA (0.15 ml, 0.784 mmol) were taken into dichloromethane (10 ml). EDC (75 mg, 0.393 mmol) was added in one portion, followed by addition of DMAP (48 mg, 0.393 mmol). The reaction was stirred at ambient temperature for 16 h and monitored by TLC. The reaction mixture was quenched with 20 ml of water and extracted with DCM (3×50 ml). The combined organic layers were dried over sodium sulfate and evaporated to dryness to afford solid crude. The product was purified by flash chromatography (silica gel, 230-400 mesh) using methanol/dichloromethane (4%) as eluent to provide 140 mg (64% yield) of the desired product as a pale yellow colored, viscous liquid. $^1$H NMR (400 MHz, CDCl$_3$): δ=0.82 (t, J=7.10 Hz, 12H) 0.85-1.00 (m, 6H) 1.09-1.32 (m, 40H) 1.37-1.55 (m, 12H) 1.58-1.67 (m, 4H) 1.67-1.78 (m, 6H) 1.79-1.93 (m, 4H) 2.24-2.52 (m, 12H) 3.33 (dt, J=9.26, 6.68 Hz, 4 H) 3.50 (dt, J=9.05, 6.72 Hz, 4H) 3.78-3.91 (m, 4H) 3.95-4.07 (m, 4H) 4.42 (t, J=5.62 Hz, 2H) 5.07 (s, 2H) 6.70 (d, J=1.71 Hz, 2H) 6.82 (s, 1H). MS (m+1)=1107.9, Rt=2.98 min (LC Method 5).

Example 23: ((2-(((1,4-Dimethylpiperidine-4-carbonyl)oxy)methyl)-1,4-phenylene)bis(oxy))bis(pentane-5,1-diyl) bis(4,4-bis(octyloxy)butanoate)

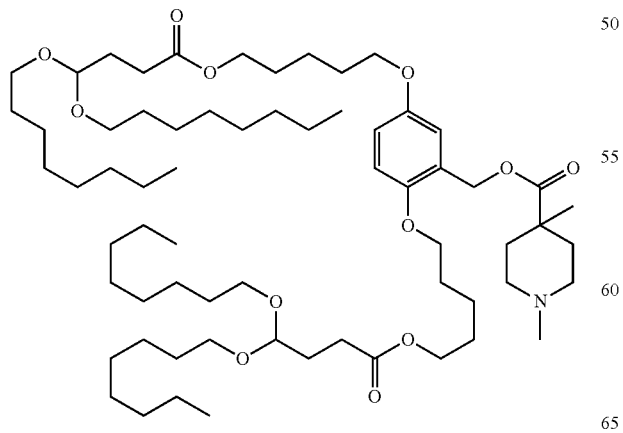

To the solution of 1,4-dimethylpiperidine-4-carboxylic acid (120 mg, 0.76 mmol) and NEt$_3$ (0.3 mL, 2.03 mmol) in DCM (10 mL) was added 2,4,6-trichlorobenzoyl chloride (185 mg, 0.76 mmol) slowly dropwise at 30° C. and stirred for 4 h. After which time, Intermediate 21d (490 mg, 0.51 mmol) in DCM (5 mL) and DMAP (124 mg, 1.01 mmol) were added and the reaction was stirred for 20 h. Progress of the reaction was monitored by TLC. Reaction mixture was quenched with H$_2$O (20 mL) and extracted with DCM (3×50 mL). The combined organic layers were dried over sodium sulfate and evaporated to dryness to afford solid crude. The product was purified by flash-chromatography (silica gel (230-400 mesh)). Product was eluted at 4% Methanol in DCM to give 430 mg (77% yield) of the title compound as a pale yellow colored, viscous liquid. $^1$H NMR (400 MHz, CD$_2$Cl$_2$): δ=6.86 (d, J=2.3 Hz, 1H), 6.75-6.83 (m, 2H), 5.12 (s, 2H), 4.45 (t, J=5.6 Hz, 2H), 4.07 (t, J=6.7 Hz, 4H), 3.87-3.96 (m, 4H), 3.54 (dt, J=9.3, 6.7 Hz, 4H), 3.38 (dt, J=9.3, 6.7 Hz, 4H), 2.59 (br s, 2H), 2.35 (t, J=7.6 Hz, 4H), 2.03-2.29 (m, 7H), 1.83-1.92 (m, 4H), 1.73-1.83 (m, 4H), 1.64-1.74 (m, 4H), 1.44-1.60 (m, 13H), 1.18-1.38 (m, 41H), 1.21 (s, 3H), 0.84-0.93 (m, 12H). MS (m+1)= 1105.2, Rt=1.34 min (LC Method 6).

Synthesis of Example 24: 8-(4-((5-((4,4-Bis(octyloxy)butanoyl)oxy)pentyl)oxy)-2-(((4(dimethylamino) butanoyl)oxy)methyl)phenoxy)octyl Decanoate Intermediate 24a:
8-(2-Formyl-4-hydroxyphenoxy)octyl Decanoate

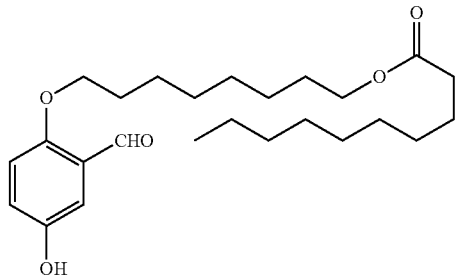 [SMILES: CCCCCCCCCC(=O)OCCCCCCCCOc1ccc(O)cc1C=O]

Can be prepared using similar method to that employed for the synthesis of Intermediate 20b from 2,5-dihydroxybenzaldehyde and 8-((methylsulfonyl)oxy)octyl decanoate. TLC: EtOAc: Hexanes (2:8): Rf=0.9.

Intermediate 24b: 8-(4-((5-((Tert-butyldimethylsilyl)oxy)pentyl)oxy)-2-formylphenoxy)octyl Decanoate

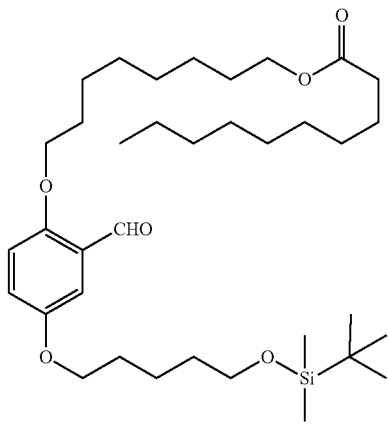 [SMILES: CCCCCCCCCC(=O)OCCCCCCCCOc1ccc(OCCCCCO[Si](C)(C)C(C)(C)C)cc1C=O]

Can be prepared using similar method to that employed for the synthesis of Intermediate 20b from Intermediate 24a and 5-((tert-butyldimethylsilyl)oxy)pentyl methanesulfonate. TLC: EtOAc: Hexanes (2:8): Rf=0.6.

Intermediate 24c: 8-(2-Formyl-4-((5-hydroxypentyl)oxy)phenoxy)octyl Decanoate

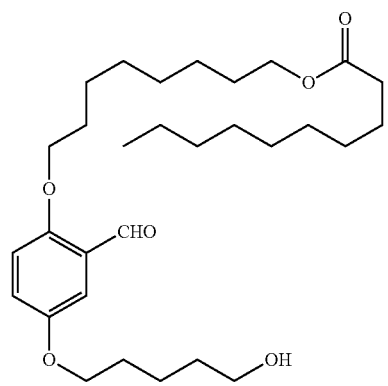 [SMILES: CCCCCCCCCC(=O)OCCCCCCCCOc1ccc(OCCCCCO)cc1C=O]

Can be prepared using similar method to that employed for the synthesis of Intermediate 20c from Intermediate 24b. TLC: EtOAc: Hexanes (8:2): Rf=0.2.

Intermediate 24d: 8-(4-((5-((4,4-Bis(octyloxy)butanoyl)oxy)pentyl)oxy)-2-formylphenoxy)octyl Decanoate

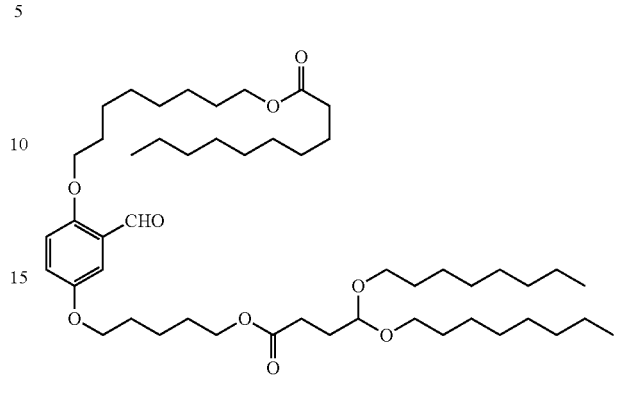

Can be prepared using similar method to that employed for the synthesis of Intermediate 20d from intermediate 24c. TLC: methanol:DCM (1:9): Rf=0.5.

Intermediate 24e: 8-(4-((5-((4,4-Bis(octyloxy)butanoyl)oxy)pentyl)oxy)-2-(hydroxymethyl)phenoxy)octyl Decanoate

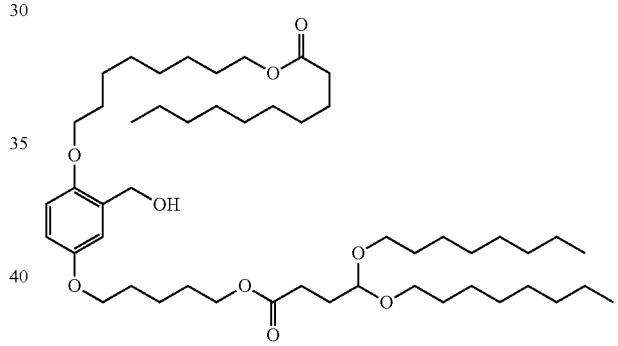

Can be prepared using similar method to that employed for the synthesis of Intermediate 20e from Intermediate 24d. TLC: EtOAc: Hexanes (2:8): Rf=0.4.

Example 24: 8-(4-((5-((4,4-Bis(octyloxy)butanoyl)oxy)pentyl)oxy)-2-(((4(dimethylamino)butanoyl)oxy)methyl)phenoxy)octyl Decanoate

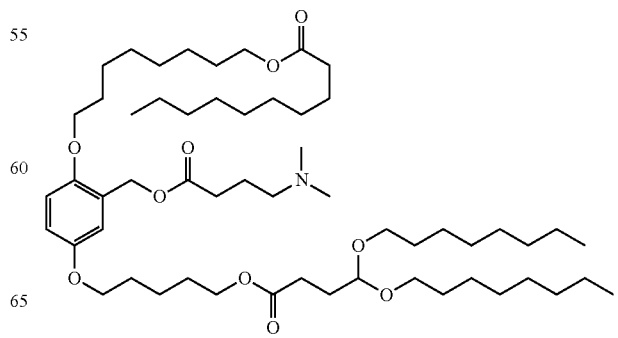

To a solution of Intermediate 24e (1.2 g, 1.43 mmol) in DCM (30 ml) was added EDC.HCl (550 mg, 2.87 mmol), DIPEA (0.75 ml, 4.31 mmol), DMAP (175 mg, 1.43 mmol), and N,N-dimethylaminobutyricacid.HCl (361 mg, 2.15 mmol). The mixture was stirred for 18 h at 25° C. under nitrogen atmosphere. Progress of the reaction was monitored by TLC. Reaction mixture was diluted with water (200 ml), extracted with DCM (2×150 ml), combined organic layers were washed with brine (100 ml), dried over $Na_2SO_4$ and concentrated under reduced pressure, to obtain a pale green liquid. The product was purified by flash-chromatography (Silica gel 230-400 mesh). Product was eluted at 5% Methanol in DCM to give 550 mg (42% yield) of a pale green liquid. $^1$H NMR (400 MHz, CDCl$_3$): δ=6.88 (s, 1H), 6.77 (s, 2H), 5.14 (s, 2H), 4.49 (t, J=4 Hz, 1H), 4.11-4.04 (m, 4H), 3.92-3.89 (m, 4H), 3.57 (q, J=6.8 Hz, 2H), 3.41 (q, J=6.4 Hz, 2H), 2.40 (q, J=8 Hz, 4H), 2.30 (m, 4H), 2.17 (s, 6H), 1.95-1.41 (m, 24H), 1.48-1.26 (m, 37H), 0.87 (t, J=6.4 Hz, 8H) ppm. MS (m+1)=948.4, Rt=1.10 min (LC Method 4).

Synthesis of Example 25: 8-(4-((5-((4,4-Bis(octyloxy)butanoyl)oxy)pentyl)oxy)-3-(((4-(dimethylamino)butanoyl)oxy)methyl)phenoxy)octyl Decanoate Intermediate 25a: 2-((5-((Tert-butyldimethylsilyl)oxy)pentyl)oxy)-5-hydroxybenzaldehyde

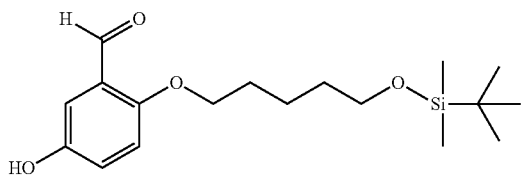 [SMILES: CC(C)(C)[Si](C)(C)OCCCCCOc1ccc(O)cc1C=O]

Can be prepared using similar method to that employed for the synthesis of Intermediate 20b from 2,5-dihydroxybenzaldehyde and 5-((tert-butyldimethylsilyl)oxy)pentyl methanesulfonate. TLC: EtOAc: Hexanes (2:8): Rf=0.9.

Intermediate 25b: 8-(3-Formyl-4-((5-hydroxypentyl)oxy)phenoxy)octyl Decanoate

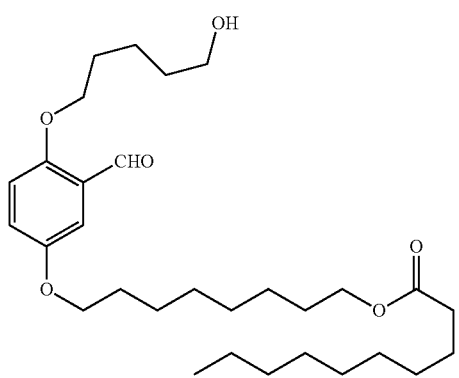 [SMILES: CCCCCCCCCC(=O)OCCCCCCCCOc1ccc(OCCCCCO)c(C=O)c1]

To a solution of Intermediate 25a in DMF (40 ml) were added 8-((methylsulfonyl)oxy)octyl decanoate (3.3 g, 8.86 mmol) and $K_2CO_3$ (1.6 g, 11.81 mmol) followed by TBAI (500 mg, 0.74 mmol) and heated to 100° C. for 3 h under nitrogen atmosphere. Progress of the reaction was monitored by TLC. Reaction mixture was diluted with water (100 ml), Extracted with EtOAc (2×150 ml), combined organic layers were washed with brine (200 ml), dried over $Na_2SO_4$ and concentrated under reduced pressure, to obtain a pale brown liquid. The product was purified by flash-chromatography (Silica gel 100-200 mesh). Product was eluted at 20% EtOAc in Hexanes to give 1.2 g (41% yield) an off-white solid. TLC: EtOAc: Hexanes (2:8): Rf=0.6.

Intermediate 25c: 8-(4-((5-((4,4-Bis(octyloxy)butanoyl)oxy)pentyl)oxy)-3-formylphenoxy)octyl Decanoate

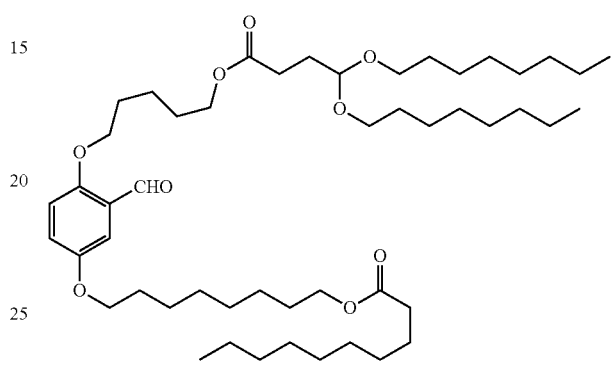

To a solution of Intermediate 25b (300 mg, 0.59 mmol) in DCM (20 ml) were added 4,4-bis(octyloxy)butanoic acid (305 mg, 0.88 mmol), EDC.HCl (227 mg, 1.18 mmol), DIPEA (0.31 ml, 1.77 mmol) followed by DMAP (72 mg, 0.59 mmol) and stirred for 18 h at 25° C. under nitrogen atmosphere. Progress of the reaction was monitored by TLC. Reaction mixture was diluted with water (100 ml), extracted with DCM (2×50 ml), combined organic layers were washed with brine (100 ml), dried over $Na_2SO_4$ and concentrated under reduced pressure, to obtain a pale green liquid. The product was purified by flash-chromatography (Silica gel 230-400 mesh). Product was eluted at 5% Methanol in DCM to give 300 mg (61% yield) of pale green liquid. TLC: MeOH:DCM (1:9): Rf=0.5.

Intermediate 25d: 8-(4-((5-((4,4-Bis(octyloxy)butanoyl)oxy)pentyl)oxy)-3-(hydroxymethyl)phenoxy)octyl Decanoate

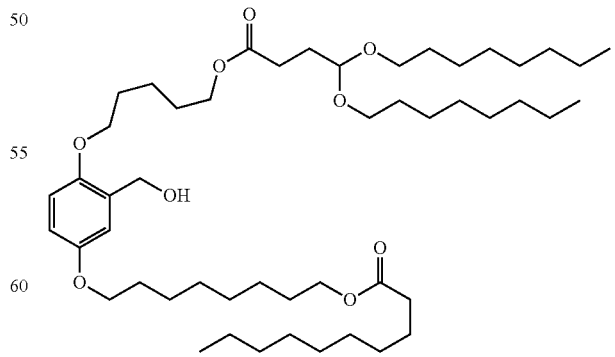

Can be prepared using similar method to that employed for the synthesis of Intermediate 20e from Intermediate 25c. TLC: EtOAc: Hexanes (2:8): Rf=0.4.

Example 25: 8-(4-((5-((4,4-Bis(octyloxy)butanoyl)oxy)pentyl)oxy)-3-(((4-(dimethylamino)butanoyl)oxy)methyl)phenoxy)octyl Decanoate

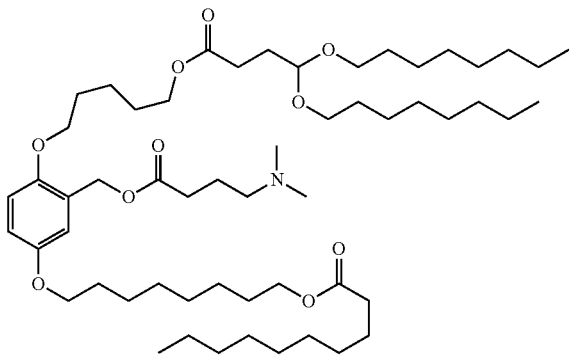 [SMILES: CCCCCCCCCC(=O)OCCCCCCCCOc1ccc(OCCCCCOC(=O)CCC(OCCCCCCCC)OCCCCCCCC)c(COC(=O)CCCN(C)C)c1]

To a solution of Intermediate 25d (0.3 g, 0.359 mmol) in DCM (10 ml) was added EDC.HCl (137.7 mg, 0.718 mmol), DIPEA (0.18 ml, 1.07 mmol), DMAP (43.8 mg, 0.359 mmol), and N, N-dimethylaminobutyricacid.HCl (90.3 mg, 0.538 mmol). The mixture was stirred for 18 h at 25° C. under nitrogen atmosphere. Progress of the reaction was monitored by TLC. Reaction mixture was diluted with water (200 ml), extracted with DCM (2×150 ml), combined organic layers were washed with brine (100 ml), dried over $Na_2SO_4$ and concentrated under reduced pressure, to obtain a pale green liquid. The product was purified by flash-chromatography (Silica gel 230-400 mesh). Product was eluted at 5% Methanol in DCM to give 150 mg (44% yield) of a pale green liquid. $^1$H NMR (400 MHz, $CDCl_3$): δ 6.89 (s, 1H), 6.77 (s, 2H), 5.14 (s, 2H), 4.48 (t, J=4 Hz, 1H), 4.10-4.04 (m, 4H), 3.94-3.87 (m, 4H), 3.55 (q, J=6.4 Hz, 2H), 3.41 (q, J=6.8 Hz, 2H), 2.40 (q, J=7.6 Hz, 4H), 2.29 (m, 4H), 2.21 (s, 6H), 1.95-1.43 (m, 24H), 1.49-1.26 (m, 37H), 0.86 (t, J=6.4 Hz, 8H) ppm. MS (m+1)=948.4, Rt=1.09 min (LC Method 4).

Synthesis of Example 26: ((4-(((1,4-Dimethylpiperidine-4-carbonyl)oxy)methyl)-1,3-phenylene)bis(oxy))bis(octane-8,1-diyl) bis(decanoate)

Intermediate 26a: 8-Hydroxyoctyl Decanoate

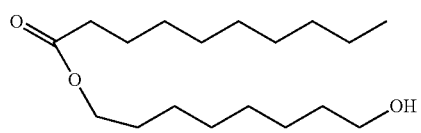 [SMILES: CCCCCCCCCC(=O)OCCCCCCCCO]

The Intermediate 26a can be prepared using similar method to that employed for the synthesis of Intermediate 17a from capric acid and 1,8-octane diol. TLC: EtOAc:Hexanes (4:6): Rf=0.6.

Intermediate 26b: 8-((Methylsulfonyl)oxy)octyl Decanoate

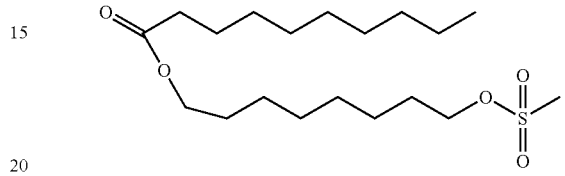

The Intermediate 26b can be prepared using similar method to that employed for the synthesis of Intermediate 20a from Intermediate 26a. TLC: EtOAc:Hexanes (2:8): Rf=0.5.

Intermediate 26c: ((4-formyl-1,3-phenylene)bis(oxy))bis(octane-8,1-diyl) bis(decanoate)

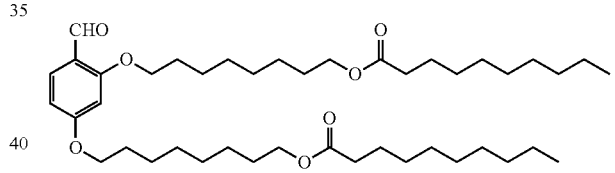

The Intermediate 26c can be prepared using similar method to that employed for the synthesis of Intermediate 20b from Intermediate 26b. TLC: EtOAc:Hexanes (2:8): Rf=0.6.

Intermediate 26d: ((4-(Hydroxymethyl)-1,3-phenylene)bis(oxy))bis(octane-8,1-diyl) bis(decanoate)

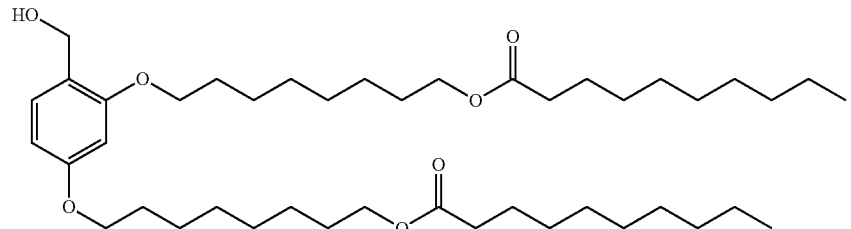

Chemical Formula : $C_{43}H_{76}O_7$
Molecular Weight: 705.06

The Intermediate 26d can be prepared using similar method to that employed for the synthesis of Intermediate 20e with Intermediate 26c. TLC: EtOAc:Hexanes (2:8): Rf=0.4.

Example 26: ((4-(((1,4-Dimethylpiperidine-4-carbonyl)oxy)methyl)-1,3-phenylene)bis(oxy))bis(octane-8,1-diyl) bis(decanoate)

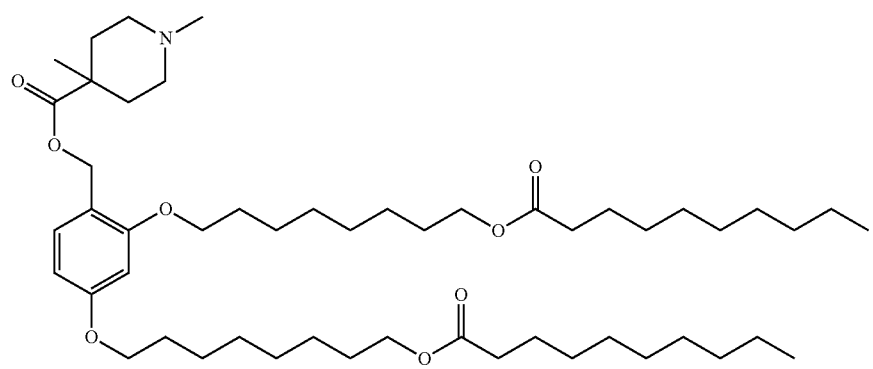 [SMILES: CCCCCCCCCC(=O)OCCCCCCCCOc1ccc(COC(=O)C2(C)CCN(C)CC2)c(OCCCCCCCCOC(=O)CCCCCCCCC)c1]

To a cold solution of 1,4-dimethylpiperidine-4-carboxylic acid (167 mg, 1.06 mmol) in DCM (15 ml) were added triethylamine (0.40 ml, 2.83 mmol) followed by 2,4,6-trifluorobenzoylchloride (0.17 ml, 1.06 mmol) and stirred for 2 h at 25° C. under nitrogen atmosphere. After which time Intermediate 26d (500 mg, 0.70 mmol) in DCM (5 ml) was added and the resulting reaction mixture stirred for another 2 h at 25° C. Progress of the reaction was monitored by TLC. Reaction mixture was diluted with water (100 ml), extracted with DCM (2×50 ml), combined organic layers were washed with brine (100 ml), dried over $Na_2SO_4$ and concentrated under reduced pressure, to afford a pale green liquid. The product was purified by flash-chromatography (Silica gel 230-400 mesh). Product was eluted at 5% methanol in DCM to give 510 mg (85% yield) of a pale green liquid. $^1$H NMR (400 MHz, $CDCl_3$): δ=7.17 (d, J=8.4 Hz, 1H), 6.41 (d, J=6.8 Hz, 2H), 5.07 (s, 2H), 4.03 (t, J=7.2 Hz, 4H), 3.91 (t, J=6 Hz, 4H), 2.62 (bs, 2H), 2.282-2.231 (m, 7H), 2.18-2.06 (m, 4H), 1.78-1.11 (m, 57H), 0.84 (t, J=6.8 Hz, 6H) ppm. MS (m+1)=844.3, Rt=1.02 min (LC Method 4).

Example 27 and Example 28 can be prepared using similar coupling methods to those employed for the synthesis of Example 26 with the appropriate carboxylic acid coupling partner:

Example 27: ((4-(((4-(Dimethylamino)butanoyl)oxy)methyl)-1,3-phenylene)bis(oxy))bis(octane-8,1-diyl) bis(decanoate)

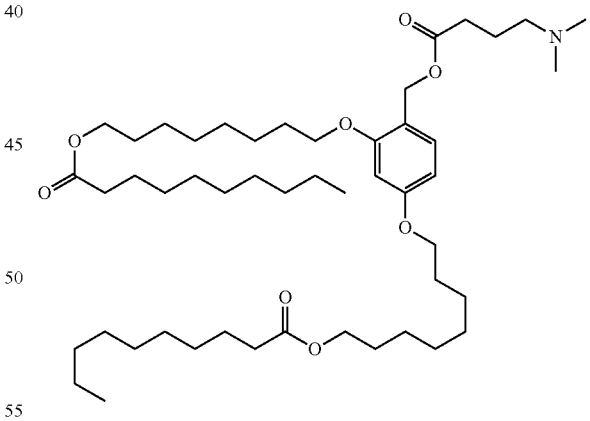

$^1$H NMR (400 MHz, $CDCl_3$): δ=7.21 (d, J=8.9 Hz, 1H), 6.41-6.47 (m, 2H), 5.10 (s, 2H), 4.07 (td, J=6.7, 0.9 Hz, 4H), 3.95 (t, J=6.5 Hz, 4H), 2.36 (t, J=7.5 Hz, 2H), 2.30 (t, J=7.6 Hz, 6H), 2.22 (s, 6H), 1.73-1.86 (m, 6H), 1.58-1.69 (m, 8H), 1.41-1.51 (m, 4H), 1.33-1.41 (m, 12H), 1.19-1.33 (m, 24H), 0.85-0.92 (m, 6H). MS (m+1)=818.6, Rt=1.02 min (LC Method 6).

Example 28: ((4-(((4-(Diethylamino)butanoyl)oxy)methyl)-1,3-phenylene)bis(oxy))bis(octane-8,1-diyl) bis(decanoate)

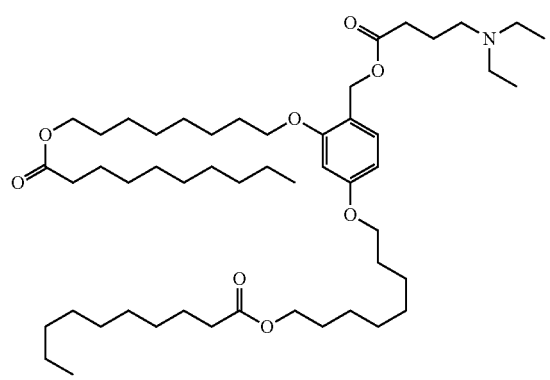 [SMILES: CCCCCCCCCC(=O)OCCCCCCCCOc1ccc(COC(=O)CCCN(CC)CC)c(OCCCCCCCCOC(=O)CCCCCCCCC)c1]

$^1$H NMR (400 MHz, CDCl$_3$): δ=7.17-7.24 (m, 1H), 6.40-6.47 (m, 2H), 5.10 (s, 2H), 4.07 (td, J=6.7, 1.2 Hz, 4H), 3.94 (td, J=6.5, 1.1 Hz, 4H), 2.33-2.87 (br s, 6H), 2.37 (t, J=7.2 Hz, 2H), 2.30 (t, J=7.5 Hz, 4H), 1.71-1.93 (m, 6H), 1.55-1.70 (m, 8H), 1.41-1.52 (m, 4H), 1.33-1.41 (m, 12H), 1.19-1.33 (m, 24H), 0.96-1.19 (br s, 6H), 0.83-0.93 (m, 6H). MS (m+1)=846.6, Rt=1.03 min (LC Method 6).

mRNA's

Brief Description of mRNA Transcription Protocol

A circular plasmid DNA template is constructed that contains a mRNA transcription cassette consisting of the following features: a consensus T7 bacteriophage DNA-dependent RNA polymerase promoter, a 5' untranslated region (UTR), a Kozak sequence, and open reading frame, a 3' UTR, and a 120 nucleotide long polyadenosine (polyA120) tail. The plasmid DNA template is propagated in E. coli, isolated, and linearized by restriction enzyme digest immediately 3' of the poly120 tail. The plasmid DNA is combined with T7 RNA polymerase, ribonucleotide triphosphates, RNase inhibitor, pyrophosphatase enzyme, dithiothreitol, spermidine, and enzyme reaction buffer and is incubated for 1 hour at 37° C. DNase I enzyme is added to digest the plasmid DNA template and is incubated for 0.5 hours at 37° C. mRNA is isolated by sequential precipitation with lithium chloride, washing of the pellet in 70% ethanol, resuspension of the mRNA pellet in water, re-precipitation with isopropanol and sodium acetate, and washing of the pellet again in 70% ethanol. The final mRNA pellet is resuspended in water.

| Reagent | Concentration | Notes |
| --- | --- | --- |
| Nuclease-free water | Remaining volume | |
| Tris-HCl pH 8.0 (mM) | 40 | |
| MgCl$_2$ (mM) | 20 | |
| ATP, CTP, GTP, UTP (mM) | 4 | |
| Pseudouridine (mM) | 4 | To make 100% PsU mRNA, do not include UTP in reaction. To make 100% unmodified mRNA, do not include PsU in reaction |
| DTT (mM) | 10 | |
| Spermidine (mM) | 2 | |
| Linearized plasmid DNA (ug/ul) | 0.05 | |
| Pyrophosphatase (U/ul) | 0.004 | |
| RNase inhibitor (U/ul) | 1 | |
| T7 RNA polymerase (U/ul) | 5 | |
| DNase I (U/ul) | 0.04 | |

TEV-hLeptin-GAopt-2xhBG-120A (SEQ ID NO:7)
Sequence features:
Tobacco Etch Virus (TEV) 5' UTR: 14-154
Optimal Kozak sequence: 155-163
Human leptin encoding amino acids 1-167 of Protein Accession # NP_000221, sequence codon optimized by GeneArt: 164-664
2 stop codons: 665-670
2 copies of human beta-globin 3'UTR: 689-954
120 nucleotide polyA tail: 961-1080

GGGAGACGCGUGUUAAAUAACAAAUCUCAACACAACAUAUACAAAACAA

ACGAAUCUCAAGCAAUCAAGCAUUCUACUUCUAUUGCAGCAAUUUAAAU

CAUUUCUUUUAAAGCAAAAGCAAUUUUCUGAAAAUUUUCACCAUUUACG

AACGAUAGCCGCCACCAUGCACUGGGGAACCCUGUGCGGAUUCCUGUGG

CUGUGGCCCUACCUGUUCUAUGUGCAAGCCGUGCCCAUCCAGAAGGUGC

AGGACGACACCAAGACCCUGAUCAAGACCAUCGUGACCCGGAUCAACGA

CAUCAGCCACACCCAGAGCGUGUCCAGCAAGCAGAAAGUGACCGGCCUG

GACUUCAUCCCCGGCCUGCACCCUAUCCUGACCCUGUCCAAGAUGGACC

AGACCCUGGCCGUGUACCAGCAGAUCCUGACCAGCAUGCCCAGCCGGAA

CGUGAUCCAGAUCAGCAACGACCUGGAAAACCUGCGGGACCUGCUGCAC

GUGCUGGCCUUCAGCAAGAGCUGCCAUCUGCCUUGGGCCAGCGGCCUGG

AAACCCUGGAUUCUCUGGGCGGAGUGCUGGAAGCCAGCGGCUACUCUAC

AGAGGUGGUGGCCCUGAGCAGACUGCAGGGCAGCCUGCAGGAUAUGCUG

UGGCAGCUGGAUCUGAGCCCCGGCUGCUAAUAGCGGACCGGCGAUAGAU

GAAGCUCGCUUUCUUGCUGUCCAAUUUCUAUUAAAGGUUCCUUUGUUCC

CUAAGUCCAACUACUAAACUGGGGGAUAUUAUGAAGGGCCUUGAGCAUC

UGGAUUCUGCCUAAUAAAAAACAUUUAUUUUCAUUGCAGCUCGCUUUCU

UGCUGUCCAAUUUCUAUUAAAGGUUCCUUUGUUCCCUAAGUCCAACUAC

UAAACUGGGGGAUAUUAUGAAGGGCCUUGAGCAUCUGGAUUCUGCCUAA

UAAAAAACAUUUAUUUUCAUUGCGGCCGCAAAAAAAAAAAAAAAAAAAA

AAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAA

AA

Biological Evaluation

Packaging of mRNA

All equipment and disposable supplies are certified free of RNase activity by the manufacturer or rendered RNase free by use of the RNaseZap reagent (LifeTechnologies). mRNA is encapsulated at a cationic lipid amine to mRNA phosphate (N:P) molar ratio of 4:1. Lipids (cationic lipid, DSPC, cholesterol and lipidated PEG or stealth lipid) are dissolved in ethanol. The molar ratios are 40:10:38:2, respectively. The mixture is sonicated briefly, then gently agitated for 5 minutes and then maintained at 37° C. until use. mRNA is exchanged into citrate buffer pH 5.8-6.0 by use of Amicon Ultra-15 centrifugal concentrators, and the final concentration is adjusted to 0.5 mg/ml and held at 37° C. until use. An equal volume of lipids in ethanol, mRNA in citrate buffer, and citrate buffer alone are drawn into disposable syringes. Tubing leading from syringes containing lipids and mRNA are attached to the T junction, and tubing leading from the syringe containing citrate buffer alone is paired with the tubing exiting the T-junction over a collection vessel containing a stir bar on an active stir plate. Syringes are placed in a syringe pump set to expel contents at a flow rate of 1 ml per minute.

The pump is activated, and the collected mRNA in lipid nanoparticles is transferred to SnakeSkin dialysis tubing (10,000 MWCO, Thermo Scientific). Material is dialyzed against RNAse- and pyrogen-free 1× phosphate buffered saline overnight at 4° C.

Packaging of siRNA

The lipid nanoparticles (LNPs) were formed by mixing equal volumes of lipids dissolved in alcohol with siRNA dissolved in a citrate buffer by an impinging jet process. The lipid solution contains a cationic lipid compound of the invention, a helper lipid (cholesterol), an optional neutral lipid (DSPC) and a stealth lipid (S010, S024, S027, or S031) at a concentration of 8-16 mg/mL with a target of 12 mg/mL in an alcohol. The siRNA to total lipid ratio is approximately 0.05 (wt/wt). Where a LNP formulation contains four lipid components, the molar ratios of the lipids ranges from 20 to 70 mole percent for the cationic lipid with a target of 40-60, the mole percent of helper lipid ranges from 20 to 70 with a target of 30 to 50, the mole percent of neutral lipid ranges from 0-30, the mole percent of PEG lipid has a range from 1 to 6 with a target of 2 to 5. The concentration of siRNA solution ranges from 0.7 to 1.0 mg/mL with a target of 0.8 to 0.9 mg/mL in a sodium citrate: sodium chloride buffer pH 4-6, with a target of 4.5-5.5. The LNPs are formed by mixing equal volumes of lipid solution in ethanol with siRNA dissolved in a citrate buffer by an impinging jet process through a mixing device with ID ranging from 0.25 to 2.0 mm at a flow rate from 10 to 640 mL/min. The mixed LNP solution is held at room temperature for 0-24 hrs prior to a dilution step. The solution is then concentrated and diafiltered with suitable buffer by ultrafiltration process using membranes with a MW cutoff from 30 to 500 KD. The final product is sterile filtered and stored at 4° C.

Measurement of mRNA Encapsulation

Percent encapsulation of mRNA in lipid nanoparticles is determined using the Quant-iT Ribogreen RNA Assay kit (Life Technologies). The LNP-mRNA suspension is assayed in buffer (mRNA outside the particle), and buffer plus Triton X-100 detergent (total mRNA). The difference calculated is the mRNA inside the particle. Prepare a 1000 ng/mL stock from the RNA provided in the kit and use this to generate a standard curve (0 ng/ml, 15.63-1000 ng/ml) in TE and TE+0.75% Triton X-100. Prepare LNP-mRNA samples in TE buffer and TE buffer+0.75% Triton X-100 with appropriate dilution so that reading is in the range of standard curve (400-2,000 fold). In a 384-well plate (Costar non-treated #3573) add 0.04 ml of standard (in duplicate) or sample (in triplicate) per well. Dilute Ribogreen reagent 240-fold in TE buffer and add 0.06 ml per well. Mix contents of wells and measure fluorescence (excitation=480 nm, emission=520 nm). Subtract background values (no RNA) from standard and test sample values and determine the concentrations of RNA in the samples using the standard curves. Determine the percent encapsulation of the sample by dividing the difference in concentrations between sample+triton and sample in buffer alone by the sample+triton concentration.

Encapsulation Data

TABLE 2

In-vitro encapsulation data for mRNA

| Example | % encapsulation (mRNA Leptin) | $Log_{10}$ (IgG titer), 1 ng RNA (RSV-F), 2 weeks post $2^{nd}$ immunization |
|---|---|---|
| 1 | 73.3 | 4.43 |
| 5 | 59.0 | |
| 6 | | 4.25 |
| 7 | 95.4 | 4.37 |
| 12 | | 4.40 |
| 14 | 77.9 | 3.85 |
| 15 | | 2.81 |
| 16 | 85.1 | 4.40 |
| 19 | 84.3 | 4.68 |
| 20 | 88.4 | |
| 21 | 79.8 | |
| 22 | 86.0 | |
| 23 | 84.3 | |
| 26 | 90.8 | |
| 27 | 95.2 | |
| 28 | 93.6 | |

Immunological Data

1. Materials and Methods

RNA Replicons

Various replicons are used below. In general these are based on a venezuelan equine encephalitis virus (VEEV) based chimeric replicon (VCR), which is a hybrid alphavirus genome with non-structural proteins from VEEV, a packaging signal from sindbis virus, and a 3' UTR from Sindbis virus. In addition, we used a replicon based on the VEE live attenuated vaccine virus, TC-83. The replicons are about 10 kb long and have a poly-A tail.

Plasmid DNA encoding alphavirus replicons (named: vA375 (TC83R-FLFPD.RSVF-run off) or vA803 [VCR(ro)-X179A(TD)_HA]) served as a template for synthesis of RNA in vitro. The replicons contain the alphavirus genetic elements required for RNA replication but lack those encoding gene products necessary for particle assembly; the structural proteins are instead replaced by a protein of interest (e.g. an immunogen, such as full-length RSV F protein) and so the replicons are incapable of inducing the generation of infectious particles. A bacteriophage T7 promoter upstream of the alphavirus cDNA facilitates the synthesis of the replicon RNA in vitro. Following linearization of the plasmid DNA with a suitable restriction endonuclease, run-off transcripts were synthesized in vitro using T7 bacteriophage derived DNA-dependent RNA polymerase. Transcriptions were performed for 2 hours at 37° C. in the presence of 7.5 mM of each of the nucleoside triphosphates (ATP, CTP, GTP and UTP) following the instructions provided by the manufacturer (Ambion). Following transcription the template DNA was digested with TURBO DNase (Ambion). The replicon RNA was precipitated with LiCl and reconstituted in nuclease-free water. Uncapped RNA was capped post-transcriptionally with Vaccinia Capping Enzyme (VCE) using the ScriptCap m7G Capping System (Epicentre Biotechnologies) as outlined in the user manual; replicons capped in this way are given the "v" prefix e.g. vA317 is the A317 replicon capped by VCE. Post-transcriptionally capped RNA was precipitated with LiCl and reconstituted in nuclease-free water. The concentration of the RNA samples was determined by measuring $OD_{260\,nm}$. Integrity of the in vitro transcripts was confirmed by denaturing agarose gel electrophoresis.

Preparation of DlinDMA-based LNPs

RNA was encapsulated in LNPs made essentially by the methods as disclosed in Jeffs et al. (2005) *Pharmaceutical Research* 22 (3):362-372 and Maurer et al. (2001) *Biophysical Journal*, 80: 2310-2326. The LNPs were made of 10% DSPC (zwitterionic), 40% cationic lipid, 48% cholesterol and 2% PEG-conjugated DMG (2 kDa PEG). These proportions refer to the moles in the total LNP.

DSPC (1,2-Diastearoyl-sn-glycero-3-phosphocholine) was purchased from Genzyme. Cholesterol was obtained from Sigma-Aldrich. PEG-conjugated DMG (1,2-dimyristoyl-sn-glycero-3-phosphoethanolamine-N-[methoxy(polyethylene glycol), ammonium salt), DOTAP (1,2-dioleoyl-3-trimethylammonium-propane, chloride salt) and DC-chol (3β-[N—(N',N'-dimethylaminoethane)-carbamoyl]cholesterol hydrochloride) were from Avanti Polar Lipids.

Briefly, lipids were dissolved in ethanol (2ml), a RNA replicon was dissolved in buffer (2 ml, 100 mM sodium citrate, pH 6) and these were mixed with 2 ml of buffer followed by 1 hour of equilibration. The mixture was then dialized overnight against 1×PBS. The resulting product contained liposomes, with ~70-95% encapsulation efficiency.

For immunization in ferrets, a lipid working solution was freshly prepared by dissolving 22.5 mg of Example 1, 5.9 mg of DSPC, 13.9 mg of Cholesterol and 4.0 mg of PEG2000-conjugated DMPE (cat #880150P, Avanti Polar Lipids, Inc.) in 10 ml ethanol. A 10 mL working solution of RNA was also prepared at a concentration of 0.125 mg/ml in 100 mM citrate buffer (pH 6). The working lipid and RNA solutions were heated at 37° C. for 5 min before being loaded into two 10 cc luer-lok syringes. Subsequently, the two syringes were connected to a Tee-mixer (PEEK™ 500 μm ID junction) using FEP tubing (fluorinated ethylene-propylene; all FEP tubing used had a 2 mm internal diameter and a 3 mm outer diameter; obtained from Idex Health Science). The outlet from the T mixer was also FEP tubing separately, 10 mL of citrate buffer (pH 6) was loaded in a third 10 cc syringe which was connected to a separate piece of tubing. All three syringes were loaded on a syringe pump and driven at 1.0 ml/min. The tubing outlets were positioned to collect the mixtures in a 20 mL glass vial which was gently stirred using a stirring bar. All glass vials were baked at 250° C. for 12 hours prior to experiment to completely inactivate any RNase contaminant. At the end of mixing, the stir bar was taken out and the ethanol/aqueous solution was allowed to equilibrate to room temperature for 1 hour. After incubation, the ethanol/aqueous solution was loaded into a syringe, and mixed with equal volume of 100 mM citrate buffer (pH 6) using the aforementioned Tee-junction process. Next, LNPs were concentrated to 20 mL and dialyzed against 10-15 volumes of 1× PBS using by tangential flow filtration before recovering the final product. The TFF system and hollow fiber filtration membranes were purchased from Spectrum Labs (Rancho Dominguez) and were used according to the manufacturer's guidelines. Polysulfone hollow fiber filtration membranes with a 100 kD pore size cutoff and 8 cm$^2$ surface area were used. For in vitro and in vivo experiments formulations were diluted to the required RNA concentration with 1×. PBS.

Encapsulation Efficiency of RNA Replicons

The percentage of encapsulated RNA and RNA concentration were determined by Quant-iT RiboGreen RNA reagent kit (Invitrogen), following manufacturer's instructions. The ribosomal RNA standard provided in the kit was used to generate a standard curve. LNPs were diluted 10× or 100× in 1× TE buffer (from kit) before addition of the dye. Separately, LNPs were diluted 10× or 100× in 1× TE buffer containing 0.5% Triton X before addition of the dye (to disrupt the LNPs and thus to assay total RNA). Thereafter an equal amount of dye was added to each solution and then ~180 μL of each solution after dye addition was loaded in duplicate into a 96 well tissue culture plate. The fluorescence (Ex 485 nm, Em 528 nm) was read on a microplate reader. All LNP formulations were dosed in vivo based on the encapsulated amount of RNA.

2. Characterization of the Lipid Nanoparticle (LNP) Formulations

Z average particle diameter and polydispersity index are shown in Table 3:

TABLE 3

| Compound | Zav (nm) | polydispersity |
|---|---|---|
| 1 | 135.3 | 0.11 |
| 7 | 100.7 | 0.096 |
| 9 | 182.6 | 0.369 |
| 12 | 97.3 | 0.116 |
| 14 | 127.7 | 0.102 |
| 15 | 138.8 | 0.210 |
| 16 | 115.5 | 0.108 |
| 19 | 133.2 | 0.074 |

3. Immunogenicity in Mouse Models (RSV)

The vA375 self-replicating replicon encoding RSV F protein was administered to BALB/c mice, 8 animals per group, by bilateral intramuscular vaccinations (50 μL per leg) on days 0 and 21 with the replicon (1 ng) formulated as LNPs with the lipids described below. All LNPs tested were composed of 40% cationic lipid, 10% DSPC, 48% cholesterol and 2% PEG-DMG with similar amounts of RNA. The LNPs were all prepared using the same technique. The LNP formulations were prepared and stored at 4° C. for the prime and the boost immunizations.

Serum was collected for antibody analysis on days 14, 36 and 49. As shown in Table 4, the LNP formulations tested generated immune responses with as little as 1 ng of self-replicating RNA, as determined by increased F-specific IgG titers.

TABLE 4

| Example | Encapsulation efficiency (RNA %) | $Log_{10}$(IgG titer), 1 ng RNA (RSV-F), 2 weeks post $2^{nd}$ immunization |
|---|---|---|
| 1 | 96.6 | 4.43 |
| 2 | 13.1 | 4.14 (100 ng dose)* |

TABLE 4-continued

| Example | Encapsulation efficiency (RNA %) | Log$_{10}$(IgG titer), 1 ng RNA (RSV-F), 2 weeks post 2$^{nd}$ immunization |
|---|---|---|
| 3 | 85.0 | 4.77 (100 ng dose)* |
| 6 | 71.3 | 4.25 |
| 7 | 85.6 | 4.37 |
| 9 | 69.1 | Not tested |
| 12 | 89.8 | 4.40 |
| 13 | 92.1 | Not tested |
| 14 | 78.3 | 3.85 |
| 15 | 82.6 | 2.81 |
| 16 | 88.0 | 4.40 |
| 19 | 79.9 | 4.68 |

4. Immunogenicity in Ferret Models (Influenza)

A total of seven experimental groups with six animals per group (42 animals) were used in this study; two vaccine doses of each RNA formulation (Groups 2-5), two groups vaccinated with a non-adjuvated (H1N1 subunit) or an adjuvated (MF59/H1N1 subunit) commercially available H1N1 influenza subunit vaccine (Groups 6 and 7) and a mock vaccinated group (Group 1). The RNA test vaccines were derived from a recombinant DNA plasmid (pDNA) carrying an alphavirus genome in which the structural genes were replaced with the HA gene from the H1N1 influenza A strain, Ca107. The RNA was then formulated in either cationic oil-in-water emulsion (CNE) or LNP for delivery to host cells via intramuscular (IM) injection. RNA concentrations for each formulation study group were 15 and 45 mcg for CNE and 5 and 15 mcg for LNP. The H1N1 subunit vaccines were used at a HA subunit protein concentration of 15 mcg. Non-vaccinated animals were mock vaccinated with a vehicle control for the RNA test vaccines. All test vaccines were administered by IM injection on Study Days (SD) 0 followed with a booster vaccination on Study Day 56 (8 weeks post 1st immunization).

Table 5 summarizes Influenza microneutralization data and table 6 the haemagultanin inhibition (HAI) titers. The LNP formulation tested generated immune responses with as little as 5 μg of self-amplifying RNA, as determined by increased HA-specific neutralization and HAI titers.

TABLE 5

| | Animal | Pre-bleed | 4wp1 | 8wp1 | 4wp2 |
|---|---|---|---|---|---|
| Vehicle control | 1001 | <10 | <10 | <10 | <10 |
| | 1002 | <10 | <10 | <10 | <10 |
| | 1003 | <10 | <10 | <10 | <10 |
| | 1004 | <10 | <10 | <10 | <10 |
| | 1005 | <10 | <10 | <10 | <10 |
| | 1006 | <10 | <10 | <10 | <10 |
| 15 mcg CNE | 2001 | <10 | 40 | 40 | 640 |
| | 2002 | <10 | <10 | <10 | 160 |
| | 2003 | <10 | 20 | 40 | 80 |
| | 2004 | <10 | <10 | <10 | 80 |
| | 2005 | <10 | <10 | <10 | 80 |
| | 2006 | <10 | 10 | <10 | 160 |
| 45 mcg CNE | 3001 | <10 | <10 | 10 | >1280 |
| | 3002 | <10 | 40 | 10 | >1280 |
| | 3003 | <10 | 40 | 20 | 160 |
| | 3004 | <10 | <10 | <10 | 640 |
| | 3005 | <10 | <10 | <10 | 320 |
| | 3006 | <10 | 20 | 10 | >20480 |
| 5 mcg (Example 1) | 4001 | <10 | 20 | 20 | 640 |
| | 4002 | <10 | 80 | 40 | >20480 |
| | 4003 | <10 | 20 | 20 | >20480 |
| | 4004 | <10 | 40 | 40 | >20480 |
| | 4005 | <10 | 10 | 10 | 320 |
| | 4006 | <10 | 40 | <10 | 640 |
| 15 mcg (Example1) | 5001 | <10 | 160 | 40 | 640 |
| | 5002 | <10 | 160 | 80 | >20480 |
| | 5003 | <10 | 320 | 80 | 640 |
| | 5004 | <10 | 80 | 40 | 640 |
| | 5005 | <10 | 80 | 40 | >20480 |
| | 5006 | <10 | 40 | 20 | 640 |
| 15 mcg H1N1 subunit | 6001 | <10 | <10 | <10 | 20 |
| | 6002 | <10 | <10 | <10 | 40 |
| | 6003 | <10 | 10 | 40 | 80 |
| | 6004 | <10 | <10 | 20 | 80 |
| | 6005 | <10 | <10 | <10 | 40 |
| | 6006 | <10 | <10 | <10 | <10 |
| 15 mcg MF59/ H1N1 subunit | 7001 | <10 | 40 | 20 | 1280 |
| | 7002 | <10 | 80 | 80 | 5120 |
| | 7003 | <10 | 160 | 160 | >20480 |
| | 7004 | <10 | 40 | 80 | 10240 |
| | 7005 | <10 | 160 | 160 | >20480 |
| | 7006 | <10 | 80 | 160 | >20480 |

Table 6 summarizes Influenza HAI data based on the ferret model:

TABLE 6

| | Animal | Pre-bleed | 4wp1 | 8wp1 | 4wp2 |
|---|---|---|---|---|---|
| Vehicle control | 1001 | <10 | <10 | <10 | <10 |
| | 1002 | <10 | <10 | <10 | <10 |
| | 1003 | <10 | <10 | <10 | <10 |
| | 1004 | <10 | <10 | <10 | <10 |
| | 1005 | <10 | <10 | <10 | <10 |
| | 1006 | <10 | <10 | <10 | <10 |
| 15 mcg CNE | 2001 | <10 | 40 | 40 | 640 |
| | 2002 | <10 | <10 | <10 | 160 |
| | 2003 | <10 | 20 | 40 | 80 |
| | 2004 | <10 | <10 | <10 | 80 |
| | 2005 | <10 | <10 | <10 | 80 |
| | 2006 | <10 | 10 | <10 | 160 |
| 45 mcg CNE | 3001 | <10 | <10 | 10 | >1280 |
| | 3002 | <10 | 40 | 10 | >1280 |
| | 3003 | <10 | 40 | 20 | 160 |
| | 3004 | <10 | <10 | <10 | 640 |
| | 3005 | <10 | <10 | <10 | 320 |
| | 3006 | <10 | 20 | 10 | >20480 |
| 5 mcg (Example 1) | 4001 | <10 | 20 | 20 | 640 |
| | 4002 | <10 | 80 | 40 | >20480 |
| | 4003 | <10 | 20 | 20 | >20480 |
| | 4004 | <10 | 40 | 40 | >20480 |
| | 4005 | <10 | 10 | 10 | 320 |
| | 4006 | <10 | 40 | <10 | 640 |
| 15 mcg (Example 1) | 5001 | <10 | 160 | 40 | 640 |
| | 5002 | <10 | 160 | 80 | >20480 |
| | 5003 | <10 | 320 | 80 | 640 |
| | 5004 | <10 | 80 | 40 | 640 |
| | 5005 | <10 | 80 | 40 | >20480 |
| | 5006 | <10 | 40 | 20 | 640 |
| 15 mcg H1N1 subunit | 6001 | <10 | <10 | <10 | 20 |
| | 6002 | <10 | <10 | <10 | 40 |
| | 6003 | <10 | 10 | 40 | 80 |
| | 6004 | <10 | <10 | 20 | 80 |
| | 6005 | <10 | <10 | <10 | 40 |
| | 6006 | <10 | <10 | <10 | <10 |
| 15 mcg MF59/ H1N1 subunit | 7001 | <10 | 40 | 20 | 1280 |
| | 7002 | <10 | 80 | 80 | 5120 |
| | 7003 | <10 | 160 | 160 | >20480 |
| | 7004 | <10 | 40 | 80 | 10240 |
| | 7005 | <10 | 160 | 160 | >20480 |
| | 7006 | <10 | 80 | 160 | >20480 |

APPENDIX: USEFUL PHOSPHOLIPIDS FOR LNP FORMULATIONS

DDPC 1,2-Didecanoyl-sn-Glycero-3-phosphatidylcholine
DEPA 1,2-Dierucoyl-sn-Glycero-3-Phosphate
DEPC 1,2-Erucoyl-sn-Glycero-3-phosphatidylcholine
DEPE 1,2-Dierucoyl-sn-Glycero-3-phosphatidylethanolamine
DEPG 1,2-Dierucoyl-sn-Glycero-3[Phosphatidyl-rac-(1-glycerol . . . )
DLOPC 1,2-Linoleoyl-sn-Glycero-3-phosphatidylcholine
DLPA 1,2-Dilauroyl-sn-Glycero-3-Phosphate
DLPC 1,2-Dilauroyl-sn-Glycero-3-phosphatidylcholine
DLPE 1,2-Dilauroyl-sn-Glycero-3-phosphatidylethanolamine
DLPG 1,2-Dilauroyl-sn-Glycero-3[Phosphatidyl-rac-(1-glycerol . . . )
DLPS 1,2-Dilauroyl-sn-Glycero-3-phosphatidylserine
DMG 1,2-Dimyristoyl-sn-glycero-3-phosphoethanolamine
DMPA 1,2-Dimyristoyl-sn-Glycero-3-Phosphate
DMPC 1,2-Dimyristoyl-sn-Glycero-3-phosphatidylcholine
DMPE 1,2-Dimyristoyl-sn-Glycero-3-phosphatidylethanolamine
DMPG 1,2-Myristoyl-sn-Glycero-3[Phosphatidyl-rac-(1-glycerol . . . )
DMPS 1,2-Dimyristoyl-sn-Glycero-3-phosphatidylserine
DOPA 1,2-Dioleoyl-sn-Glycero-3-Phosphate
DOPC 1,2-Dioleoyl-sn-Glycero-3-phosphatidylcholine
DOPE 1,2-Dioleoyl-sn-Glycero-3-phosphatidylethanolamine
DOPG 1,2-Dioleoyl-sn-Glycero-3[Phosphatidyl-rac-(1-glycerol . . . )
DOPS 1,2-Dioleoyl-sn-Glycero-3-phosphatidylserine
DPPA 1,2-Dipalmitoyl-sn-Glycero-3-Phosphate
DPPC 1,2-Dipalmitoyl-sn-Glycero-3-phosphatidylcholine
DPPE 1,2-Dipalmitoyl-sn-Glycero-3-phosphatidylethanolamine
DPPG 1,2-Dipalmitoyl-sn-Glycero-3[Phosphatidyl-rac-(1-glycerol . . . )
DPPS 1,2-Dipalmitoyl-sn-Glycero-3-phosphatidylserine
DPyPE 1,2-diphytanoyl-sn-glycero-3-phosphoethanolamine
DSPA 1,2-Distearoyl-sn-Glycero-3-Phosphate
DSPC 1,2-Distearoyl-sn-Glycero-3-phosphatidylcholine
DSPE 1,2-Diostearpyl-sn-Glycero-3-phosphatidylethanolamine
DSPG 1,2-Distearoyl-sn-Glycero-3[Phosphatidyl-rac-(1-glycerol . . . )
DSPS 1,2-Distearoyl-sn-Glycero-3-phosphatidylserine
EPC Egg-PC
HEPC Hydrogenated Egg PC
HSPC High purity Hydrogenated Soy PC
HSPC Hydrogenated Soy PC
LYSOPC MYRISTIC 1-Myristoyl-sn-Glycero-3-phosphatidylcholine
LYSOPC PALMITIC 1-Palmitoyl-sn-Glycero-3-phosphatidylcholine
LYSOPC STEARIC 1-Stearoyl-sn-Glycero-3-phosphatidylcholine
Milk Sphingomyelin MPPC 1-Myristoyl,2-palmitoyl-sn-Glycero 3-phosphatidylcholine
MSPC 1-Myristoyl,2-stearoyl-sn-Glycero-3-phosphatidylcholine
PMPC 1-Palmitoyl,2-myristoyl-sn-Glycero-3-phosphatidylcholine
POPC 1-Palmitoyl,2-oleoyl-sn-Glycero-3-phosphatidylcholine
POPE 1-Palmitoyl-2-oleoyl-sn-Glycero-3-phosphatidylethanolamine
POPG 1,2-Dioleoyl-sn-Glycero-3[Phosphatidyl-rac-(1-glycerol) . . . ]
PSPC 1-Palmitoyl,2-stearoyl-sn-Glycero-3-phosphatidylcholine
SMPC 1-Stearoyl,2-myristoyl-sn-Glycero-3-phosphatidylcholine
SOPC 1-Stearoyl,2-oleoyl-sn-Glycero-3-phosphatidylcholine
SPPC 1-Stearoyl,2-palmitoyl-sn-Glycero-3-phosphatidylcholine

---

SEQUENCE LISTING

```
<160> NUMBER OF SEQ ID NOS: 1

<210> SEQ ID NO 1
<211> LENGTH: 1080
<212> TYPE: RNA
<213> ORGANISM: Tobacco etch virus
<220> FEATURE:
<221> NAME/KEY: 5'UTR
<222> LOCATION: (14)..(154)
<220> FEATURE:
<221> NAME/KEY: misc_feature
<222> LOCATION: (155)..(163)
<223> OTHER INFORMATION: Optimal Kozak sequence
<220> FEATURE:
<221> NAME/KEY: misc_feature
<222> LOCATION: (665)..(670)
<223> OTHER INFORMATION: 2 stop codons
<220> FEATURE:
<221> NAME/KEY: 3'UTR
<222> LOCATION: (689)..(954)
<223> OTHER INFORMATION: 2 copies of human beta-globin 3'UTR
<220> FEATURE:
<221> NAME/KEY: polyA_site
<222> LOCATION: (961)..(1080)
<223> OTHER INFORMATION: 120 nucleotide polyA tail
```

```
<400> SEQUENCE: 1
gggagacgcg uguuaaauaa caaaucucaa cacaacauau acaaaacaaa cgaaucucaa    60
gcaaucaagc auucuacuuc uauugcagca auuuaaauca uuucuuuuaa agcaaaagca   120
auuuucugaa aauuuucacc auuuacgaac gauagccgcc accaugcacu ggggaacccu   180
gugcggauuc cuguggcugu ggcccuaccu guucuaugug caagccgugc ccauccagaa   240
ggugcaggac gacaccaaga cccugaucaa gaccaucgug acccggauca acgacaucag   300
ccacacccag agcgugucca gcaagcagaa agugaccggc cuggacuuca uccccggccu   360
gcacccuauc cugacccugu ccaagaugga ccagacccug gccguguacc agcagaucca   420
gaccagcaug cccagccgga acgugaucca gaucagcaac gaccuggaaa accugcggga   480
ccugcugcac gugcuggccu ucagcaagag cugccaucug ccuugggcca gcggccugga   540
aacccuggau ucucuggggcg gagugcugga agccagcggc uacucuacag aggugguggc   600
ccugagcaga cugcagggca gccugcagga uaugcugugg cagcuggauc ugagccccgg   660
cugcuaauag cggaccggcg auagaugaag cucgcuuucu ugcuguccaa uuucuauuaa   720
agguuccuuu guucccuaag uccaacuacu aaacuggggg auauuaugaa gggccuugag   780
caucuggauu cugccuaaua aaaaacauuu auuuucauug cagcucgcuu ucuugcuguc   840
caauuucuau uaaagguucc uuuguucccu aaguccaacu acuaaacugg gggauauuau   900
gaagggccuu gagcaucugg auucugccua auaaaaaaca uuuauuuuca uugcggccgc   960
aaaaaaaaaa aaaaaaaaaa aaaaaaaaaa aaaaaaaaaa aaaaaaaaaa aaaaaaaaaa  1020
aaaaaaaaaa aaaaaaaaaa aaaaaaaaaa aaaaaaaaaa aaaaaaaaaa aaaaaaaaaa  1080
```

What is claimed is:

1. A method for the treatment of one or more diseases comprising administering one or more biologically active agent delivered by a composition comprising a compound of formula (II) or a pharmaceutically acceptable salt thereof:

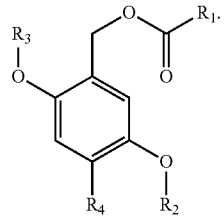
(II)

wherein $R_1$ is selected from

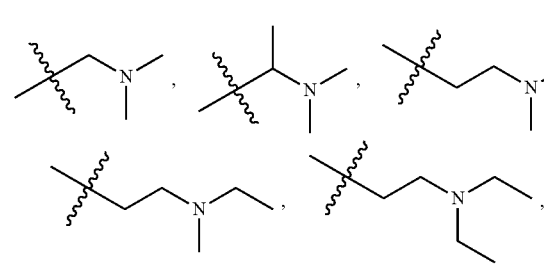

-continued

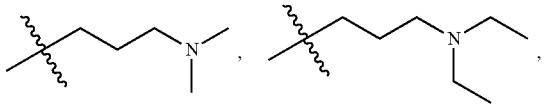

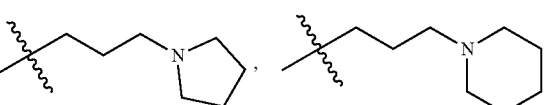

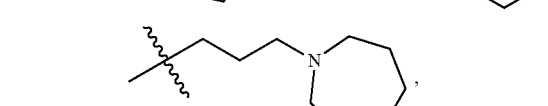

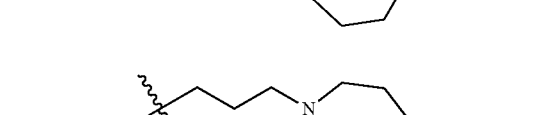

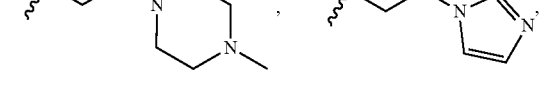

-continued
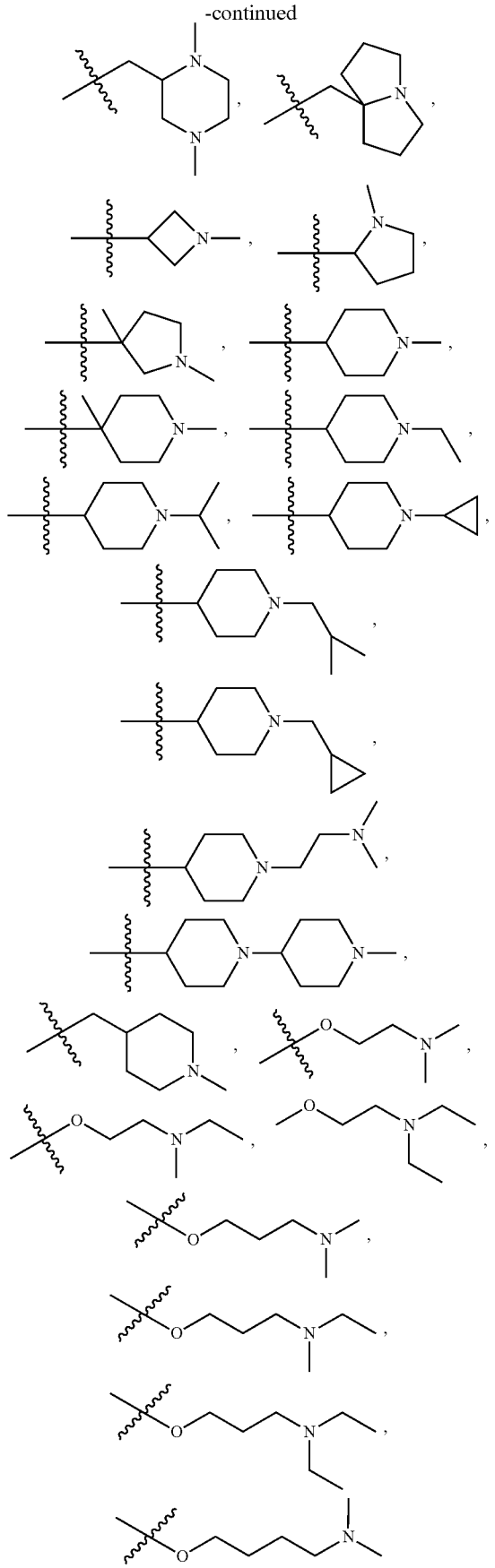
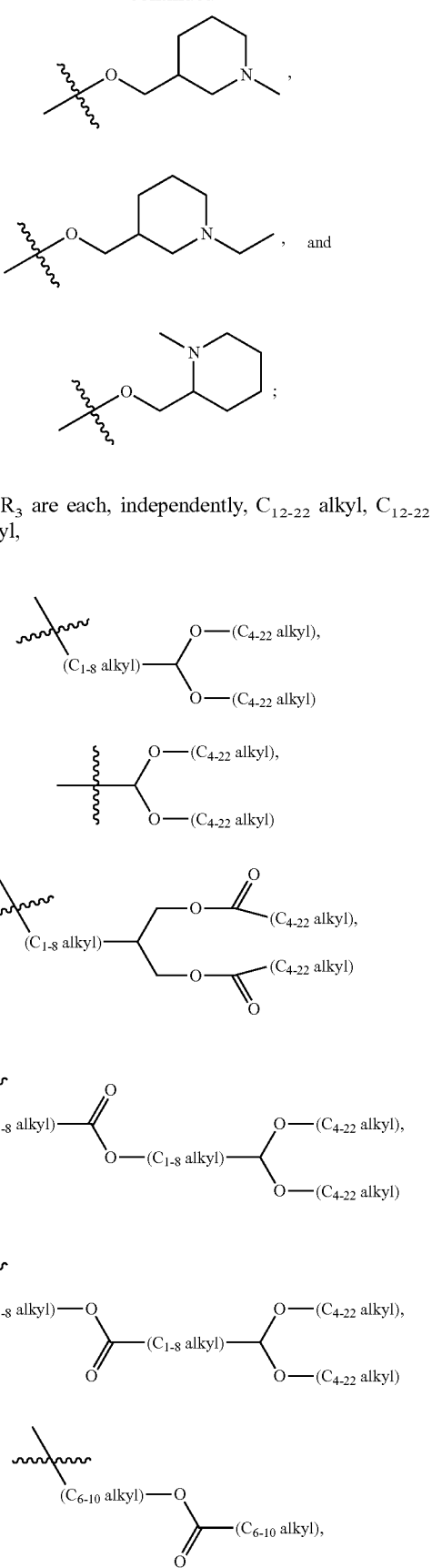
$R_2$ and $R_3$ are each, independently, $C_{12-22}$ alkyl, $C_{12-22}$ alkenyl, 133
-continued
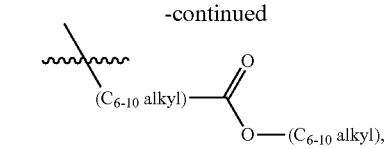
and
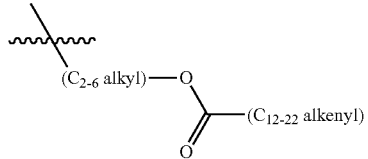
134
-continued
and
$R_4$ is selected from hydrogen, halo and $C_{1-4}$ alkyl.
2. The method according to claim 1, wherein $R_2$ is selected from:
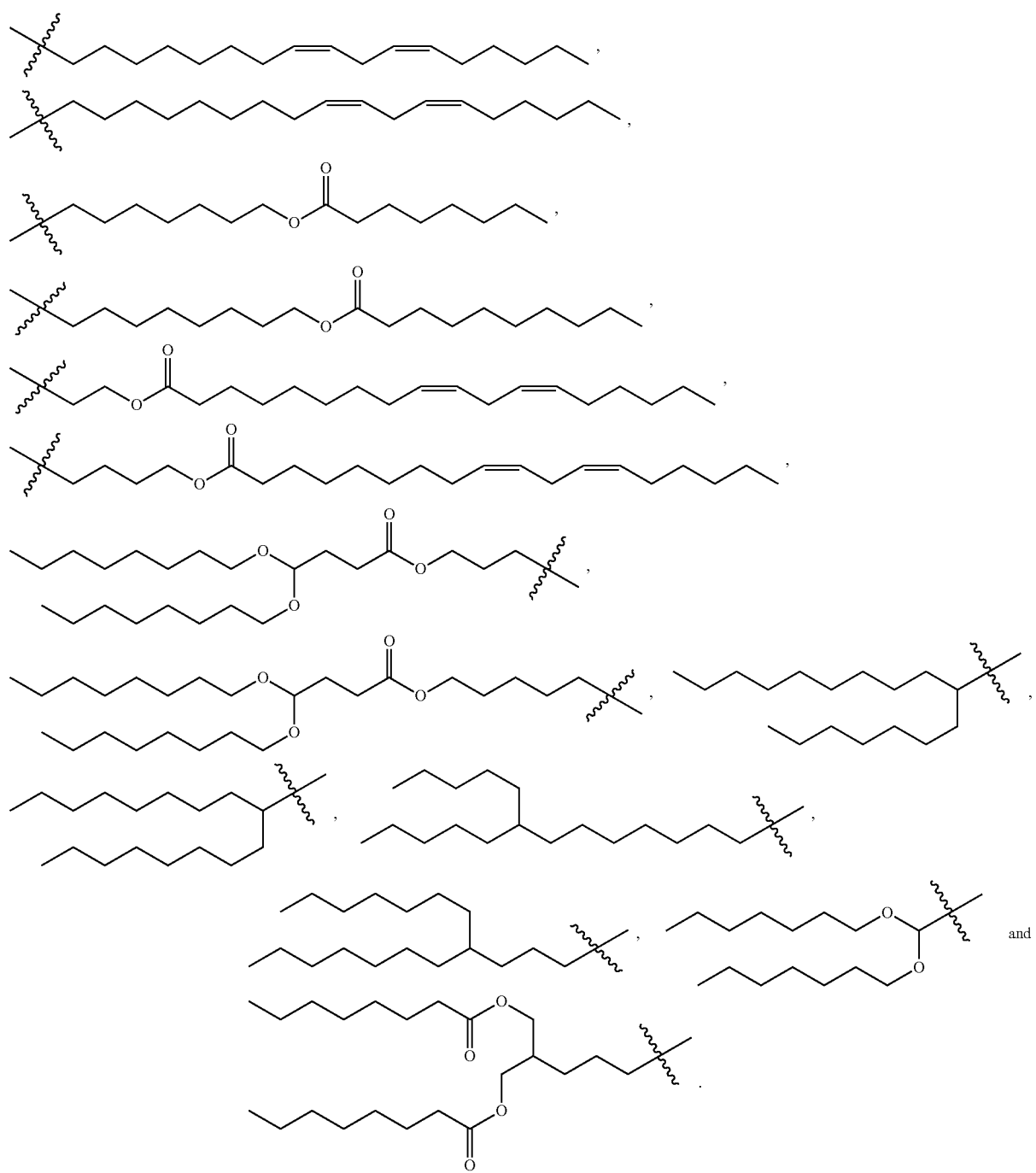

3. The method according to claim 1, wherein R₃ is selected from:

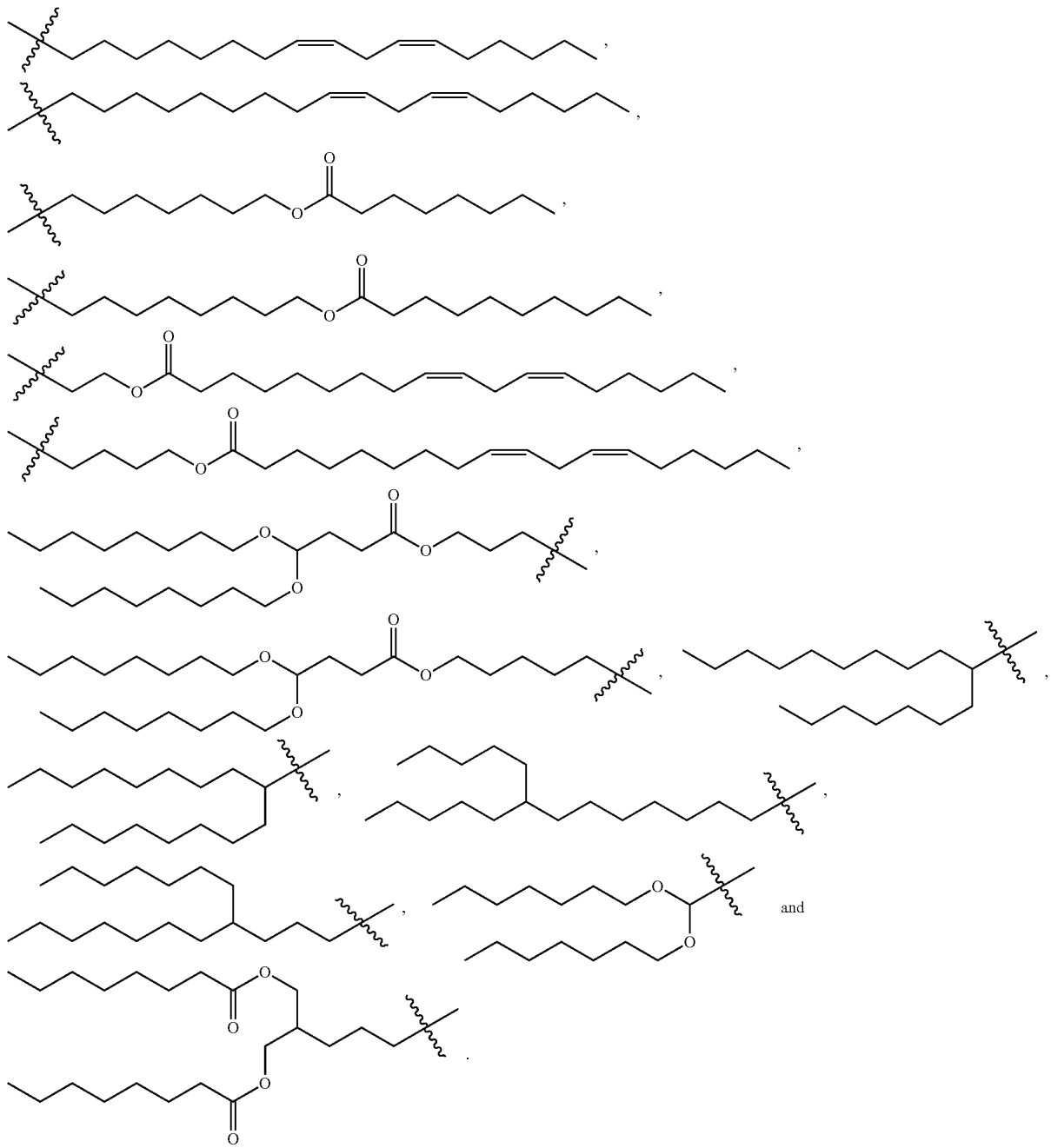

4. The method according to claim 1, wherein the compound is selected from:
  2,5-bis((9Z,12Z)-octadeca-9,12-dien-1-yloxy)benzyl 4-(dimethylamino)butanoate;
  ((2-(((4-(dimethylamino)butanoyl)oxy)methyl)-1,4-phenylene)bis(oxy))bis(octane-8,1-diyl) bis(decanoate);
  ((2-(((3-(dimethylamino)propanoyl)oxy)methyl)-1,4-phenylene)bis(oxy))bis(octane-8,1-diyl) bis(decanoate);
  ((2-(((1-methylpiperidine-4-carbonyl)oxy)methyl)-1,4-phenylene)bis(oxy))bis(octane-8,1-diyl) bis(decanoate);
  ((2-((((3-(dimethylamino)propoxy)carbonyl)oxy)methyl)-1,4-phenylene)bis(oxy))bis(octane-8,1-diyl) bis(decanoate);
  ((2-((((3-(diethylamino)propoxy)carbonyl)oxy)methyl)-1,4-phenylene)bis(oxy))bis(octane-8,1-diyl) bis(decanoate);
  3-(dimethylamino)propyl 4-methyl-2,5-bis((9Z,12Z)-octadeca-9,12-dien-1-yloxy)benzyl carbonate;
  4-methyl-2,5-bis((9Z,12Z)-octadeca-9,12-dien-1-yloxy)benzyl 4-(dimethylamino)butanoate;

(9Z,9'Z,12Z,12'Z)-((2-(((4-(dimethylamino)butanoyl) oxy)methyl)-1,4-phenylene)bis(oxy))bis(butane-4,1-diyl) bis(octadeca-9,12-dienoate);

4-(dimethylamino)butyl 4-methyl-2,5-bis((9Z,12Z)-octadeca-9,12-dien-1-yloxy)benzyl carbonate;

((2-(((1-ethylpiperidine-4-carbonyl)oxy)methyl)-1,4-phenylene)bis(oxy))bis(octane-8,1-diyl) bis(decanoate);

((2-(((1-isopropylpiperidine-4-carbonyl)oxy)methyl)-1,4-phenylene)bis(oxy))bis(octane-8,1-diyl) bis(decanoate);

((2-((2-(1-methylpiperidin-4-yl)acetoxy)methyl)-1,4-phenylene)bis(oxy))bis(octane-8,1-diyl) bis(decanoate);

((2-(((4-(pyrrolidin-1-yl)butanoyl)oxy)methyl)-1,4-phenylene)bis(oxy))bis(octane-8,1-diyl) bis(decanoate);

2,5-bis((9Z,12Z)-octadeca-9,12-dien-1-yloxy)benzyl (3-(dimethylamino)propyl) carbonate;

(9Z,9'Z,12Z,12'Z)-((2-(((4-(dimethylamino)butanoyl) oxy)methyl)-1,4-phenylene)bis(oxy))bis(ethane-2,1-diyl) bis(octadeca-9,12-dienoate);

2,5-bis((9Z,12Z)-octadeca-9,12-dien-1-yloxy)benzyl 3-(dimethylamino)propanoate;

2,5-bis((9Z,12Z)-octadeca-9,12-dien-1-yloxy)benzyl (3-(diethylamino)propyl) carbonate;

((2-(((4-(diethylamino)butanoyl)oxy)methyl)-1,4-phenylene)bis(oxy))bis(pentane-5,1-diyl) bis(4,4-bis(octyloxy)butanoate);

8-(4-((5-((4,4-bis(octyloxy)butanoyl)oxy)pentyl)oxy)-3-(((4-(dimethylamino)butanoyl)oxy)methyl)phenoxy) octyl decanoate;

8-(4-((5-((4,4-bis(octyloxy)butanoyl)oxy)pentyl)oxy)-2-(((4-(dimethylamino)butanoyl)oxy)methyl)phenoxy) octyl decanoate;

((2-(((4-(dimethylamino)butanoyl)oxy)methyl)-1,4-phenylene)bis(oxy))bis(propane-3,1-diyl) bis(4,4-bis(octyloxy)butanoate);

((2-(((4-(dimethylamino)butanoyl)oxy)methyl)-1,4-phenylene)bis(oxy))bis(pentane-5,1-diyl) bis(4,4-bis(octyloxy)butanoate); and ((2-(((1,4-dimethylpiperidine-4-carbonyl)oxy)methyl)-1,4-phenylene)bis(oxy))bis(pentane-5,1-diyl) bis(4,4-bis(octyloxy)butanoate).

5. The method according to claim 1, wherein the compound is 2,5-bis((9Z,12Z)-octadeca-9,12-dien-1-yloxy)benzyl 4-(dimethylamino)butanoate or a pharmaceutically acceptable salt thereof.

6. The method according to claim 1, wherein the disease is one or more of a proliferative disease, inflammatory disease, transplant rejection, tissue rejection, autoimmune disease, age-related disease, neurological disease, neurodegenerative disease, respiratory disease, cardiovacular disease, ocular disease, metabolic disease, dermatological disease, auditory disease, liver disease, kidney disease, and renal disease.

7. The method according to claim 1, wherein the biologically active agent is one or more of monoclonal antibodies, chimeric antibodies, humanized antibodies, nanobodies, antibody fragments, cholesterol, hormones, peptides, proteins, chemotherapeutics, antineoplastic agents, low molecular weight drugs, vitamins, co-factors, nucleosides, nucleotides, oligonucleotides, polynucleotides, enzymatic nucleic acids, antisense nucleic acids, triplex forming oligonucleotides, antisense DNA or RNA compositions, chimeric DNA:RNA compositions, allozymes, aptamers, ribozyme, decoys, analogs, plasmids, expression vectors, small nucleic acid molecules, mRNA, RNAi agents, short interfering nucleic acid (siNA), short interfering RNA (siRNA), double-stranded RNA (dsRNA), micro-RNA (miRNA), short hairpin RNA (shRNA), peptide nucleic acid (PNA), locked nucleic acid ribonucleotides (LNA), morpholino nucleotides, threose nucleic acid (TNA), glycol nucleic acid (GNA), sisiRNA (small internally segmented interfering RNA), aiRNA (assymetrical interfering RNA), and siRNA with 1, 2, or more mismatches between the sense and anti-sense strand to relevant cells or tissues.

8. The method according to claim 7, wherein the biologically active agent is a DNA, siRNA or mRNA.

9. The method according to claim 8, wherein the biologically active agent is a mRNA.

10. The method according to claim 1, wherein the composition further comprises a helper lipid.

11. The method according to claim 10, wherein the composition further comprises a neutral lipid.

12. The method according to claim 11, wherein the composition further comprises a stealth lipid.

13. The method according to claim 12, wherein the helper lipid is cholesterol, the neutral lipid is DSPC, and the stealth lipid is S010, S024, S027, S031, or S033.

14. The method according to claim 1, wherein the composition is in the form of a lipid nanoparticle.

15. A method for the treatment of one or more diseases comprising administering one or more biologically active agent delivered by a composition comprising a compound 2,5-bis((9Z,12Z)-octadeca-9,12-dien-1-yloxy)benzyl 4-(dimethylamino)butanoate or a pharmaceutically acceptable salt thereof.

16. The method according to claim 15, wherein the disease is one or more of a proliferative disease, inflammatory disease, transplant rejection, tissue rejection, autoimmune disease, age-related disease, neurological disease, neurodegenerative disease, respiratory disease, cardiovacular disease, ocular disease, metabolic disease, dermatological disease, auditory disease, liver disease, kidney disease, and renal disease.

17. The method according to claim 15, wherein the biologically active agent is one or more of monoclonal antibodies, chimeric antibodies, humanized antibodies, nanobodies, antibody fragments, cholesterol, hormones, peptides, proteins, chemotherapeutics, antineoplastic agents, low molecular weight drugs, vitamins, co-factors, nucleosides, nucleotides, oligonucleotides, polynucleotides, enzymatic nucleic acids, antisense nucleic acids, triplex forming oligonucleotides, antisense DNA or RNA compositions, chimeric DNA:RNA compositions, allozymes, aptamers, ribozyme, decoys, analogs, plasmids, expression vectors, small nucleic acid molecules, mRNA, RNAi agents, short interfering nucleic acid (siNA), short interfering RNA (siRNA), double-stranded RNA (dsRNA), micro-RNA (miRNA), short hairpin RNA (shRNA), peptide nucleic acid (PNA), locked nucleic acid ribonucleotides (LNA), morpholino nucleotides, threose nucleic acid (TNA), glycol nucleic acid (GNA), sisiRNA (small internally segmented interfering RNA), aiRNA (assymetrical interfering RNA), and siRNA with 1, 2, or more mismatches between the sense and anti-sense strand to relevant cells or tissues.

18. The method according to claim 17, wherein the biologically active agent is a DNA, siRNA or mRNA.

19. The method according to claim 18, wherein the biologically active agent is a mRNA.

20. The method according to claim 15, wherein the composition further comprises a helper lipid.

21. The method according to claim 20, wherein the composition further comprises a neutral lipid.

22. The method according to claim 21, wherein the composition further comprises a stealth lipid.

23. The method according to claim 22, wherein the helper lipid is cholesterol, the neutral lipid is DSPC, and the stealth lipid is S010, S024, S027, S031, or S033.

24. The method according to claim 15, wherein the composition is in the form of a lipid nanoparticle.

* * * * *